US006951682B1

(12) United States Patent
Zebala

(10) Patent No.: US 6,951,682 B1
(45) Date of Patent: Oct. 4, 2005

(54) POROUS COATINGS BEARING LIGAND ARRAYS AND USE THEREOF

(75) Inventor: John A. Zebala, Redmond, WA (US)

(73) Assignee: Syntrix Biochip, Inc., Auburn, WA (US)

(*) Notice: Subject to any disclaimer, the term of this patent is extended or adjusted under 35 U.S.C. 154(b) by 0 days.

(21) Appl. No.: 09/332,815

(22) Filed: Sep. 17, 1999

Related U.S. Application Data

(60) Provisional application No. 60/110,529, filed on Dec. 1, 1998.

(51) Int. Cl.[7] .............................. B32B 3/10; B32B 3/26; C12Q 1/00; G01N 33/53; G01N 33/543
(52) U.S. Cl. ................................ 428/312.2; 428/321.6; 428/312.8; 428/315.7; 428/317.1; 428/195; 435/4; 435/7.1; 435/7.7; 435/7.71; 435/7.72; 435/7.8; 435/7.9; 436/518; 436/519; 436/523
(58) Field of Search .............................. 428/195, 312.2, 428/312.6, 312.8, 315.5, 315.7, 317.1, 317.9, 318.4, 319.1; 435/4, 7.1, 7.7, 7.71, 7.72, 7.8, 7.9, 7.91, 7.92, 7.93, 7.94, 7.95; 436/518, 519, 523

(56) References Cited

U.S. PATENT DOCUMENTS

| 4,757,014 A | * | 7/1988 | Hendrickson et al. ...... 435/180 |
| 5,001,453 A | * | 3/1991 | Ikejiri et al. ................. 338/35 |
| 6,159,681 A | * | 12/2000 | Zebala .......................... 435/4 |

FOREIGN PATENT DOCUMENTS

| EP | WO 98/41534 | * | 9/1998 |

* cited by examiner

Primary Examiner—Cheryl A. Juska
(74) Attorney, Agent, or Firm—Peter J. Knudsen

(57) ABSTRACT

Articles comprising substantially uniform porous coatings, which may be photopatterned, are provided. The use of such porous coatings increases the surface density of attached compounds within, for example, ligand arrays prepared by methods such as regionally selective solid-phase chemical synthesis. Arrays prepared using the porous coatings may be used within a variety of diagnostic and drug discovery assays.

155 Claims, 9 Drawing Sheets

Objective Magnification  No Coating (prior art)

2x

Objective Magnification  Patterned Porous Coating (present invention)

2x

| Objective Magnification | No Coating (prior art) | Objective Magnification | Patterned Porous Coating (present invention) |
|---|---|---|---|
| 2x |  | 2x | 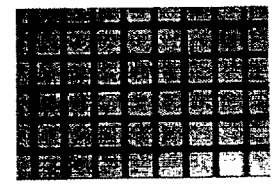 |

| Objective Magnification | No Coating (prior art) | Objective Magnification | Patterned Porous Coating (present invention) |
|---|---|---|---|
| 10x |  | 10x | 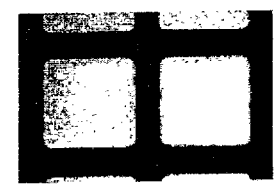 |

| Objective Magnification | No Coating (prior art) | Objective Magnification | Patterned Porous Coating (present invention) |
|---|---|---|---|
| 20x | 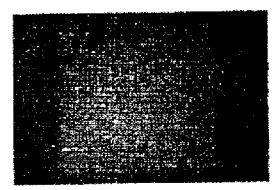 | 20x |  |

Receptor: None — Fluorescence Image

Receptor: None — Surface Plot

Receptor: FTA — Fluorescence Image

Receptor: FTA — Surface Plot

Receptor: FAA — Fluorescence Image

Receptor: FAA — Surface Plot

PNA array contacted by FAA receptor

Receptor Sequence  5' – GCGAAGGC – F

Array schematic

| AT | GT | CT | TT |
|----|----|----|----|
| AC | GC | CC | TC |
| AG | GG | CG | TG |
| AA | GA | CA | TA |

*Fig. 6A*

PNA array contacted by FTA receptor

Receptor Sequence  5' – GCGTAGGC – F

Array schematic

| AT | GT | CT | TT |
|----|----|----|----|
| AC | GC | CC | TC |
| AG | GG | CG | TG |
| AA | GA | CA | TA |

*Fig. 6B*

PNA array contacted by FAA receptor

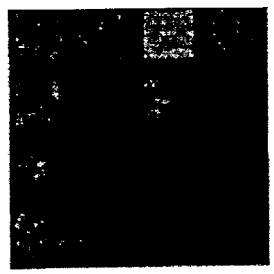

Fluorescence Image

*Fig. 6C*

PNA array contacted by FTA receptor

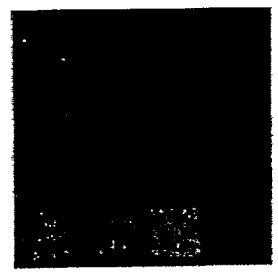

Fluorescence Image

*Fig. 6D*

PNA array contacted by FAA receptor

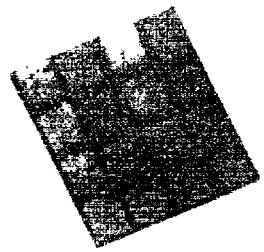

Surface Plot

*Fig. 6E*

PNA array contacted by FTA receptor

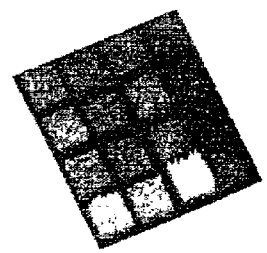

Surface Plot

*Fig. 6F*

Array Schematic
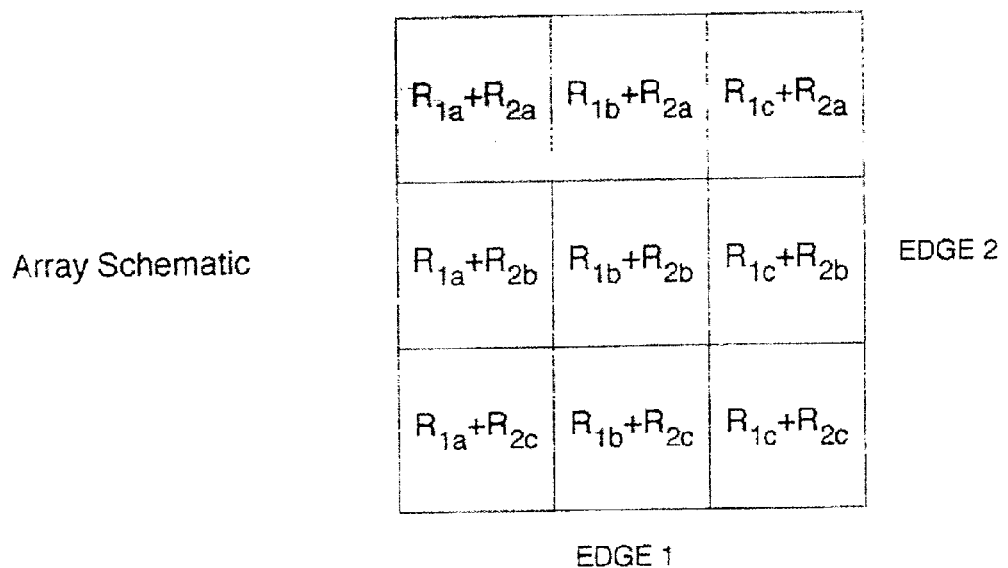
Surface Plot
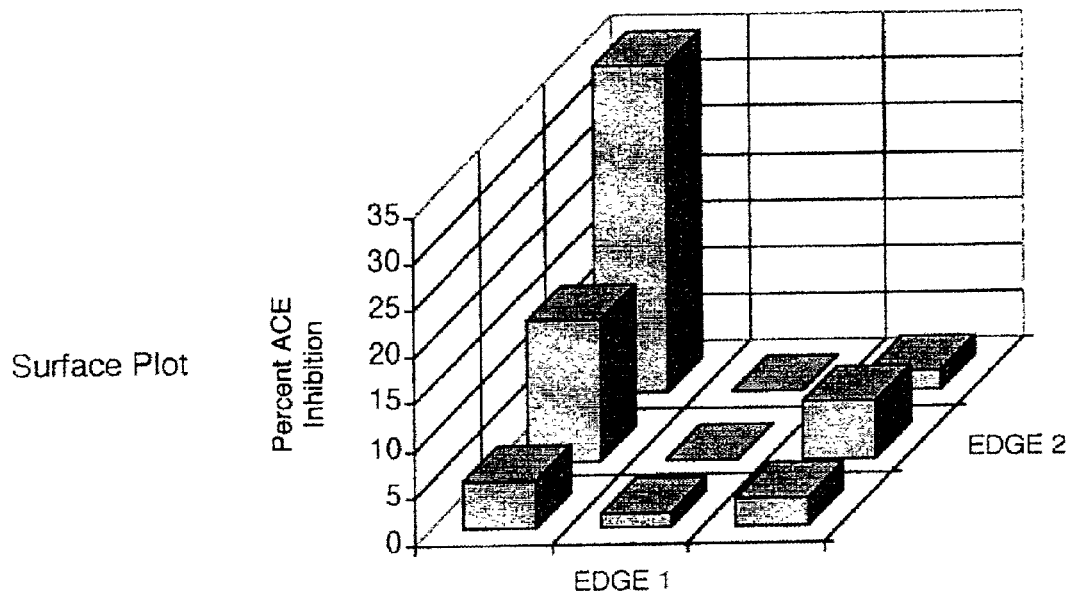
Fig. 7

US 6,951,682 B1

POROUS COATINGS BEARING LIGAND ARRAYS AND USE THEREOF

CROSS REFERENCE TO RELATED APPLICATIONS

This Application claims the benefit of U.S. Provisional Application No. 60/110,529, filed Dec. 1, 1998.

TECHNICAL FIELD

The present invention relates generally to articles comprising porous coatings, and to methods for preparing and using such articles. The invention is more particularly related to methods for fabricating articles having patterned porous coatings, which may be used, for example, to screen large numbers of discrete compounds for diagnostic or drug discovery purposes.

BACKGROUND OF THE INVENTION

Receptor-ligand interactions are critical components of many fundamental biological processes. Such interactions involve specific binding of a macromolecule receptor (e.g., enzyme, cell-surface protein, antibody or oligonucleotide) to a particular ligand molecule. Receptor-ligand binding may affect any of a variety of intercellular and intracellular processes in an organism, such as signal transduction, gene expression, immune responses or cell adhesion. An improved understanding of receptor-ligand interactions is necessary for many areas of research in the life sciences, as well as for the development of agents that modulate such interactions for therapeutic and other applications.

Miniaturized ligand-arrays, formed using microfabrication and solid-phase chemical synthesis on substantially planar supports, have been used to facilitate the study of receptor-ligand interactions (for representative examples, see Fodor et al., Science (1991) 251:767; Pease et al., *Proc. Natl. Acad. Sci. USA* 91:5022, 1994; Pirrung et al., U.S. Pat. No. 5,405,783; Fodor et al., U.S. Pat. No. 5,445,934; Pirrung et al., U.S. Pat. No. 5,143,854; Fodor et al., U.S. Pat. No. 5,424,186 and Fodor et al., U.S. Pat. No. 5,510,270; Chee et al., Science (1996) 274:610 and Brennan, U.S. Pat. No. 5,474,796). Contacting a ligand array with labeled receptor allows many ligands to be simultaneously screened for receptor binding. The location of bound receptor on the array is determined by detecting photons or radioactivity. However, the surface density of ligand is often low, resulting in the need for costly imaging equipment and long image acquisition times. Drug discovery efforts have been further hampered by low ligand surface density, since many functional assays require higher ligand concentrations to identify drug leads.

One approach to increasing surface density of ligands involves immobilizing ligands on an array of polyacrylamide pads using microfabrication techniques (see Guschin et al., *Anal. Biochem.* 250:203, 1997 and Yershov et al., *Proc. Natl. Acad. Sci. USA* 93:4913, 1996). Such an approach increases the surface density of the ligands, but places a size restriction on diffusion into the polymer that many receptors exceed. Furthermore, such polymeric supports may not be compatible with solid-phase chemical synthesis, which requires adequate swelling and salvation of a polymeric matrix in order to achieve efficient mass transfer of reagents. Further, although this polymer can be photopatterned (i.e., multiple discrete pads may be generated by a process involving exposure to irradiation), the photosensitivity is severely limited, requiring 30 minutes of illumination. Such a low throughput is inadequate for mass production.

Existing techniques for increasing ligand density on a solid support provide insufficient surface area enhancement. Such techniques include the use of acid-etched porous silicon and an electrochemically manufactured metal oxide membrane as substrates for detecting the specific binding of ligands by receptors (see Beattie et al., *Clin. Chem.* 41:700, 1995 and Van Damme and Kreuwel, WO99/02266). The porous silicon is macroporous with 3 to 5 micron diameter pores arranged in parallel and oriented perpendicular to the substrate surface. Relative to nanoporous materials, a macroporous configuration has inadequate surface area to significantly increase ligand surface density. Although the electrochemically manufactured metal oxide membrane has pores as small as 0.2 microns, it too provides little surface area enhancement with only a 10-fold increase in surface area for each micron of membrane thickness.

Additionally, the parallel pore orientation of these substrates is technically cumbersome, since it requires a flow-through apparatus in order for receptor to bind ligand. Further, it is unclear whether such substrates could function as solid supports for multiple rounds of synthetic reactions. The electrochemically manufactured metal oxide membrane also suffers from incompatibility with microfabrication methods.

Rigid porous supports that do not require swelling in solvents and are compatible with attachment of ligands or receptors offer the potential to increase ligand surface density by providing a high surface area for ligand attachment. For example, porous bodies have been made from slurries consisting of a binder and particles having a high surface area (see Messing, U.S. Pat. No. 3,910,851 and Messing, in: Methods in *Enzymology*, vol. XLIV, p. 149, edited by Klaus Mosbach, (1976), Academic Press N.Y.). However, to date, porous supports and coatings have not been successfully applied to microfabrication of ligand arrays.

Porous coatings with controlled porosity have been obtained by sol-gel and particulate methods (see Frye et al., U.S. Pat. No. 5,224,972; Frye et al., U.S. Pat. No. 5,589,396; Suppiah, U.S. Pat. No. 5,120,600 and Frye et al., in: *Better Ceramics Through Chemistry IV*, vol. 180, Mat. Res. Soc. Symp. Proc., edited by Brinker et al., (1990), p. 583). Such methods produce controlled porous coatings with chemically modified surfaces for the purpose of providing steric and chemical selectivity to a sensor surface, via nonspecific molecular interactions (e.g. chelation and ion exchange). Such coatings have not been used as supports for detecting the specific binding characteristic of macromolecular receptors or to create arrays of complex ligands. Further such coatings cannot be made greater than one micron thick without multiple coats, and have not been successfully patterned by microfabrication methods.

Other porous coatings suffer from incompatibility with solid phase ligand synthesis. From the field of imaging, positive and negative images can be formed in coatings of photosensitized colloidal particles (see Pu et al., *J Imaging Sci.* 33:177, 1989). Such coatings consist of a phenolic resin (0% to 15%), a bis-azide (optional), and colloidal particles encapsulated by organic polymer, diacid chlorides, and photoactive azide groups. Although these coatings may be patterned using microfabrication techniques, they have not been used to increase ligand surface density, detect ligand-receptor binding or prepare ligand arrays by solid-phase chemical synthesis. In fact, organic solvents would be expected to swell and distort existing coatings, making them incompatible with solid-phase synthesis.

Still further porous inorganic coatings have been designed to reduce reflectivity. For example, both aged and unaged colloidal dispersions have been used to form continuous porous coatings of uniform thickness (see Cathro et al., *Solar Energy* 32:573, 1984 and Lange et al., U.S. Pat. No. 4,816,333). The resulting dried coatings are from about 0.02 $\mu$m to 0.50 $\mu$m thick. Although the surface area of a porous coating may be increased by increasing its thickness, uniform colloidal coatings greater than about 1.5 $\mu$m thick cannot be obtained without using certain additives (see Daniels et al., in: *Better Ceramics Through Chemistry VII*, vol. 435, Mat. Res. Soc. Symp. Proc., edited by Coltrain et al., (1996), p. 215). Even with additives, such coatings still form cracks. In fact, colloidal coatings typically are non-uniform and discontinuous (see Moulton, U.S. Pat. No. 2,601,123). Further, colloidal coatings have not been patterned using microfabrication techniques, or used to increase ligand surface density, detect ligand-receptor binding, or prepare ligand arrays by solid-phase chemical synthesis.

Accordingly, there is a need in the art for methods for increasing ligand density on a surface in a manner that is fully compatible with microfabrication. In particular, there is a need for improved articles for use in the detection of macromolecular receptor binding, and the production of ligand arrays by solid-phase synthetic methods. The present invention fulfills these needs and further provides other related advantages.

SUMMARY OF THE INVENTION

Briefly stated, the present invention provides articles comprising porous coatings and attached ligands, and methods for preparing and using such articles. Within certain aspects, the present invention provides coated articles comprising a substrate having a continuous porous coating of substantially uniform thickness, wherein the coating comprises a gelled network of particles, and wherein the porous coating has two or more different compounds attached thereto. Suitable particles may comprise one or more of carbon, activated carbon, fluorinated carbon, styrenedivinylbenzene copolymers, polystyrene, zeolites, oxides of antimony and oxides of metals present within Group III and Group IV of the Periodic Table. The primary particle size is preferably less than 1000 Å. Within certain embodiments, the gelled network of particles further comprises a polymer of a partially or substantially hydrolyzed metal alkoxide. Substrates include glass and may, but need not, comprise an adhesive layer. Attachment of compounds to the porous coating may be covalent or via adsorption, with or without the use of a linker. Preferred compounds include nucleobase polymers, peptides and enalaprilat analogues.

Within further aspects, methods are provided for making a coated article with two or more compounds attached thereto, comprising the steps of: (a) applying to a substrate a substantially uniform layer of a solution comprising metal oxide particles dispersed in a volatile liquid; (b) evaporating the volatile liquid from the layer, forming a gelled network of metal oxide particles on the substrate, wherein the gelled network forms a porous coating ranging from 0.05 to 25 microns thick; and (c) attaching two or more compounds to discrete known regions of the porous coating. The solution may further comprise extended polymers of a substantially hydrolyzed metal alkoxide linked to the metal oxide particles, wherein the weight ratio of metal oxide particles to the substantially hydrolyzed metal alkoxide ranges from 1 to 1000. Optionally, prior to the step of attaching two or more compounds, the porous coating is cured at a temperature and for a time sufficient to increase the porous coating strength.

Within further aspects, the present invention provides coated articles comprising a substrate having at least two discrete known regions with porous coatings, wherein each coating has a substantially uniform thickness, is continuous and comprises a gelled network of particles, and wherein each porous coating has at least one compound attached thereto. Suitable particles may comprise one or more of carbon, activated carbon, fluorinated carbon, styrenedivinylbenzene copolymers, polystyrene, zeolites, oxides of antimony and oxides of metals present within Group III and Group IV of the Periodic Table. The primary particle size is preferably less than 1000 Å. Within certain embodiments, the gelled network of particles further comprises a polymer of a partially or substantially hydrolyzed metal alkoxide. Substrates include glass and may, but need not, comprise an adhesive layer. Attachment of compounds to the porous coating may be covalent or via adsorption, with or without the use of a linker. Preferred compounds include nucleobase polymers, peptides and enalaprilat analogues.

The present invention further provides methods for making a coated article comprising a substrate and at least two separate porous coatings, comprising the steps of: (a) applying to a substrate a substantially uniform layer of a solution comprising metal oxide particles dispersed in a volatile liquid; (b) evaporating the volatile liquid from the layer, forming a gelled network of metal oxide particles on the substrate, wherein the gelled network forms a porous coating ranging from 0.05 to 25 microns thick; (c) covering the porous coating with a layer of photoresist comprising a base soluble component; (d) irradiating the photoresist, such that a first region of photoresist is rendered substantially removable with an aqueous alkaline developer, and such that a second region is not so removable; (e) contacting at least the first region with an aqueous alkaline developer to remove at least the first region of photoresist and porous coating underlying the first region, without substantially removing the second region of photoresist or porous coating underlying the second region; (f) removing remaining photoresist with an organic solvent, resulting in separate porous coatings on discrete regions of the substrate; and (g) attaching one or more compounds to each of the separate porous coatings. The solution may further comprise extended polymers of a substantially hydrolyzed metal alkoxide linked to the metal oxide particles, wherein the weight ratio of metal oxide particles to the substantially hydrolyzed metal alkoxide ranges from 1 to 1000. Optionally, prior to the step of attaching two or more compounds, the porous coating is cured at a temperature and for a time sufficient to increase the porous coating strength.

Within further aspects, the present invention provides methods for identifying at least one compound that specifically binds a receptor, the method comprising the sequential steps of: (a) contacting a coated article as described above with a receptor; and (b) determining whether one or more of the compounds attached to the porous coating specifically bind to the receptor.

The present invention further provides methods for identifying at least one compound that specifically binds a receptor, the method comprising the steps of: (a) simultaneously or in either order (i) detaching one or more compounds from a coated article as described above; and (ii) contacting the detached compound(s) with a receptor; and (b) determining whether the compound(s) specifically bind to the receptor.

Within other aspects, methods are provided for isolating a target receptor, comprising the steps of: (a) contacting a coated article as described above with a composition comprising a target receptor, wherein at least one attached compound binds to the target receptor; (b) removing unbound components of the composition from the array; and (c) separating the target receptor from the coated article.

Methods are further provided for modifying a receptor, comprising contacting a coated article as described above with a composition comprising a target receptor, wherein at least 5% of the attached compounds comprise a target receptor modifying group that labels, reconforms, cleaves, covalently binds or intercalates into a bound target receptor.

Within other aspects, the present invention provides methods for hybridizing an antisense molecule to a target nucleic acid molecule, comprising the steps of: (a) contacting a coated article as described above with a composition comprising a target nucleic acid molecule, wherein the attached compounds are antisense molecules; and (b) detaching one or more compounds from the array.

Methods are further provided, within other aspects, for hybridizing an antisense molecule to a target nucleic acid molecule, comprising the steps of: (a) detaching one or more compounds from a coated article as described above, wherein the attached compounds are antisense molecules; and (b) contacting the compound(s) with a composition comprising a target nucleic acid molecule.

The present invention further provides coated articles comprising a substrate having a continuous porous coating thereon of substantially uniform thickness, wherein the porous coating comprises a continuous gelled network of metal oxide particles and polymers of hydrolyzed metal alkoxide, wherein the porosity of the coating ranges from 0.15 to 0.99.

Within other aspects, the present invention provides coated articles comprising a substrate having at least five separate distinct porous coatings per square centimeter, wherein each coating is continuous and has a substantially uniform thickness and comprises a continuous gelled network of particles.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 4A–4F are prints from an epifluorescence microscope at objective magnifications of 2×(FIGS. 4A and 4B), 10×(FIGS. 4C and 4D), and 20×(FIGS. 4E and 4F) that show ligand surface density according to an existing method (i.e., no coating; FIGS. 4A, 4C and 4E), and using a representative porous coating as provided herein (FIGS. 4B, 4D and 4F). The ligand is FITC attached to the free amino group of aminopropyltriethoxysilane bound to the surface.

FIGS. 6A–6F are schematics (FIGS. 6A and 6B), epifluorescence microscope prints (FIGS. 6C and 6D) and surface plots (FIGS. 6E and 6F) illustrating the specific binding of a ligand array by two different fluorescently labeled receptors (FAA or FTA, as indicated) on a patterned porous coating according to the present invention, wherein both receptors are DNA, and the ligand array is a peptide nucleic acid (PNA) array. The symbol "F" indicates fluorescein. Shaded grids on the ligand array schematics indicate the predicted location of receptor binding. The ligand array was synthesized on the patterned porous coating by photolithography and solid-phase synthetic methods.

FIGS. 7A and 7B are a schematic (FIG. 7A) and a plot of enzyme inhibition (FIG. 7B) from an array of weakly inhibitory ligands synthesized on a representative patterned porous coating, wherein the enzyme is angiotensin converting enzyme (ACE), and the ligands are analogues of enalaprilat, the active metabolite of the antihypertensive drug enalapril. The ligand array was synthesized on the patterned porous coating by photolithography and solid-phase synthetic methods. The surface plot illustrates percent ACE inhibition as a function of array position.

DETAILED DESCRIPTION OF THE INVENTION

Figure 1A:
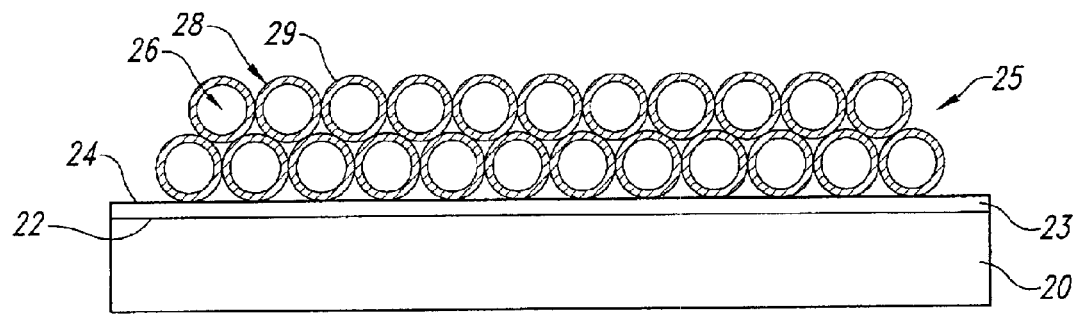
FIG. 1A is a diagram illustrating a cross-section of a representative article comprising a porous coating 25 with an attached ligand 31 and linker 30. Surface 22 of substrate 20 is provided with an adhesive layer 23 having an adhesive surface 24. The porous coating 25 is substantially uniform in thickness, and comprises a continuous gelled-network of substantially spherical metal oxide particles 26 and a metal alkoxide polymer 28. The surface area is formed by the porous coating surface 29.
Figure 1B:
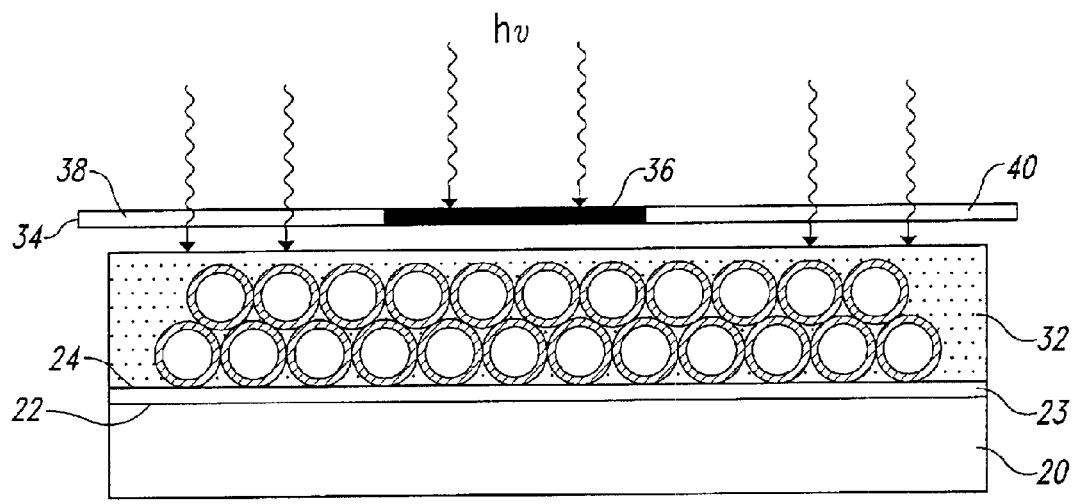
FIG. 1B is a diagram illustrating a cross-section of a representative article as shown in FIG. 1A, following application of photoresist layer 32 and during irradiation. An opaque region 36 of mask 34 is used to block light radiation to a first region of photoresist layer 32. Transparent regions 38 and 40 of the mask allow light to irradiate second and third regions of the photoresist layer, respectively. The thickness of photoresist layer 32 is sufficient to substantially cover porous coating 25 and fill its pore volume.

As noted above, the present invention is generally directed to articles comprising porous coatings. The present invention is based, in part, on the discovery that a uniform, crack-free porous coating up to 25 μm thick can be generated in which pore size may be tailored so as to optimize both surface area and mass transfer characteristics. Such coatings increase ligand surface density with low autofluorescence, and can be applied and patterned with high sensitivity using microfabrication techniques. Porous coatings provided herein are compatible with the production of ligand arrays by solid-phase synthesis, do not swell or distort substantially during ligand-receptor binding or solid-phase chemical synthesis and do not require a flow-through apparatus, resulting in economical and rapid imaging of ligand arrays. The enhanced ligand surface density provided by the coatings described herein is sufficient to perform functional assays using ligands from individual array elements, and with low to moderate binding affinities.

Porous coatings provided herein may be used, for example, to prepare arrays of ligands (e.g., nucleobase polymers). Ligand arrays as described herein may be used in analyses that require a large number of discrete compounds on a solid support, such as within screens to detect ligand-receptor binding for diagnostic or drug discovery purposes.

Glossary

Prior to setting forth the invention in detail, it may be helpful to an understanding thereof to set forth definitions of certain terms that will be used hereinafter.

An "acid labile moiety" is a portion of a molecule that is cleaved upon exposure to a particular acidic chemical or pH. Similarly, a "base labile moiety" is a portion of a molecule that is cleaved upon exposure to a particular basic chemical or pH.

An "adhesive layer" is a coating that is stably attached to the surface of a substrate to facilitate adhesion of a porous coating to the substrate. Stable attachment may be assessed by a modification of ASTM Test Method D3330, wherein a 1.9 cm wide strip of Scotch Brand Magic transparent tape, available from 3M company, is adhered to the test layer by rolling a 2 kg roller back and forth twice across the tape. The tape is then peeled from the test sample at 1800 at a rate of 2 cm/min. Stable attachment is defined as a 180° peelback value of greater than about 25 g/cm, and more preferably greater than about 150 g/cm. The ability of an adhesive layer to facilitate porous coating attachment may be readily assessed by the modified ASTM Test Method D3330 as described above. An adhesive layer is said to facilitate porous coating attachment if it has a 180° peelback value of greater than about 15 g/cm, or if there is a split in the porous coating leaving residual porous coating on the adhesive layer. In certain preferred embodiments, the adhesive layer comprises partially, substantially or fully hydrolyzed monomers, oligomers, and/or extended polymers of a metal oxide or organo-metal alkoxide. Within such polymers, coupling is achieved through "oxane" bonds (i.e., "-M-O-M-"; condensation products of: -M-OH+OH-M-→M-O-M-+$H_2O$, where M is a metal) In another preferred embodiment, the adhesive layer comprises a substantially hydrolyzed tetraethyoxysilane. In some embodiments the thickness of the adhesive layer is less than 0.001 μm, 0.01 μm, 0.1 μm, 1.0 μm, or 10.0 μm. Preferably, the thickness is between 0.1 μm and 1.0 μm.

"Aging" of a composition refers to the process of forming extended polymers according to the sol-gel method. Such polymers may be linear or crosslinked polymers. Aging may proceed in the liquid (i.e., "sol"), gel and/or solid states, and generally refers to the period over which the number of condensed chemical bonds is increasing. Bond condensation may reach an equilibrium in the liquid, gel or solid states. Bond condensation or "aging" may be monitored using techniques described below (see "extended polymer"). A sol is said to be "aged" when bond condensation has progressed to yield extended polymers. Aged solutions described in this specification are preferably aged until an equilibrium of bond condensation is reached in the liquid state. Equilibrium may be detected using techniques described below (see "extended polymer").

"Amplification" refers to a detectable increase in the number of copies of a particular nucleic acid fragment or other biologic molecule, usually resulting from an enzymatic reaction such as the polymerase chain reaction (PCR).

An "antisense molecule" is a nucleobase polymer that has a sequence that is at least partially complementary to a nucleic acid molecule of interest, and which detectably modulates the expression and/or activity of the nucleic acid via hydrogen bonding interactions. Also encompassed are nucleobase polymers that are candidates for possessing such modulating activity (e.g., an array of antisense molecules may comprise multiple nucleobase polymers that are to be screened for antisense properties). The ability to modulate nucleic acid activity by antisense regulation is well known in the art (reviewed in Uhlmann and Peyman, *Chem. Rev.* 90(4):544, 1990 and Schreier, *Pharm. Acta Helv.* 68(3):145, 1994). With respect to the control of gene expression, antisense molecules can be used not only to inhibit expression, but also to activate it in vitro and in vivo. Indirect activation of gene expression can be accomplished, for example, by suppressing the biosynthesis of a natural repressor, as described for antisense oligodeoxynucleotides by Inoue (see Inoue, *Gene* 72:25, 1988) Direct activation of gene expression can be accomplished, for example, by reducing termination of transcription as described for antisense oligodeoxynucleotides by Winkler et al. (see Winkler et al., *Proc. Natl. Acad. Sci. USA* 79:2181, 1982). There are several in vitro and in vivo test systems known in the art that have been routinely used (see Crooke, *Anticancer Drug Des.* 6:609, 1991; Hanvey et al., *Science* 258:1481, 1992; Lisziewicz et al., *Proc. Natl. Acad. Sci. USA* 89.11209, 1992; Woolf et al., *Proc. Natl. Acad. Sci. USA* 89:7305, 1992; Nielsen et al., *Anticancer Drug Des.* 8:53, 1993 and Zeiphati et al., *Antisense Res. Dev.* 3:323, 1993). The efficacy of antisense molecules in a ligand-array can be easily tested and compared using these test systems.

A compound is said to be "attached" to a substrate surface if the compound substantially remains on the surface during photoresist application and removal (i.e., at least 60% of the attached compounds are not removed when such processes are performed as described herein). The percentage of compounds removed under particular conditions may be readily determined using labeled molecules, and monitoring the loss of label during photoresist application and removal. Attachment may be covalent or non-covalent. Noncovalent interactions that may be employed include, for example, electrostatic interactions, hydrogen bonding, metal coordination, Van der Waals interactions, and magnetism. In some embodiments, a mixture of covalent and noncovalent interactions may be used. Suitable magnetizing agents for use in a magnetic field include paramagnetic lanthanide ions such as erbium, dysprosium, holmium, thulium, and gadolinium (see Zborowski et al., *J. Gen. Microbiology* 138:63, 1992; Russell et al., *Analytical Biochem.* 164:181, 1987; and Evans and Tew, *Science* 213:653, 1983). Alternatively, micron-scale and smaller magnetic affinity particles may be used such as ferritin, dextran magnetite, and magnetic porous glass (see Hirschbein et al., *Chemtech* pg. 172, March, 1982; Viroonchatapan et al., *Pharm. Res.* 12:1176, 1995; and CPG Inc., Lincoln Park, New Jersey).

A "barrier layer" is a layer of photoresist that prevents detectable contact of a reagent on one side of the layer with a molecule on the other side over a time required for a particular reaction. In other words, a reagent that reacts in a detectable manner with a molecule when the two are combined in solution should not react detectably when separated from the molecule by a barrier layer. In some embodiments the barrier layer will be absolute, preventing detectable contact independent of time. Absolute barrier layers are preferably 0.1 to 20 microns thick, and more preferably 1 to 3 microns thick. In other embodiments the barrier layer will provide a relative diffusion barrier that prevents detectable contact over a specified time interval and specified barrier thickness. In the case of a relative diffusion barrier, a suitable barrier thickness will be determined empirically taking into account the required time of the reaction. In general, the barrier thickness and time interval are directly proportional to one another. That is, reactions requiring longer time intervals will require thicker barrier layers.

Two molecules are said to "bind" if they associate non-covalently such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art. A first molecule is said to "specifically bind" relative to a second unrelated molecule if the ratio of the first molecule's binding constant to the second molecule's binding constant is greater than 2, and preferably greater than 5.

The term "complementary" refers to electronic topologic compatibility or matching together of interacting surfaces of a ligand molecule and its receptor, resulting in detectable binding using an appropriate assay technique. Thus, a receptor and its ligand can be described as complementary, as can the contact surface characteristics of a receptor and its ligand. Depending on the degree of complementarity of two ligands for a particular receptor as exhibited by their binding constants, one ligand may be said to more specifically bind relative to the other (see "bind" above). Two nucleobase polymers are said to be "complementary" if the polymers are able to pair (as in Watson-Crick base-pairing) with corresponding bases in a given nucleic acid molecule of interest. The term "exactly complementary" indicates that 100% of the nucleobases in a particular sequence are able to engage in base-pairing with corresponding bases of a nucleic acid molecule of interest. The term "substantially complementary" indicates that at least about 80% of the nucleobases in a particular sequence are able to engage in base-pairing with corresponding bases of a nucleic acid molecule of interest. The term "partially complementary" indicates that at least about 60% of the bases in a particular sequence are able to engage in base pairing with corresponding bases of a nucleic acid molecule of interest.

A "compound" is any molecule including, but not limited to, ligands, receptors, nucleobase polymers and peptides.

A photoresist layer is "continuous" if virtually no straight-line penetrable discontinuities or gaps are detectable in the coating. In other words, such discontinuities or gaps should make up less than 30% of the layer, as detected using, for example, standard microscopy, phase-contrast microscopy, and fluorescence microscopy. It will be apparent that a layer need be continuous only over regions where such coating is necessary for preparation or use of a porous coating. Any number of discontinuities and gaps can exist in other regions.

A layer of photoresist is said to "cover" molecules attached to a surface if the layer forms a continuous coating that is at least 0.1 micron thick.

"Curing" refers to the process of gelation and densification that occurs after evaporation of a coating solution (see "sol-gel" below). During curing, the number of oxane bonds increases, which in turn increases the strength that metal oxide particles have between one another and the substrate. Curing may be accomplished by heating at high temperatures for short periods, or low temperatures for long periods. High temperatures are limited to those below the sintering temperature where individual particles melt and the porosity of a coating is reduced to zero. The degree of oxane bonding during any point of the curing process may be tested and monitored using differential thermal analysis, thermogravimetric analysis, and density measurements (see Villegas and Navarro, *J Material Sci.* 23:2142, 1988). In general, curing of a porous coating should be performed at a temperature and for time sufficient to detectably increase the strength (ie., the stable attachment) of the porous coating, using methods as described above, and preferably the coating strength is increased to a level desired for subsequent process steps.

Exposure of a photoresist to a "developer" may refer to any treatment that dissolves an irradiated portion of a positive photoresist or an unirradiated portion of a negative photoresist, permitting selective removal of the dissolved regions. A developer may be a liquid or gas composition. Certain preferred developers comprise a non-aqueous mixture of solvents containing various ratios of ketone, amino, hydroxyl and amide moieties. Alternatively, a developer may be irradiation. A photoresist is said to be exposed to developer if a developer composition is contacted with the photoresist, or if irradiation is targeted to the photoresist, such that the photoresist is substantially removed in a specific region.

A "discrete known region" is a localized area of a surface on which a substantially pure group of compounds is, was, or is intended to be attached. Such regions do not overlap. A discrete known region may have any convenient shape including circular, rectangular, elliptical, etc., and may be of any size, such as 0.25 to $10^6$ square microns.

An "enzyme-cleavable moiety" is a portion of a molecule that is cleaved by exposure to a particular enzyme.

A solvent is said to be "evaporated" if less than 5% of the original solvent remains in the liquid state.

"Extended polymer" refers to the formation of a polymer by sol-gel (see "sol-gel" below). The progress of polymerization may be monitored by measuring, for example, the hydrodynamic radius by quasi-elastic light scattering, gas adsorption-desorption on sol-gel-coated surface acoustic wave (SAW) sensors, time dependent changes during NMR spectroscopy (e.g., $^{29}Si$), and monitoring the $H_2O$-content of the reacting system using IR-spectroscopy [see Brinker et al., *Thin Solid Films* (1991) 201:97; Daniels et al., Mat. Res. Soc. Symp. Proc. (1996) 435:215 and Schmidt et al., J. Non-Cryst. Solids (1982) 48:65]. Other methods for monitoring the progress of polymerization will be apparent to those of skill in the art. An extended polymer according to the present invention will have an average hydrodynamic radius greater than 2 nm, more preferably greater than 8 nm, and most preferably greater than 16 nm.

A "fortifying solution" is a solution of a polymeric binder that may be applied to a porous coating during preparation to yield a "fortifying layer" on the surface of the porous coating (see description of polymeric binder in "gelled network" below). The fortifying layer is typically applied before curing of the porous coating, and provides enhanced anchoring of the porous coating to the substrate. Enhanced anchoring may be assessed by an increase in the 180° peelback value using a modification of ASTM Test Method D3330 as described above for "adhesive layer " In a preferred embodiment, the fortifying layer comprises substantially hydrolyzed tetraethyoxysilane. The weight ratio of metal oxide particles to the fortifying layer plus other polymeric binder ranges from 1 to 1000.

"Full thickness volume" refers to the volume of a coating region as defined by the boundaries of the surface plane, the base plane (i.e., the plane of the coating in contact with the substrate surface or the surface of an adhesive layer), and the region. For example, a rectangular region of dimensions 1 and w on a coating of thickness t will have a full thickness volume of 1×w×t. A circular region of radius r will have a full thickness volume of $^1r^2t$ on the same coating.

"Gelled network" refers to an aggregation of particles linked together to form a porous three-dimensional network. Particles may be linked covalently or noncovalently through the use of a polymeric binder. Alternatively, particles may be linked covalently or noncovalently without the use of a binder, through interactions of chemical groups on the surface of the particles. Covalent interactions between polymeric binders or surface groups include the formation of, for example, oxane bonds (e.g., —O—Si—O—, —O-Ti-O—, —O—Al—O—, —O—B—O—, —O—Zr—O—, —O—Er—O—, —O—Cr—O— —O—Ga—O—, —O—Ge—O—, O—Hf—O—, —O—Fe—O—, —O—Ca—O—, —O—Cr—O—, —O—La—O—, —O—Mg—O—, —O—Nb—O—, —O—K—O—, —O—Pr—O—, —O—Sm—O—, —Na—O—, —O—Ta—O—, —O—Te—O—, —O—Tl—O—, —O—Sn—O—, —O—W—O—, —O—V—O—, —O—Y—O—, and —O—Zn—O—), linkages between an epoxide (e.g., glycidoxypropyltrimethoxysilane) and a polyamine (e.g., triethylene tetramine), and photoinduced linkages using, for example, a bis-azide. Noncovalent interactions that may be employed in polymeric binders or surface groups include, for example, electrostatic interactions, hydrogen bonding, metal coordination, and Van der Waals interactions. In some embodiments, particles will be linked by a mixture of covalent and noncovalent interactions. The extent of linking sufficient to constitute a "gelled network" will be such that less than 20%, and more preferably less than 5%, of the network is lost after contact with any process agent (e.g., irradiation, photoresist, developers, strippers and reagents). Accordingly, the extent of linking required will depend on the exact nature of the process agents. For example, photoresists that exhibit higher degrees of swelling will require gelled networks with higher degrees of linking so as to balance the forces of swelling and prevent physical disruption of the gelled network. The percent loss of the network after contact with process agents can be readily assessed using nitrogen adsorption isotherms and the Brunauer-Emmett-Teller (BET) method. The BET method allows the surface area of the gelled network to be accurately measured, and the percent change in surface area after contact with a process agent will be equivalent to the percent loss of the gelled network. Other methods for assessing the percent loss of the gelled network after contact with process agents will be apparent to one of ordinary skill in the art.

"Hybridization" refers to the base-pairing or aggregation of one nucleobase polymer to another nucleobase polymer via complementary regions. The polymers may be, for example, DNA, PNA, morpholino-based nucleobase polymers and/or other nucleobase polymers. Such base-pairing or aggregation should be detectable using standard assays (e.g., detection of a marker linked to one nucleobase polymer). Whether or not a particular nucleobase polymer remains base-paired or aggregated with a target nucleobase polymer depends on the degree of complementarity, the length of the aggregated elements, and the stringency of the binding conditions. At a higher stringency, hybridization requires a higher degree of complementarity or length.

"Hydrolyzed" refers to the lysis of water to split a chemical bond. For example, a metal alkoxide may be partially hydrolyzed (i.e., from 10% to 50% of hydrolyzable bonds hydrolyzed) or substantially hydrolyzed (i.e., greater than 50% of hydrolyzable bonds hydrolyzed). For example, 1 equivalent of water will hydrolyze 2 equivalents of hydrolyzable bonds in tetraethoxysilane resulting in a metal alkoxide that is partially hydrolyzed. This is consequence of the 1 equivalent of water hydrolyzing 1 equivalent of hydrolyzable bonds that generate 1 equivalent of free silanols. The 1 equivalent of free silanols in turn condense and release water, which goes on to hydrolyze the remaining 1 equivalent of hydrolyzable bonds for a total of 2 equivalents of hydrolyzable bonds hydrolyzed.

"Irradiation" refers to the application of radiation to a target. The amount of irradiation depends on the desired result of the irradiation. In general, irradiation is sufficient to achieve a desired chemical modification on an irradiated molecule. For example, irradiation of a positive photoresist layer is sufficient to permit substantial removal of photoresist from irradiated regions.

A "label" or "marker" is a modification of a compound (e.g., a ligand or receptor) that enables the user to specifically detect the labeled compound in the presence of unlabeled compounds. For example, one or more atoms within the compound may be replaced with radioactive isotopes. Alternatively, labels may provide antigenic determinants, nucleic acids available for hybridization, altered fluorescence-polarization or altered light-scattering. Still other markers include those that are chromogenic, fluorescent, chemiluminescent or electrochemically detectable. Other methods available to label a ligand or receptor will be readily apparent to those skilled in the art.

A "ligand," as used in this specification, is any molecule that is a candidate for specific binding by a particular receptor. It will be understood that many ligands will not specifically bind their intended receptor. For example, the majority of ligands in a drug analogue array will not be expected to bind their target receptor specifically. Further, the term "ligand" is not limited to molecules having any particular biological function. Ligands may be considered to be members of the larger generic group termed "compounds," which also includes molecules that are not candidates for specific recognition by receptors. Ligands may be naturally-occurring or man-made molecules, and they can be employed in their unaltered state or as aggregates with other species. Ligands may be attached (covalently or non-covalently) to a surface, either directly or via other molecules, such as linkers and/or spacers. Ligands may covalently or non-covalently modify a given receptor after binding the receptor. Such modifications include labeling, altering conformation, cleaving, covalently binding and intercalation. A ligand that is capable of modifying a target receptor in such a manner is said to comprise a "target receptor modifying group." Examples of ligands include, but are not restricted to, agonists and antagonists for cell membrane receptors, toxins and venoms, viral epitopes, hormones, antibodies, cell membrane receptors, monoclonal antibodies, antisera reactive to specific antigenic determinants, enzymes, drugs, drug analogues, polynucleotides, nucleic acid, catalytic nucleic acids, peptides, catalytic peptides, peptide nucleic acids, morpholino-based nucleobase polymers, other nucleobase polymers, cofactors, lectins, sugars, polysaccharides, cells, cellular membranes and organelles.

A "ligand-array" is a two dimensional matrix of ligands attached to a surface.

"Ligand-receptor binding" refers to specific, detectable binding between a ligand and receptor through molecular recognition.

A "ligand-receptor pair" is a complex formed when a ligand and receptor bind through molecular recognition.

"Mask" refers to a substantially transparent support material with substantially opaque regions in a precise pattern where it is desired that light be blocked when one side of the mask is illuminated. In some embodiments the substantially opaque regions are derived through a photographic process using a photoplotting device (e.g., as in masks commonly used in printed circuit board manufacturing). In other embodiments the mask is derived from a substantially transparent support material coated with a substantially opaque material which is photoablated by a narrowly focused laser producing precisely defined transparent regions (e.g., chrome on glass masks). The differential between the intensity of light transmitted by substantially transparent and substantially opaque regions as a percentage of the intensity of light transmitted by substantially transparent regions should be greater than 75%, more preferably greater than 90%, and most preferably greater than 99%.

"Nucleic acid molecules" (or "nucleic acids") are polymers of nucleotides (i.e., compounds formed of phosphoric acid ($H_3PO_4$), a sugar, and a purine or pyrimidine base). Such polymers may be of any length, and include DNA and RNA molecules. Relatively short nucleic acid molecules (i.e., containing fewer than about 200 nucleotides) may be referred to as "oligonucleotides." Nucleic acid molecules are typically susceptible to degradation by nucleases.

A "nucleobase" is a nitrogenous heterocyclic group typically found in nucleic acids (such as the purine bases adenine and guanine, or the pyrimidine bases cytosine, thymine and uracil), or an analog of such a group. Analogs include, for example, purine bases in which the ring substituents are other than those found in adenine or guanine, or pyrimidine bases in which the ring substituents are other than those found in uracil, thymine and cytosine. A number of analogs of nucleobases are well known in the art; many of which have been tested as chemotherapeutic agents. Some of these are described herein; see also, e.g., *Beilstein's Handbuch der Organischen Chemie* (Springer Verlag, Berlin), and Chemical Abstracts, which provide references to publications describing the properties and preparation of such compounds.

A "nucleobase polymer" is a polymer of nucleobases linked to a backbone. The backbone may be naturally occurring (as in a nucleic acid molecule) or may be non-naturally-occurring. Nucleobase polymers with non-naturally-occurring backbones are preferably resistant to degradative enzymes. Representative examples include peptide nucleic acids (see Buchardt et al., PCT WO 92/20702 and Buchardt et al., U.S. Pat. No. 5,719,262), morpholino-based nucleobase polymers (see Summerton and Weller, U.S. Pat. No. 5,698,685; Summerton et al., U.S. Pat. No. 5,378,841 and Summerton and Weller, U.S. Pat. No. 5,185, 444), peptide-base nucleic acid mimics or PENAMs (see Shah et al., U.S. Pat. No. 5,698,685), and polynucleosides with linkages comprising carbamate (see Stirchak and Summerton, *J. Org. Chem.* 52:4202, 1987), amide (see Lebreton et al., *Synlett. February* 1994:137), methylhydroxylamine (see Vasseur et al., *J. Am. Chem. Soc.* 114:4006, 1992), 3'-thioformacetal (see Jones et al., *J. Org. Chem.* 58:2983, 1993), sulfamate (see Huie and Trainor, U.S. Pat. No. 5,470,967) and others (see Swaminathan et al., U.S. Pat. No. 5,817,781 and Freier and Altmann, *Nucl. Acids Res.* 25:4429, 1997, and references cited therein).

"Particles" are discrete objects that when packed together yield a porosity ranging from 0.15 to 0.99, where porosity is defined as the fraction of the volume of the packed objects that is void space. Particles may have any shape, and may be, for example, spheres, cubes or irregularly shaped objects. Preferably the objects are substantially spherical (i.e., an object whose surface points are at a distance r±0.2 r from the object's center of mass), with a primary particle size ranging from 1 to 1000 Å. The choice of composition of the particles is such that the porosity is decreased less than 20%, and more preferably less than 5%, after contact with any agent to be employed, including irradiation, photoresist, developers, strippers and reagents. The percent decrease in porosity after contact with such agents can be readily assessed using nitrogen adsorption isotherms and the Brunauer-Emmett-Teller (BET) method. Other methods for assessing the percent loss in porosity after contact with process agents will be apparent to one of ordinary skill in the art.

A "peptide nucleic acid" (PNA) is a molecule comprising repeating units of N-(2-aminoethyl)-glycine linked by amide bonds (see Buchardt et al., PCT WO 92/20702). Unlike the natural DNA backbone, no deoxyribose or phosphate groups are present. The bases are attached to the backbone by methylene carbonyl linkages.

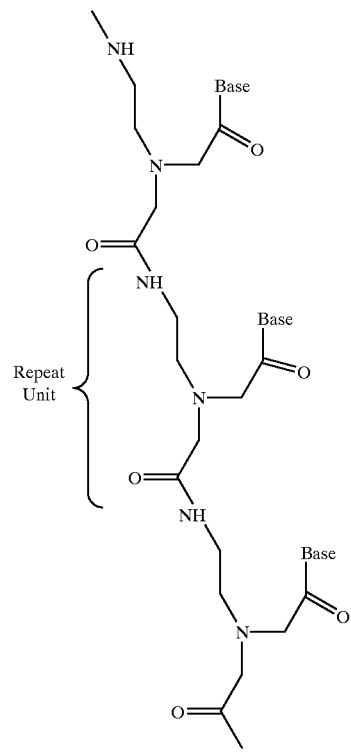

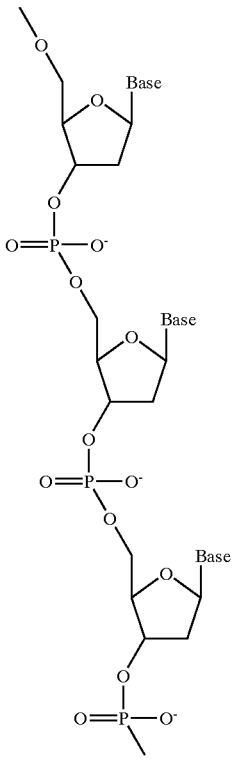

In this specification, PNA sequences are written using the single-letter designation of the attached base just as DNA sequences are written. PNA sequences are distinguished from DNA sequences by an "NH₂" group at what would be the 5' end of a DNA sequence. For example, in this specification AGGTC-5' is a DNA sequence, while AGGTC-NH₂ is a PNA sequence. Certain preferred peptide nucleic acid polymers comprise a repeating unit of the form:

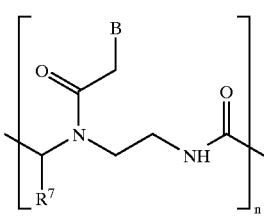

wherein each B is independently selected from the group consisting of nucleobases; each $R^7$ is independently selected from the group consisting of hydrogen, $C_{1-C8}$ alkylamines and spacers, and each n is an independently selected integer ranging from 1 to 100.

A "peptide nucleic acid mimic" (PENAM) is a nucleobase polymer that comprises a repeating unit of the form:

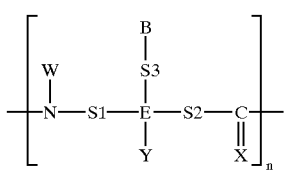

wherein each is E is independently selected from the group consisting of carbon and nitrogen; each W is independently selected from the group consisting of hydrogen and spacers; each Y is independently selected from the group consisting of hydrogen and spacers, in repeating units wherein E is carbon; each Y is a lone pair of electrons, in repeating units wherein E is nitrogen; each S1 is optional, and if present is an independently selected first spacer; each S2 is optional, and if present is an independently selected second spacer; each S3 is optional, and if present is an independently selected third spacer; each X is independently selected from the group consisting of oxygen and sulfur; each B is independently selected from the group consisting of nucleobases; N is nitrogen; and each n is an independently selected integer ranging from 1 to 100.

A "photocleavable moiety" is a portion of a molecule that is cleaved upon exposure to light of a particular wavelength and intensity.

"Photoresist" refers to a material that, upon irradiation, sustains a chemical reaction that allows irradiated and non-irradiated regions to be separated from one another. Although the separation may be simultaneous with the irradiation step (e.g., in laser ablation), it often requires an additional process step or steps (e.g., exposure to a developer). The chemical reaction may involve the formation or breakage of chemical bonds with such bond changes occurring in either an intramolecular or intermolecular fashion. In most applications, a photoresist is applied to a flat surface as a relatively thin liquid layer and evaporated. A "negative photoresist" refers to a photoresist that leaves photoresist on the surface in irradiated regions, while a "positive photoresist" refers to a photoresist that leaves photoresist on the surface in regions that were not irradiated. Certain positive photoresists comprise a base soluble component with phenolic hydroxyl groups. Within such photoresists, "base soluble" refers to a component with groups having a pKa of about 10 that are solubilized by aqueous solutions having a pH greater than about 10, and more preferably greater than about 11.

"Planarization" refers to a leveling process in a liquid layer applied to a substrate surface such that the free surface of the liquid layer is substantially planar despite irregular topography on the substrate surface.

A "polymer" is a molecule in which individual molecular units are repetitively linked by covalent bonds. A polymer of a hydrolyzed metal alkoxide comprises multiple hydrolyzed metal alkoxide molecules covalently linked to one another through oxane bonds.

A "polymerase" is an enzyme that catalyzes the assembly of ribonucleotides into RNA, or deoxyribonucleotides into DNA. "Polymerase chain reaction" (PCR) refers to a process for the exponential amplification of a specific DNA fragment using two oligonucleotide primers that hybridize to opposite strands and flank a region of interest in a target DNA (see Mullis, U.S. Pat. No. 4,683,202 and Mullis et al., U.S. Pat. No. 4,683,195). The process consists of a series of repetitive cycles involving template denaturation, primer annealing, and the extension of annealed primers by Taq DNA polymerase or other thermostable polymerase.

A coating is said to be "porous" if it contains void regions ranging from 1 to 1500 nm in diameter resulting in porosities ranging from 0.15 to 0.99, where porosity is defined as the fraction of the coating volume which has pores. For example, a porous coating of inorganic metal oxide particles contains void regions between inorganic metal oxide particles created by the packing of the metal oxide particles. Such a porous coating preferably has a "substantially uniform thickness" (i.e., the thickness of the coating varies by no more than 30% over the entire coated area). The average pore size preferably ranges from 10 to 1000 nm, and may be readily determined by nitrogen adsorption isotherms and the Brunauer-Emmett-Teller (BET) method according to methods well known in the art. Within certain embodiments, the average pore size of a porous coating substantially approximates the particle size (i.e., the average pore size is p+0.9p, wherein p is the average particle size).

"Primary particle size" refers to the average size of unagglomerated single particles of inorganic metal oxide.

A "primer" is a nucleic acid or other nucleobase polymer designed to be sufficiently complementary to a target sequence in a denatured nucleic acid (in relation to its length) to be bound under selected stringency conditions so as to serve as a ligand for a polymerase. A primer should bind sufficiently to permit detection of the target sequence in a PCR assay.

A "probe" is a nucleic acid or other nucleobase polymer designed to be sufficiently complementary to a target sequence (in relation to its length) to be bound detectably under selected stringency conditions. A probe is typically labeled with a marker, such as a fluorescent moiety.

"Radiation" refers to energy which may be selectively applied, including energy having a wavelength of between $10^{-14}$ and $10^4$ meters. Radiation includes electrons, x-rays and particles from radioisotopic decay, as well as light (e.g., visible, ultraviolet or infrared).

A "reagent" is any compound that undergoes a chemical reaction with a molecule attached to a surface of an array. For example, a reagent may form a covalent bond with an attached molecule, permitting the synthesis of attached organic compounds using a series of reactions with known reagents.

"Reagent history" refers to a predefined sequence of reagents contacted with a predefined region of a solid-support. In most cases, the composition of a compound predicted by the reagent history and the actual predominant compound composition at a predefined region will be the same. However, the predicted composition will not accurately reflect the actual composition of the region in some embodiments. For example, when a reagent sequence comprises chemical reactions whose characteristics are not well defined, the predominant composition of a predefined region may not be predictable. In contrast, describing this predefined region by its reagent history uniquely defines the composition, which can be reproduced by the reagent history. Knowing the predominant composition of each array element is not always necessary in many applications. For example, a small-molecule array may contain an active drug candidate defined accurately only by its reagent history. Using this information, the candidate can be resynthesized on a large-scale, and the composition of the active component identified even if it is a minority fraction.

A "receptor" is a molecule that specifically binds a given ligand. Receptors may be naturally-occurring or man-made molecules, and can be employed in their unaltered state or as aggregates with other species. Receptors may covalently or non-covalently modify a given ligand after binding the ligand. Such modifications include labeling, altering conformation, cleaving, covalently binding and intercalation. A receptor that is capable of modifying a target ligand in such a manner is said to comprise a "target ligand modifying group." Examples of receptors include, but are not limited to, antibodies, cell membrane receptors, monoclonal antibodies, antisera reactive to specific antigenic determinants, enzymes, drugs, polynucleotides, nucleic acid, catalytic nucleic acids, peptides, catalytic peptides, peptide nucleic acids, morpholino-based nucleobase polymers, other nucleobase polymers, cofactors, lectins, sugars, polysaccharides, cells, cellular membranes and organelles.

Compounds are "resistant to degradation by degradative enzymes" if less than 50% of the compounds are degraded after 10 minutes of contact with a degradative enzyme at a concentration equal to the $K_m$ of the enzyme, and under conditions where the enzyme activity is known to be optimal (e.g., at an optimal temperature and salt concentration, and in the presence of optimal cofactors, prosthetic groups and coenzymes). Optimal conditions for a particular degradative enzyme will be readily apparent to those of ordinary skill in the art. The term "degraded" as used in this definition refers to one or more chemical alterations by the degradative enzyme that reduces the molecular weight of a compound. Degradative enzymes, within the context of the present invention, are naturally occurring nucleases and proteases. Representative degradative enzymes include, for example, specific and non-specific ribonucleases, deoxyribonucleases, exonucleases, and endonucleases, as well as specific and non-specific endoproteases and exoproteases. Numerous methods are available to those of skill in the art to test if a compound is resistant to degradation by degradative enzymes as defined above. For example, compounds may be contacted with degradative enzymes and the mixture subsequently subjected to an analytic procedure to determine if the molecular weight of greater than 50% of the compounds has been reduced. Such analytic procedures are numerous and will depend on the particular compound. They include, but are not limited to, high-pressure liquid chromatography (i.e., HPLC), gel electrophoresis, NMR spectroscopy, and IR spectroscopy. Other analytic procedures will be readily apparent to those skilled in the art. For example, HPLC may be used to detect the percent of a nucleobase polymer degraded by a non-specific single-strand deoxyribonuclease by dividing the integrated UV absorption of all chromatographic peaks other than the peak of the parent nucleobase polymer by the integrated UV absorption of all chromatographic peaks. Using such an analytic method, much more than 50% of an oligodeoxyribonucleotide will be degraded after 10 minutes of incubation with a non-specific single-strand deoxyribonuclease at a concentration equal to the enzyme's $K_m$. In contrast, nucleobase polymers possessing non-natural backbones will be degraded much less than 50% under identical conditions. As a practical matter, it is usually possible to identify a compound as resistant to a particular class of degradative enzymes by simply inspecting the chemical structure of the compound and determining if the structure differs appreciably from the natural substrate of the degradative enzyme. In particular, nucleobase polymers will be resistant to the general class of degradative enzymes known as nucleases if their backbone contains linkages other than the native phosphodiester linkage of nucleic acids. Similarly, nucleobase polymers will be resistant to the general class of degradative enzymes known as proteases if their backbone contains peptidic linkages comprising spacers or side-chains not found in proteins or peptides.

"Sol" refers to an intermediate in the "sol-gel" process. A sol is characterized by colloid-like oligomers formed from a chemical precursor.

"Sol-gel" refers to a method for preparing specialty metal oxide glasses and ceramics by hydrolyzing a chemical precursor or mixture of chemical precursors that pass sequentially through a solution (sol) state and a gel state before being dehydrated to a glass or ceramic. Preparation of metal oxide glasses by the sol-gel route proceeds through four basic steps: (1) partial hydrolysis of precursors to form reactive monomers; (2) polycondensation of these monomers to form colloid-like oligomers (sol formation); (3) additional hydrolysis to promote polymerization and cross-linking leading to a three-dimensional matrix (gel formation); and (4) further densification and cross-linking by drying and other dehydration methods. Although steps (1) through (3) are presented sequentially, after step (1) these reactions occur simultaneously to varying degrees. The chemical precursors are typically metal alkoxides, but may also include organo-metal alkoxides. A very common precursor is tetraethoxysilane, which proceeds through the sol-gel process according to the steps shown below:

(1) Monomer formation;

$Si(OC_2H_5)_4 + H_2O \rightarrow (OC_2H_5)_3SiOH + C_2H_5OH$ (2) Sol formation;

$n+1\ (OC_2H_5)_3SiOH \rightarrow (C_2H_5O)_3Si(OSi(OC_2H_5)_2)_nOH + n\ C_2H_5OH$ (3) Gelation; and

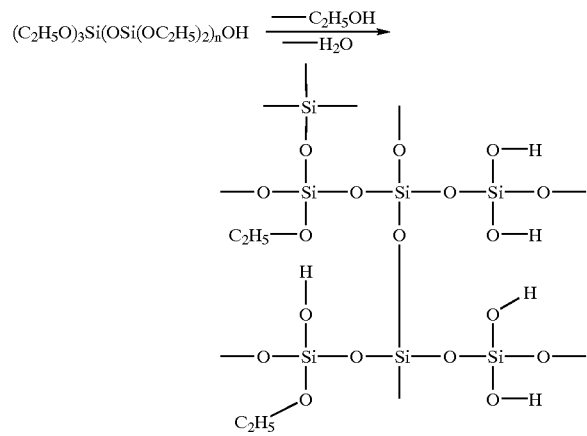

(4) Densification

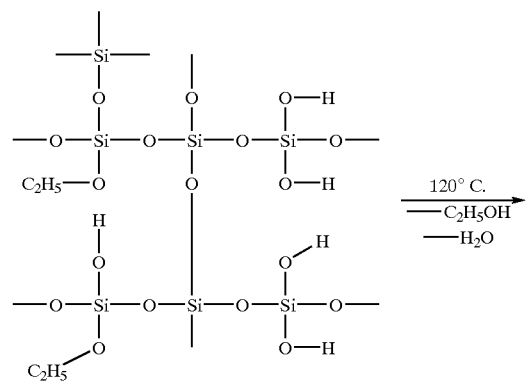

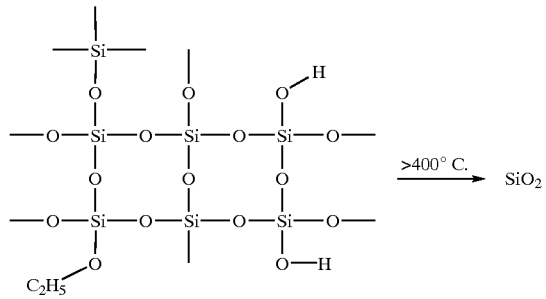

Within certain embodiments described herein, coating solutions are formed that comprise substantially stable sots. The remaining steps of gelation and densification occur rapidly upon evaporation of solvent from an applied liquid layer of the sol. Curing at less than 250° C. results in "partial densification," with the network remaining relatively open with free silanols and some organic moieties still present. While not a necessary step in the present invention, very high temperatures do achieve the maximum density of silicon dioxide.

"Solvent Resistance" refers to the ability of a polymeric film to maintain integrity and impermeability while in contact with a particular solvent. A film is "solvent resistant" if contact with a particular solvent does not result in detectable cracking or dehiscence, or significant film dissolution, in the region where it is desired to place an array of compounds. Detectable cracks or dehiscence means cracks or dehiscence detected visually, or by light or phase-contrast microscopy. Significant film dissolution is defined as greater than 50% loss of film thickness after contacting the film with a particular solvent for a particular time period, and may be tested using profilometry or interferometry. It will be apparent that dehiscence, cracks, or loss of more than 50% of film thickness may be tolerated over regions where it is not desired to place an array of compounds. In some embodiments, the solvent resistance of a particular polymeric composition will be a function of film thickness. For instance, films which exceed a particular critical thickness will often crack in a particular solvent, presumably from solvent-induced stresses in the film that exceed the adhesive forces between the film and the substrate.

"Solution" refers to dispersions and suspensions of finely divided particles of ultramicroscopic size in a liquid medium, as well as the conventional definition of the term "solution." A "spacer" is a molecule that spaces an attached compound from a substrate. A spacer is relatively small, containing a backbone of 1–10 atoms (not counting hydrogen atoms), preferably selected from carbon, nitrogen, oxygen, and sulfur. Typically, such spacers comprise substituted or unsubstituted alkyl, alkenyl, alkenyl groups. However, spacers can also comprise for example: carbonyl (C=O), thiocarbonyl (C=S), amine (NH), substituted amine (NR), amide (C(=O)NH), substituted amide (C(=O)NR), carbamate (NHC(=O)O), urea (NHC(=O)NH), thioamide (C(=S)NH), substituted thioamide (C(=S)NR), hydrazine (NH—NH), substituted hydrazine (N(R)—N(R)), ether (C—O—C), thioether (C—S—C), disulfide (S—S), sulphone (S(=O)) and/or sulphoxide ($SO_2$) groups. A spacer can also be substituted with one or more small chemical groups, for example, small chain alk(ane, ene, yne)s, hydroxyl, alkoxyl, ketone, aldehyde, thiol, amino and/or halogen groups. A particular compound in an array may have multiple spacers, which may, but need not, be identical to one another. A spacer may also, or alternatively, be attached to one or more linkers.

"Stringency" refers to the combination of conditions by which complexes of aggregated nucleobase polymers (e.g., DNA:DNA, PNA:DNA or PNA:PNA) dissociate into individual component monomers. Common conditions used to influence stringency include pH, temperature, and salt concentration. See "$T_m$" below.

"Stripping" refers to the substantial removal of photoresist by strippers. Strippers are liquid chemical media used to remove photoresists after processing is finished. The exact composition depends on the composition of the photoresist.

"Substantial removal" of a photoresist from underlying molecules or porous coating means that photoresist is sufficiently removed to permit a desired reaction between underlying molecules or porous coating and a reagent. Such a reaction should have a yield that is at least 50%, and more preferably at least 90% of the yield observed for similar molecules that have not previously been coated with photoresist. Reaction yields may be readily determined with and without photoresist using standard techniques appropriate for the reaction of interest. Such techniques are well known to those in the art and include, for example, analysis of released protecting groups during synthesis as in the analysis of released trityl groups during solid-phase DNA synthesis, or analysis of free nucleophiles produced during synthesis as in the analysis of free amino groups during peptide synthesis using the ninhydrin reaction. Other methods include quantification of the final product while still attached to the substrate surface using, for instance, a surface acoustic wave sensor, or binding with a fluorescently labeled receptor (e.g., nucleobase polymer or antibody) and quantifying the fluorescent signals. Still other methods include releasing the final product from the substrate surface and quantifying it using high-pressure liquid chromatography, labeling with radioisotopes, and other methods familiar to those skilled in the art.

A compound is "substantially pure" if, within a discrete known region, the ligand is present at a concentration that is sufficient to permit the detection of distinguishing characteristics of the ligand. Such detection may be based, for example, on biological activity or function, which may be measured by way of binding with a selected ligand or receptor. Other characteristics that can be measured include, for example, color, light absorbance, light transmission, fluorescence, phosphorescence, molecular weight, charge, density, melting point, chromatographic mobility, turbidity in a solution (i.e., nephelometry), electrophoretic mobility, mass spectrum, ultraviolet spectrum, infrared spectrum, nuclear magnetic resonance spectrum, elemental composition, and x-ray diffraction. Preferably, a substantially pure ligand is present in a region at a level that is greater than 5%, 10%, 50%, 70% or 90% of the total compounds with the region.

"Surface density" refers to the number of molecules contained in a three-dimensional volume projected on a two-dimensional space. For example, 1000 molecules in a volume with dimensions x=10 $\mu$m, y=10 $\mu$m and z=1 $\mu$m would have a surface density in the x-y space of 1000 molecules per 100 $\mu m^2$ or 10 molecules/$\mu m^2$. The surface density in the x-z space would be 1000 molecules per 10 $\mu m^2$ or 100 molecules/$\mu m^2$. If z=3 $\mu$m, the surface density in the x-y space would be 300 molecules/$\mu m^2$. When discussing ligand-arrays, the molecules are ligands and the projected space is taken to be equivalent to the largest planar component of the substrate.

A "substantially uniform layer" is a layer that varies in thickness by no more than 30% over a region of interest.

"$T_m$" refers to the temperature at which two complementary polymers dissociate into individual nucleobase components. An approximate value of $T_m$ for a DNA duplex in degrees centigrade is given by the formula:

$$T_m = 16.6\log[M] + 0.41[P_{gc}] + 81.5 - P_m - B/L$$

where M is the molar concentration of $Na^+$ to a maximum of 0.5, $P_{gc}$ is the percent of G or C bases in the oligonucleotide between 30% and 70%, $P_m$, is the percent mismatch, B is 675 for oligonucleotides less than 100 bases, and L is the probe length in bases. For a PNA:DNA heteroduplex in 100 mM NaCl, the $T^m$ is approximately 1° C. higher per base pair than the corresponding DNA duplex.

Coated Articles

The present invention provides articles comprising a continuous porous coating to which one or more compounds may be attached. In general, such porous coatings have a substantially uniform thickness, and comprise a gelled network of particles. The porous coatings may also be patterned using a photoresist and photolithographic methods in a fashion which allows exemplary reproducibility and control over the dimensional features of the patterned porous coating.

The present invention has a variety of uses including, for example, applications which require the synthesis of a large number of known compounds at known locations on a solid support, each in quantities sufficient for diagnostics or pharmacologic screening. Such applications exist in the field of array manufacturing where microfabrication and solid-phase synthetic methods presently result in only low ligand surface densities. The instant invention overcomes the limitations associated with imaging ligand-receptor binding on low ligand surface densities by providing a support with increased surface area for ligand attachment. Using a porous coating provided herein, imaging may be accomplished rapidly and with less costly equipment. The invention also eliminates the need for other equipment, such as a flow-through apparatus to contact reagents or receptors with arrayed ligands.

The increased surface density of drug candidates on a porous array, as described herein, permits the performance of functional assays using a single array element. Furthermore, drug candidates that have only weak to moderate binding may be identified during screening because the increased surface density ultimately provides a higher assay concentration of the candidate. Similarly, arrays of small-molecules bound on the porous support of the present invention can be used to screen for other activities including pesticide or herbicide activities.

Briefly, articles comprising porous coatings as provided herein may be prepared by: (a) applying to a substrate a substantially uniform layer of a solution comprising particles dispersed in a volatile liquid; (b) evaporating the volatile liquid from the layer, forming a gelled network of particles on the substrate; and (c) attaching two or more compounds to discrete known regions of the porous coating. Various modifications may be made to this method, including using a polymer-particle composite to form the gelled network, photopatterning the porous coating and enhancing porous coating strength through the use of a fortifying layer and/or a curing step. Each of these steps is described in greater detail below.

A. Substrate Selection and Preparation

Nearly any conceivable substrate may be employed, including substrates that are biological, nonbiological, organic, inorganic or a combination of any of these. The substrate may have any convenient shape, such as a disc, square, sphere, circle, or any other suitable shape, and may be formed, for example, as a particle, strand, precipitate, gel, sheet, tube, sphere, container, capillary, pad, slice, film, plate or slide. The substrate should form a rigid support on which to support the porous coatings described herein, and is preferably flat, although it may have a variety of alternative surface configurations, including raised and/or depressed regions. The substrate may be prepared from essentially any material. For instance, a substrate may comprise functionalized glass, Si, Ge, GaAs, GaP, $SiO_2$, $SIN_4$, modified silicon, photoresist, biolayers, silane layers or any one of a wide variety of polymers such as polytetrafluoroethylene, polyvinylidenedifluoride, polystyrene, polycarbonate, polyethylene, polypropylene, nylon, polyethylene terephthalate or combinations thereof. Other substrate materials will be readily apparent to those of skill in the art. In a preferred embodiment the substrate is flat glass or single-crystal silicon.

The surface of a substrate may, but need not, be composed of the same material as the substrate. Surface materials include, but are not limited to, polymers, plastics, resins, polysaccharides, alumina, silica or silica-based materials, carbon, metals, inorganic glasses, membranes or any of the above-listed substrate materials. Preferably, the surface contains reactive groups, such as carboxyl, amino and/or hydroxyl groups. Most preferably, the surface will be optically transparent and will have surface Si—OH functionalities, such as are found on silica surfaces. Surfaces are also preferably rigid.

Optionally, a surface of a substrate may have an adhesive layer, which is stably attached to the substrate and promotes adhesion of the porous coating to the substrate. It will be apparent that any of a variety of adhesive layers may be used. In preferred embodiments, an adhesive layer comprises partially or substantially hydrolyzed monomers, oligomers, and/or extended polymers of a metal alkoxide or organo-metal alkoxide coupled to one another through "oxane" bonds (ie., "-M-O-M-"; condensation products of: -M-OH+OH-M-→-M-O-M-+$H_2O$, where M is a metal). For example, the adhesive layer may comprise one or more polymers of a hydrolyzed organo-metal alkoxide of the formula: $R_{n'M(OR)x}$, wherein M is selected from the group consisting of Si, Ti, Al, B, Zr, Er, Cr, Ga, Ge, Hf, Fe, Ca, Cr, La, Mg, Nb, K, Pr, Sm, Na, Ta, Te, Tl, Sn, W, V, Y and Zn; R' is a monovalent organic group containing between 1 and 12 carbon atoms, preferably having one or more groups selected from the group consisting of hydrogen, amine, hydroxyl, carboxyl, amide, thiol, sulfonic, or epoxide; R is hydrogen, an alkyl group or an aryl group and n and x are integers independently selected from the group consisting of 0, 1, 2, 3 and 4. A sol may be prepared from such a metal alkoxide by hydrolyzing and aging the metal alkoxide at an acidic pH, as described below. In a preferred embodiment, the adhesive layer comprises a polymer of hydrolyzed tetraethoxysilane (e.g., the layer may be a partially densified layer of partially or substantially hydrolyzed tetraethyoxysilane). The adhesive layer is of sufficient thickness to provide stable attachment between a porous coating and a substrate. In some embodiments the thickness of the adhesive layer is less than 0.001 $\mu$m, 0.01 $\mu$m, 0.1 $\mu$m, 1.0 $\mu$m, or 10.0 $\mu$m. Preferably, the thickness is between 0.002 and 2 $\mu$m, more preferably between 0.1 $\mu$m and 10.0 $\mu$m.

An adhesive layer may be formed on a substrate by applying a substantially uniform layer of an adhesive solution (comprising a metal oxide or organo-metal alkoxide polymer and a volatile solvent) to the surface of the substrate, and evaporating the volatile solvent. The solution may contain various solvents or mixtures of solvents, in which the partially or substantially hydrolyzed monomers and condensation products of the organo-metal alkoxide are soluble. For example, suitable solvents include ethylene glycol monomethyl ether, ethyl alcohol, methyl alcohol, butyl alcohol water and mixtures thereof, in such proportions as to give desirable evaporation characteristics. Preferred adhesive solutions comprise an aged sol of hydrolyzed tetraethoxysilane in a volatile solvent. One preferred sol comprises 1.5 volume percent tetraethoxysilane, in 0.45 volume percent water, 3 mM nitric acid, with the balance ethanol. A concentrated sol may be prepared by hydrolyzing 21.7 ml of tetraethoxysilane in 6.3 ml $H_2O$ and 0.7 ml 1N nitric acid, followed by aging at 4° C. for several days. The concentrated sol is clear and stable for several weeks at 4° C. An adhesive solution may be applied to a surface by any suitable technique, including dip-coating, spin-coating or microdispensing. In one embodiment, the concentrated sol described above is diluted 50-fold with ethanol, and applied to surface at an incline using a pipette.

After the adhesive solution is applied as a liquid layer, the solvent is allowed to evaporate, resulting in an adhesive layer. Evaporation may take place at any suitable temperature between 10° C. and 150° C., and most preferably at room temperature. Following evaporation, an adhesive layer may be cured to enhance adhesion. Curing may take place, for example, at a temperature that ranges from 20° C. to 250° C. for a period of time sufficient to establish an extensive network of oxane bonds. In general, about 15 minutes at 120° C. is sufficient. The final thickness of an adhesive layer may be controlled by altering the percent solids in the sol, molecular weight of the solids, viscosity, incline angle, withdrawal-rate in the case of dip-coating, or the spin speed in the case of spin-coating.

B. Formation of Gelled Network of Particles

As noted above, porous coatings as described herein comprise a gelled network of particles. Such a gelled network may generally be prepared by applying to the substrate a substantially uniform layer of a solution comprising suitable particles (and, optionally, a polymeric component) dispersed in a volatile liquid. Following application, the volatile liquid is evaporated, forming a porous coating that comprises a gelled network of particles.

There are a variety of particles that may be used to form a porous coating. Such particles may comprise, for example, one or more of: carbon, activated carbon, fluorinated carbon, styrenedivinylbenzene copolymers, polystyrene, zeolites, oxides of antimony and oxides of metals present within Group III and Group IV of the Periodic Table. The selection of the particle composition is dependent upon the ultimate balance of properties desired, and upon whether formation of the gelled network depends on interaction between particles (or, as described below, is facilitated through the use of a polymeric component). Particles may have any of a variety of sizes and shapes. Preferably, the particles have a primary particle size of less than 2000 Å, and more preferably less than 1000 Å and still more preferably less than 500 Å. In some embodiments, particles have a primary particle size less than 100 Å, 50 Å, 10 Å or 5 Å. Although in most embodiments, a porous coating will be prepared with metal oxide particles having a narrow size distribution, it may be desirable in some embodiments to use particles with a broad size distribution (e.g., by mixing particles of different primary particle sizes). The particles are preferably spherical, although other shapes are possible, including cubes and irregular shapes.

Within certain preferred embodiments, the particles are metal oxide particles. Metal oxide particles particularly suitable for use in preparing a porous coating are those in which the metal oxide particles are negatively charged. Such particles include, but are not limited to, particles comprising tin oxide ($SnO_2$), titania, antimony oxide ($Sb_2O_5$), silica, silicalite, fumed silica, alumina and alumina-coated silica as well as other metal oxides of Groups III and IV of the Periodic Table and mixtures thereof. Particularly preferred particles include silica and alumina-coated silica particles. In one embodiment, the metal oxide particles are spherical fumed-silica ($SiO_2$) particles with a primary particle size of 500 Å.

Certain particles are particularly suited for preparing porous coatings in the absence of a polymeric component. For example, porous coatings may be formed from strongly branched particles formed by sol-gel methods that bond to one another through oxane bonds (see Brinker et al., *Thin Solid Films* 201:97, 1991 and Brinker et al., in: *Ultrastructure Processing of Advanced Materials*, Wiley-Interscience, John Wiley and Sons, edited by Uhlmann and Ulrich, (1992), p. 211). Alternatively, porous coatings may be formed from both aged and unaged colloidal silica solutions directly (see Frye et al., in: *Better Ceramics Through Chemistry IV*, vol. 180, Mat. Res. Soc. Symp. Proc., edited by Brinker et al., (1990), p. 583; Frye et al., U.S. Pat. No. 5,224,972; Frye et al., U.S. Pat. No. 5,589,396, Cathro et al., *Solar Energy* 32:573, 1984 and Lange et al., U.S. Pat. No. 4,816,333).

Within certain embodiments, the gelled network further comprises a polymer suitable for forming a polymer-particle composite. Polymers of hydrolyzed metal alkoxides are preferred. Such polymers may be various condensation products (a small fraction, e.g., less than 20 weight percent, of the metal alkoxide may exist as monomer) of a hydrolyzed metal alkoxide of the formula $M(OR)_x$, where x may be 3 or 4; and R is hydrogen, an alkyl group or an aryl group (e.g., methyl, ethyl, n-propyl, isopropyl, n-butyl, isobutyl, tertiary butyl group, or mixtures thereof). The metal, M, may be Si, Ti, Al, B, Zr, Er, Cr, Ga, Ge, Hf, Fe, Ca, Cr, La, Mg, Nb, K, Pr, Sm, Na, Ta, Te, Tl, Sn, W, V, Y or Zn. In one embodiment, the metal alkoxide polymer comprises a partially densified layer of hydrolyzed tetraethyoxysilane. The ratio of metal oxide particles to metal alkoxide polymer should be in a range which adequately binds the particles together and to the adhesive surface, and provides a substantially uniform coating, but does not result in metal alkoxide polymer substantially filling the pore volume. In preferred embodiments, in which silica particles are employed, the weight ratio of silica particles to hydrolyzed metal alkoxide ranges from 1–1000:1, preferably 3–1000:1, and more preferably 40–350:1.

It will be apparent that other polymer-particle composites are possible. For example, in some embodiments porous coatings may be polymer-particle composites of metal oxide-hydroxide particles linked by cellulosic polymers (see Farooq et al., U.S. Pat. No. 5,686,602 and Desu et al., PCT WO 94/14088). Suitable cellulosic polymers include, for example, hydroxypropyl methylcellulose, methylcellulose, hydroxypropyl ethylcellulose and hydroxyethyl cellulose. The cellulosic polymers may be either left in the porous coating as a polymer cross-linked by metal ions, or removed by sintering. Another suitable polymer that may be sintered is polyimide (Desu et al., PCT WO 94/14088). In other embodiments the polymer-particle composite comprises alumina particles covalently linked by a photosensitized polyethyleneimine, or colloidal silica particles linked by an epoxide (e.g., glycidoxypropyltrimethoxysilane) and a polyamine (e.g., triethylene tetramine) (see Pu et al., *J. Imaging Sci.* 33:177, 1989 and Chu et al., *Mat. Res. Soc. Symp. Proc.* 435:221, 1996). In still other embodiments the polymer-particle composite comprises particles noncovalently linked by polytetrafluoroethylene wherein the particles may be comprised of finely divided carbon, activated carbon, fluorinated carbon, alumina, silica, silicalite (described by Grose et al., U.S. Pat. No. 4,061,724), fumed silica, styrenedivinylbenzene copolymers, polystyrene, zeolites, and various metal oxide particles (see Suppiah, U.S. Pat. No. 5,120,600).

It should be noted that organo-metal alkoxides such as APES and HAPES, do not function as substitutes for metal alkoxides when the particles are fumed silica. Hydrolysis of APES and HAPES results in the formation of organosilsesquioxanes, which form considerably less extended polymers than metal alkoxides due in part to stabilization of silanols through internal hydrogen bonding with the amino moiety. The lower degree of APES and HAPES polymerization may explain their ineffectiveness.

For preparation of a porous coating, the particles (and polymeric component, if desired) are combined with a suitable solvent to form a solution. It will be apparent that such a solution may be a dispersion or suspension of finely divided particles. The coating solution may contain various solvents or mixtures thereof in which the various polymer components are soluble, and in which the particles may be effectively dispersed or suspended. Suitable solvents will be apparent to those of ordinary skill in the art. For example, solvents may be used such as ethylene glycol monomethyl ether, 3-pentanone, ethyl alcohol, methyl alcohol, butyl alcohol, water, or mixtures thereof, in such proportions as to give desirable evaporation characteristics. In preferred embodiments, in which a coating solution comprises metal oxide particles and condensation products of a metal alkoxide polymer, the coating solution may contain, for example, about 93% ethanol and 7% $H_2O$. Such coating solutions preferably contain about 0.2 to 25 weight percent, more preferably about 2 to 10 weight percent, metal oxide particles.

Standard techniques may be employed to obtain condensation products of a metal alkoxide polymer. Briefly, the polymer may be partially hydrolyzed (ie., from 10% to 50% of hydrolyzable bonds hydrolyzed) or substantially hydrolyzed (i.e., greater than 50% of hydrolyzable bonds hydrolyzed) by exposure to a suitable amount of water. The hydrolyzed polymer then forms condensation products, which result in extended polymers (see glossary) through the formation of oxane bonds. Such polymers may be formed before or after addition of metal oxide particles. The process of forming extended polymers is referred to herein as aging. While a variety of conditions may be used for this process, it has been found that aging for at least one day at an acidic pH is usually sufficient. The acidity of the coating solution is preferably between 2.0 and 5.0 pH units, and most preferably between 4.0 and 5.0 pH units. Increasing the acidity beyond about 7.0 pH units results in solution instability due to polymer aggregation. In contrast, coating solutions formed at an acidic pH are stable for at least 6 months at 4° C.

Within a preferred embodiment, a porous coating may be generated using a metal alkoxide and fumed silica particles. The concentration of metal alkoxide is preferably 20 μmole to 2000 μmole, and more preferably 60 μmole to 240 μmole, per gram of 500 Å silica particles. A coating solution may be made by mixing 50.0 ml of 5 weight percent silica particles (500 Å primary particle size) dispersed in 95% ethanol/5% $H_2O$, 0.435 ml of 6 mM $HNO_3$, and 0.100 ml of tetraethyoxysilane (180 μmole/g of silica particles). The coating solution thus formed may be mixed in a plastic container at room temperature for greater than 24 hours, and preferably greater than 48 hours. Optionally, the coating solution may be sonicated before use.

The coating solution may be applied using any standard technique, including dip-coating, spin-coating or microdispensing. According to one embodiment, the coating solution is applied to a substrate at an incline using a pipette. As noted above, the substrate on which the porous coating is prepared may, but need not, comprise an adhesive layer to enhance adhesion of the porous coating.

After the coating solution is applied, the solvent is allowed to evaporate leaving a continuous porous coating that is substantially uniform in thickness, and comprises a gelled network of substantially spherical metal oxide particles, and polymers of a hydrolyzed metal alkoxide coupled to one another through oxane bonds. In preferred embodiments, the evaporation of the solvent may be performed at a temperature between 10° C. and 150° C. Solvent is most preferably evaporated at room temperature.

The resulting porous coating is continuous, rigid, substantially uniform in thickness, and comprises a gelled network of particles. The metal oxide particles (and the metal alkoxide polymer, if used) are bound to one another and the substrate through oxane bonds. Particles may further be linked to one another by noncovalent bonds.

The final thickness of the porous coating may be controlled by altering the percent solids, viscosity, incline angle, withdrawal-rate in the case of dip-coating, or the spin speed in the case of spin-coating. The thickness of the porous coating may vary over a wide range (e.g., 0.05 to 25 microns). Such a coating preferably has a surface area that is at least 50 meters$^2$/g, or at least 100 square microns per cubic micron of porous coating.

A porous coating as described herein provides a high surface area for ligand attachment, thus increasing ligand density. The surface area is inversely proportional to average pore size. In turn, the average pore size closely approximates the primary particle size. Thus, the surface area and the average pore size of the coating may be tailored by the choice of primary particle size (i.e., the coating has controlled porosity) For example, a metal oxide with a primary particle size of 500 Å will have a surface area of 50 m$^2$/g, and a micron thick coating of such particles will increase the ligand density 100-fold. Similarly, a metal oxide with a primary particle size of 200 Å will have a surface area of 200 m$^2$/g, and a micron thick coating will increase ligand density 400-fold. In contrast, a primary particle size greater than 1000 Å yields porous coatings with surface areas too small to be useful in the present invention. In preferred embodiments, surface area is optimized by choosing a primary particle size not larger than that required for a given application of the invention. For example, in applications requiring solid-phase synthesis or detection of ligand-receptor binding, the surface area is optimized by choosing a primary particle size not larger than that required for sterically unrestricted diffusion of molecules through the porous network. In particular, molecules measuring less than about 10 Å, 50 Å, 100 Å, 200 Å, 500 Å, and 1000 Å will gain access to the interior of the porous coating if the coating is comprised of particles measuring greater than about 10 Å, 50 Å, 100 Å, 200 Å, 500 Å, and 1000 Å in diameter, respectively.

The surface area of a porous coating may be further increased by increasing the thickness of the coating. In the instant invention, is has been discovered that a crack-free coating up to 25 $\mu$m thick is possible with a single application of the above dispersion. In some embodiments, the porous coating is less than 1.0 $\mu$m, 2.0 $\mu$m, 5.0 $\mu$m, 10.0 $\mu$m or 25.0 $\mu$m thick. In general, however, adequate surface area enhancements are obtained when the thickness is between 2.0 $\mu$m and 5.0 $\mu$m.

D. Photopatterning

An article may comprise a single porous coating, or multiple discrete porous coatings. An article having multiple coatings may be prepared by photopatterning using photolithographic methods. Briefly, a porous coating may be applied to a substrate as described above. A layer of photoresist (which may be positive or negative) may then be established over the porous coating, sufficient to substantially cover the porous coating and fill its pore volume. Using a mask or other suitable irradiation-targeting device, the photoresist is irradiated at one or more discrete regions, such that subsequent contact of the photoresist with developer results in dissolution of the photoresist and the porous coating underlying it at one or more discrete regions. When a positive photoresist is used, contact with developer results in removal of irradiated regions of photoresist, and underlying porous coating. When a negative photoresist is used, contact with developer results in removal of the regions that were not irradiated. Stripping of the remaining photoresist with an organic solvent yields separate porous coatings on the substrate. The resulting article preferably comprises greater than $10^3$, $10^4$, $10^5$ or $10^6$ porous coatings, and each coating preferably has an area between about 1 cm$^2$ and $10^{-12}$ cm$^2$. In some embodiments, the area occupied may be extremely small, being limited by the size of the individual metal oxide particles. For example, a porous coating may occupy an area less than about $10^{-1}$ cm$^2$, $10^{-2}$ cm$^2$, $10^{-3}$ cm$^2$, $10^{-4}$ cm$^2$, $10^{-5}$ cm$^2$, $10^{-6}$ cm$^2$, or $10^8$ cm$^2$, or $10^{-12}$ cm$^2$. In preferred embodiments, the area occupied by each porous coating is preferably between about 1 $\mu$m$^2$ and 1 mm$^2$, more preferably less than about 10,000 $\mu$m$^2$, and still more preferably less than 100 $\mu$m$^2$. The methods provided herein provide exemplary reproducibility and dimensional control consistent with the mass production of patterned porous coatings with micron-scale features.

Each of the separate porous coatings, as well as their group arrangement, can assume essentially any size and any shape. For example, squares, ellipsoids, rectangles, triangles, circles, or portions thereof, along with irregular geometric shapes, may be utilized. Duplicate arrangements (e.g., more than 100) may also be applied to a single substrate for purposes of redundancy. In a preferred embodiment, the separate porous coatings are arranged as an array. As described in more detail below, such an array may be used as a ligand-array, with each porous coating comprising substantially pure ligands with a known and unique chemical composition.

1. Application of Photoresist

The photoresist layer preferably comprises a component that is base-soluble (either before or after irradiation). Many imaging chemistries are known in the art that utilize a radiation-induced change in base-solubility of a polymer (see *Desk Reference of Functional Polymers: Synthesis and Applications*, edited by Reza Arshady, (1997), American Chemical Society, Washington, D.C., pages. 295, 301, 320–326, and 341–366). Such imaging chemistries have been used to produce both positive and negative photoresists.

Certain preferred photoresists comprise a component with attached phenol groups, such as a phenolic polymer obtained by the step polymerization of phenol and formaldehyde of the general form:

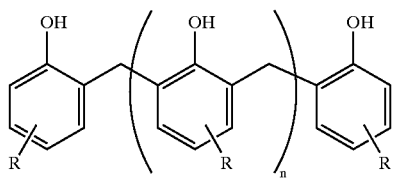

where n=0–13 and R=H or alkyl. Phenolic polymers are soluble in basic aqueous solutions through the formation of phenolate ions. For example, in some embodiments, a positive photoresist may be used that combines a phenolic polymer with a dissolution inhibitor such as a diazoquinone, onium salt, α-diazoacetoacetate, or o-nitrobenzyl cholate. Alternatively, a negative photoresist may be used that combines a phenolic polymer with a cross-linking agent such as a diazoquinone, a bisazide, or acid-activated agent in combination with a photoacid generator. Negative photoresists may also be used that are produced through masking of the base-solubilizing OH functionality of the phenolic polymer by photochemical esterification with, for example, 1,3-dioxin-4-one, diphenyltetrazole, or a polyhalide. In still other embodiments, the photoresist may be a chemically-amplified photoresist produced by combining a photoacid generator such as an onium salt, nitrobenzyl ester, or imino sulfonate with a phenolic component. Such a phenolic component may be formed from a phenolic polymer blended with an acid-labile dissolution inhibitor, a phenolic polymer capable of acid-catalyzed depolymerization, or a phenolic polymer derivatized at the OH functionality with acid-labile groups such as tert-butoxycarbonyl (t-Boc), benzhydryloxycarbonyl (Bhoc), trimethylsilyl, t-butyl, phenoxyethyl, or tetrahydropyranyl. Other positive and negative photoresists containing phenolic polymers will be apparent to those of skill in the art.

According to a preferred embodiment, the photoresist layer is from the large class of commercially available positive photoresists comprising a phenolic polymer and a diazoquinone dissolution inhibitor (see U.S. Pat. Nos. Steinhoff et al., 3,402,044; Moore, U.S. Pat. No. 2,797,213; Endermann et al, U.S. Pat. No. 3,148,983; Schmidt, U.S. Pat. No. 3,046,118; Neugebauer et al., U.S. Pat. No. 3,201,239; Sus. U.S. Pat. No. 3,046,120; Fritz et al., U.S. Pat. No. 3,184,310; Borden, U.S. Pat. No. 3,567,453; and Pampaione, U.S. Pat. No. 4,550,069). Such positive photoresists are typically prepared in a liquid form comprising 10 to 40 weight percent phenolic polymer, 10 to 40 weight percent diazoquinone, and an organic solvent such as 2-ethoxyethyl acetate or 1-methoxy-2-propyl acetate. Other additives, such as surfactants, may be present in minority fractions to promote planarization of the photoresist. In preferred embodiments, a photoresist layer is derived from such a positive diazoquinone photoresist applied to the porous coating as a thin liquid layer. Most preferably, the liquid photoresist is AZ® 1500 series positive photoresist manufactured by Hoechst TM Celanese, Somerville, N.J.

The photolytic response of phenolic photoresists reflects the photochemistry of the photosensitive diazoquinone often also referred to as a diazoketone, diazo-oxide, diazoanhydride, or quinone diazide, a chemical of the general form:

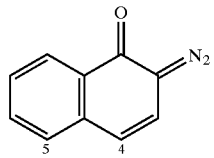

where the most commonly used versions of the general form are substituted at positions 4 or 5 with an —SO$_2$R group, where R consists of a very large variety of functionalities including sulfonic acid esters and amides of both monomeric and polymeric hydroxy, phenoxy, and amino compounds well described in the patent literature and familiar to those skilled in the art (described extensively in DeForest, Photoresist Materials and Processes, McGraw-Hill (1975)). The primary photochemical behavior of the diazoquinone is substantially the same regardless of the composition of R. Exposure to radiation with wavelengths from about 220 nm to 450 nm leads to the photolytic conversion of the base-insoluble diazoquinone (I) to an acid species (II) soluble in aqueous base.

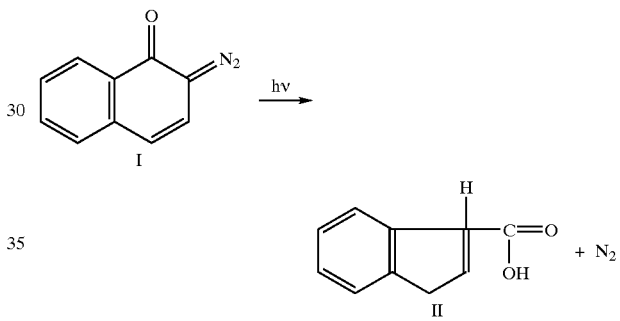

This conversion leads to a differential solubility between irradiated and non-irradiated photoresist, with irradiated regions soluble in aqueous base and non-irradiated regions substantially insoluble. Aqueous base is used herein as a developer for base-soluble photoresists, as described in greater detail below. The photolytic conversion occurs with high photosensitivity. For example, the photospeed of AZ® 1512 positive photoresist is 58 mJ/cm$^2$.

Photoresist may be applied using any standard technique. For example, a liquid photoresist may be applied as a thin liquid layer with a pipette. Excess photoresist may be allowed to drain by positioning the porous coating at an incline. Alternative methods of liquid photoresist application will be apparent to those skilled in the art, including dip-coating, spin-coating and microdispensing. All operations in the process of applying, irradiating and developing a photoresist should be carried out in a room lit primarily or entirely by light of a wavelength outside of the light range which will react with the photoresist. This may be accomplished with a protective golden shield or sleeve that blocks light less than 505 nm, placed over standard cool-white fluorescent lights (Imtec Products Inc., Sunnyvale, Calif.).

After a photoresist solution is layered onto the porous coating, the photoresist layer may be generated by evaporating the solvent. During this evaporation step, prolonged exposure to temperatures greater than about 100° C. is avoided. For example, evaporation of solvent from the coating solution is performed at a temperature less than 90°

C. (such as 85° C. to 90° C.), 50° C., 30° C., or 10° C. Most preferably, the solvent is evaporated at room temperature.

Following application, the photoresist should be continuous and cover any underlying porous coating. More specifically, the porous coating should reside under a layer of photoresist from 0.1 to 20 microns thick, preferably 0.2 $\mu$m to 4.0 $\mu$m thick and more preferably 1 to 3 microns thick. It should be noted, however, that thicker photoresists (e.g., greater than 25 microns) may be used. The final thickness of the photoresist layer may be controlled by altering the percent solids in the liquid photoresist, the molecular weight of the solids, the viscosity, incline angle, withdrawal-rate in the case of dip-coating, or the spin speed in the case of spin-coating. Depending on the thickness of the photoresist, the surface of the photoresist will be flat or will follow the surface contour of the porous coating and raised and/or depressed regions or elements. In general, the surface contour of the photoresist will be at least 0.1 microns higher than the surface contour of the porous coating(s).

2. Irradiation

Irradiation of a photoresist layer with a specific wavelength of light permits the selective, substantial removal of photoresist from irradiated (positive photoresists) or non-irradiated (negative photoresists) regions. This property results from differential solubility of irradiated photoresist, as compared to non-irradiated photoresist. The extent of this differential solubility may be assessed by exposing a selectively irradiated photoresist layer to developer and assessing the extent to which photoresist has been removed from irradiated and non-irradiated regions (e.g., using profilometry). In general, a differential solubility of at least 20-fold is sufficient. For example, irradiation of a positive photoresist and exposure to developer resulting in removal of at least 2 microns of a photoresist in irradiated regions, should result in the removal of no more than 0.1 microns in non-irradiated regions, as determined by profilometry.

Although the photoresist is preferably reactive to radiation that is in the visible, near-UV, mid-UV, or deep-UV portions of the electromagnetic spectrum, depending on the photoactive species, the photoresist may also be reactive to infrared, electron beam, x-ray or any other radiation. In some embodiments, it may be desirable to utilize photoresists sensitive to different wavelengths of light so as to, for example, selectively photopattern one of two photoresists located in different regions by irradiating both regions simultaneously.

The photoresist layer is selectively irradiated (i.e., a portion of the photoresist is irradiated with a wavelength that alters the solubility of the irradiated region). Such selective irradiation may be achieved using one or more masks and photolithographic techniques of the type known in the semiconductor industry (see Sze, VLSI Technology, McGraw-Hill (1983), and Mead et al., Introduction to VLSI Systems, Addison-Wesley (1980)). Light is preferably directed at the surface layered with the photoresist, but may also be directed at the back of the substrate, so long as it is transparent to the wavelength of light needed to react with the photoresist. The photoresist may be irradiated either in contact or not in contact with a solution, and is preferably irradiated not in contact with a solution. Using the photolithographic methods disclosed herein, it is possible to mask light to very small and precisely known locations, thereby achieving a method with exemplary reproducibility and dimensional control consistent with the production of porous coatings and porous coatings bearing ligand-arrays with micron-scale features.

A mask employed for the selective irradiation is generally an opaque support with transparent regions that allow the free passage of light to selected regions of the photoresist. Opaque regions may block light by absorbing or reflecting it. Within preferred embodiments, an ordered sequence of masks is used. In some embodiments it is possible to minimize the number of masks by utilizing the same mask to irradiate different regions by translating and/or rotating the mask with respect to each of the regions. A mask may be, for example, a glass sheet having etched chrome thereon or a silver-halide film with opaque regions obtained by laser-photoplotting. Such masks are manufactured by, for example, Precision Image Corporation, Redmond, Wash.

The transparent regions of a mask are in a pattern substantially identical to the pattern of light that will irradiate the photoresist layer, and permit the passage of light in a pattern that corresponds to the irradiated regions. The transparent regions may be of any size or shape. For example, squares, ellipsoids, rectangles, triangles, circles, or portions thereof, along with irregular geometric shapes, may be utilized. In preferred embodiments, the area of each transparent region is extremely small being between about 1 $cm^2$ and $10^{-12}$ $cm^2$, preferably less than 0.3 $cm^2$, and most preferably between about 1 $\mu m^2$ and 1 $mm^2$. For example, a transparent region may have an area less than about $10^{-1}$ $cm^2$, $10^{-2}$ $cm^2$, $10^{-3}$ $cm^2$, $10^{-4}$ $cm^2$, $10^{-5}$ $cm^2$, $10^{-6}$ $cm^2$, $10^{-7}$ $cm^2$ or $10^{-8}$ $cm^2$. In preferred embodiments, a mask comprises a plurality of transparent regions. In some embodiments, a mask comprises more than $10^2$, $10^3$, $10^4$, $10^5$, $10^6$, $10^8$ or $10^9$ separate transparent regions. In preferred embodiments, a mask comprises greater than 100 duplicates of an array of separate square or circular transparent regions, each array comprising greater than $10^3$, $10^4$, $10^5$ or $10^6$ transparent regions. It will be understood, of course, that the irradiated regions of a photoresist layer will have sizes, shapes and numbers substantially identical to the transparent regions of the mask.

During irradiation, a mask is brought into close proximity with, imaged on, or preferably brought directly into contact with the photoresist surface. In alternative embodiments, the mask may be some distance away from the photoresist surface, as occurs in the technique known as projection printing. Alignment may be performed using conventional alignment techniques in which alignment marks are used to accurately overlay successive masks, or more sophisticated techniques may be used. For example, interferometric techniques may be used (see Flanders, *App. Phys. Lett.* 31:426, 1977). In some embodiments, a patterned porous coating may itself serve as an alignment mark.

With the mask appropriately positioned over the photoresist, the mask is irradiated with light. The light may be from a conventional incandescent source, a UV source, a laser, a laser diode, an excimer laser, an x-ray source, a programmable mask, a fiber optic or the like. In some embodiments, a positive photoresist layer may be irradiated with 365 nm light from a UV transilluminator manufactured by UVP Inc. (Upland, CA) at an energy density of 8 $mW/cm^2$ for sufficient time to permit substantial removal of irradiated photoresist by developer. In preferred embodiments, the photoresist is irradiated for between 1 and 2 minutes.

To enhance the contrast of light applied to the photoresist, contrast enhancement materials may be provided between the mask and the photoresist A contrast enhancement layer may comprise a molecule that is decomposed by light or transiently bleached by light. Transient bleaching of materials allows greater penetration where light is applied, thereby enhancing contrast. Poor contrast due to standing waves and reflective notching may be reduced by applying an anti-reflective coating, for example, ARC® coating manufactured by Brewer Science Inc., Rolla, Mo. Alternatively, contrast enhancement may be provided by way of a cladded fiber optic bundle. The use of contrast enhancement materials is well known in the art.

As alternatives to the use of masks, other methods may be used to illuminate selected regions of photoresist. For example, the substrate may be translated under a modulated laser or diode light source (see Feyrer et al., U.S. Pat. No. 4,719,615). In alternative embodiments, a laser galvanometric scanner may be utilized. In other embodiments, the irradiation of the photoresist may take place on or in contact with a fiber optic light source, or a liquid crystal. By appropriately modulating liquid crystals, light may be selectively controlled so as to permit light to contact selected regions of the photoresist. Such a liquid crystal is also referred to as a "programmable mask," or an integrated circuit spatial light modulator (ICSLM), manufactured by Displaytech (Boulder, Colo.). Alternatively, irradiation may take place on the end of a series of optical fibers to which light is selectively applied. In some embodiments, light will be directed to extremely small regions, being limited by diffraction to a size directly proportional to the wavelength of light. In order to mask illumination to regions smaller than a wavelength of light, more elaborate techniques may be utilized. For example, light may be directed at the photoresist by way of molecular microcrystals on the tip of, for example, micropipettes (see Lieberman et al., *Science* 247:59, 1990). Other means of controlling the location of light exposure will be apparent to those of skill in the art.

Figure 1C:
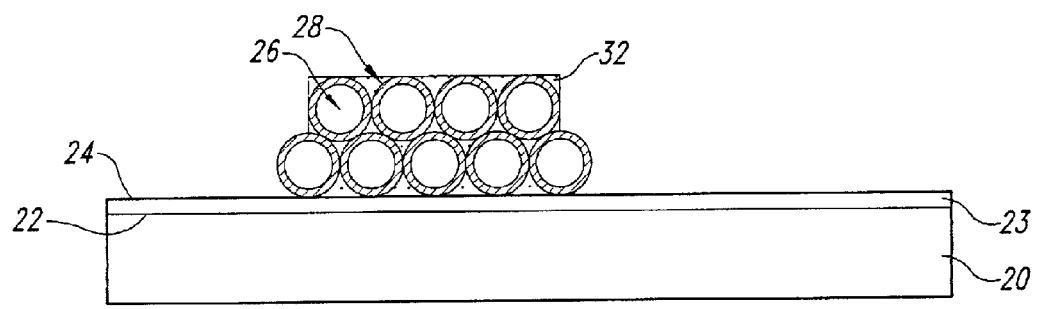
FIG. 1C is a diagram illustrating a cross-section of a representative article as shown in FIG. 1B, following removal of irradiated photoresist and underlying porous coating with a developer. Remaining photoresist 32 substantially covers the remaining gelled-network of substantially spherical metal oxide particles 26 and a metal alkoxide polymer 28.
Figure 1D:
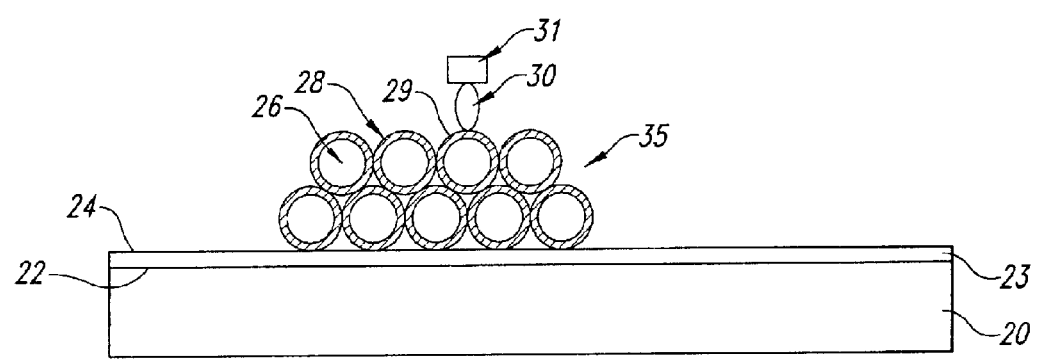
FIG. 1D is a diagram illustrating a cross-section of a representative article as shown in FIG. 1C after stripping the photoresist and attaching a ligand 31 via a linker 30.

After the irradiating step is completed, the photoresist is contacted with developer. This results in the selective, substantial removal of photoresist, and underlying porous coating, from irradiated (positive photoresists) or non-irradiated (negative photoresists) regions, leaving only photoresist and porous coating in discrete regions (see FIG. 1C, illustrating the process for a positive photoresist). The developer is selected based upon the type of photoresist. For photoresists comprising a base soluble (e.g., phenolic polymer) component, the developer preferably has an alkaline pH, more preferably 9 to 12 pH units, and most preferably about 11 pH units. The developer may also contain various buffers and surfactants. For example, the developer may be a six-fold water dilution of AZ® 351 Developer, manufactured by Hoechst Celanese™, Somerville, N.J. Contact with developer may be by any suitable method, including immersion, although other methods of applying the developer exist including, for example, spraying, puddling and streaming. The rate of photoresist dissolution can be increased by increasing the pH or increasing the temperature, limited mainly by solubility considerations of remaining photoresist. In a preferred embodiment, irradiated photoresist is contacted with developer at a temperature from 20° C. to 30° C., and most preferably at a temperature from 23° C. to 27° C., for sufficient time to effect substantial removal of desired regions of the irradiated photoresist and underlying porous coating. Typically, both are completely removed after about 60 to 120 seconds.

In the absence of photoresist, the use of an alkaline developer as described herein results in no detectable dissolution of the porous coating. It was unexpectedly found, within the context of the present invention, that dissolution of irradiated photoresist results in the dissolution of the underlying porous coating. Although the actual mechanism is uncertain, it is known that the phenomenon is mitigated and even abolished by subjecting the porous coating to temperatures normally associated with high temperature curing. Presumably, the formation of oxane bonds during high temperature curing strengthens the porous coating against the putative forces that develop during the photo-patterning process. Accordingly, it is necessary to avoid prolonged exposure to temperatures greater than about 100° C. until after the porous coating is patterned.

For photoresists not comprising a phenolic polymer, other developers (e.g., etchants) may be used to arrive at a patterned porous coating disclosed herein (suitable photoresists are reviewed extensively in *Desk Reference of Functional Polymers: Synthesis and Applications*, edited by Reza Arshady, (1997), American Chemical Society, Washington, D.C., incorporated herein by reference for all purposes). Suitable etchants for use in combination with alternative photoresists will be familiar to those skilled in the art and include, for example, reactive ion etchants, strong acids, strong bases, peroxide solutions, and mixtures thereof.

After treatment with developer, remaining photoresist is removed by contact with a stripping solution. The stripping solution is generally an organic solvent that selectively dissolves the photoresist, leaving only the patterned porous coating. In embodiments employing a phenolic polymer, the stripping solution may be, for example, a ketone, alcohol, amide, methanol, ethanol, isopropanol, 2-ethoxyethyl acetate, 1-methoxy-2-propyl acetate, or any of a wide number of organic solvents well known in the art. In a preferred embodiment, the stripping solution is acetone.

E. Application of Fortifying Solution

With or without photopatterning, a porous coating may, but need not, be treated with a fortifying solution comprising a polymeric binder to further anchor the elements of the porous coating without substantially filling the pore volume. One such binder is tetraethoxysilane. Other fortifying solutions are possible and include, for example, polymeric binders used to form the polymer-particle composites described above. In some embodiments, the fortifying solution is a 150-fold ethanol dilution of an aged solution comprising 21.7 ml of tetraethoxysilane in 6.3 ml $H_2O$ and 0.7 ml 1N nitric acid. Such a solution may be applied to a porous coating as described above. Following evaporation of the solvent (e.g., at room temperature), a fortifying layer is left on the porous coating. After evaporation, the article is preferably cured at a higher temperature, as described below.

F. Curing

A porous coating may, but need not, undergo high temperature curing to increase the number of oxane bonds. The optimal degree of oxane bonding necessary for sufficient curing will depend on numerous factors including the desired application, primary particle size, and final film thickness. In particular, small particles require less oxane bonding than large particles due to the increased strength small particles confer to a coating (i.e., secondary to greater numbers of particle-to-particle contacts per unit volume). If a porous coating is used as a substrate to attach an array of compounds, further curing may be performed so that the degree of oxane bonding will be in a relatively high range to confer increased strength on the coating.

Using either the methods described above or empirical observations, the optimal degree of oxane bonding necessary for sufficient curing for a particular application and set of conditions may be readily identified by one of ordinary skill in the art. Curing is typically achieved by heating to a temperature of about 90° C. to 250° C. for a period of time sufficient to establish an extensive network of oxane bonds. For example, a porous coating may be cured at 110–120° C. for 15 minutes.

G. Attachment of Compounds

As noted above, a porous coating preferably has at least one compound attached thereto. Such compounds may be optional. Certain coated articles may comprise a substrate having a continuous porous coating thereon of substantially uniform thickness, wherein the porous coating comprises a gelled network of metal oxide particles and polymers of hydrolyzed metal alkoxide, wherein the porosity of the coating ranges from 0.15 to 0.99. Other coated articles may comprise a substrate having at least five separate distinct porous coatings per square centimeter, wherein each coating is continuous and has a substantially uniform thickness and comprises a continuous gelled network of particles. In general, however, coated articles having attached compounds are preferred. For articles containing only one porous coating, preferably at least two compounds are attached. For articles comprising multiple porous coatings (i.e., patterned porous coatings), one or more compounds may be attached to each porous coating.

To facilitate attachment of a compound, linkers may be used. A linker may serve a variety of functions, including spacing attached compounds from the surface, facilitating receptor recognition of attached ligands, or supplying a labile linkage that allows ligands to be detached from the surface. A spacer is a small molecule that serves to separate the synthesized compound from the surface Spacers may be used alone, or incorporated into linkers. Preferred spacers for incorporation into a linker include:

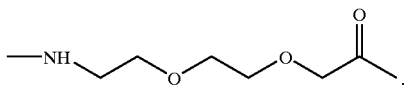

Linkers are preferably of sufficient length to allow an attached compound to interact with any desired reagents. Preferably, at least one linker at least 5 atoms long, is used, to permit free interaction between ligand and receptor, and multiple spacer molecules may be used to increase the length of a linker, if desired. Linkers may comprise, for example, aryl containing molecules, ethylene glycol oligomers containing 2–10 monomer units, diamines, diacids, amino acids, silane layers, or any of a wide variety of polymers such as polytetrafluoroethylene, polyvinylidenedifluoride, polystyrene, polycarbonate, polyethylene, polypropylene, nylon, polyvinyl alcohol, polyacrylamide, or combinations thereof. Other linker materials will be readily apparent to those of skill in the art.

In a preferred embodiment, linkers are organoalkoxysilanes containing one or more reactive groups. Reactive groups include, for example, amino (e.g., APES), hydroxy (e.g., HAPES), epoxy, carboxyl, sulfhydryl or halogen groups. Reactive groups are preferably on the distal or terminal end of the linker molecule opposite the surface. In preferred embodiments, the organoalkoxysilanes are 3-aminopropyltriethoxysilane (i.e., APES), bearing an amino group, and/or bis(2-hydroxyethyl)-3-aminopropyltriethoxysilane (i.e., HAPES), bearing two hydroxyl groups.

Within other embodiments, a linker may be selected for hydrophilic or hydrophobic properties, to improve presentation of ligands to certain receptors. For example, in the case of a hydrophilic receptor, a hydrophilic linker is preferred so as to permit the receptor to more closely approach the synthesized ligand.

Alternatively, or in addition, a linker may be selected to permit removal of an attached compound. Such a linker may be, for example, photocleavable, acid labile, base-labile or cleavable by an enzyme. The use of a photocleavable linker permits removal of ligands by irradiation with light at a wavelength that may be chosen to be distinct from wavelengths used to perform other process steps (including, for example, photopatterning of the porous coating and ligand-array synthesis). Within a photocleavable linker, the cleavable portion is preferably located at an intermediate position between the distal end of the linker and the end attached to the substrate. More preferably, the cleavable portion is located at the distal end such that photocleavage leaves no remnants of the linker on the detached compound. An acid- or base-labile linker comprises a labile moiety that permits the removal of ligand upon exposure to acid or base. An acid or base may be, for example, vapor-phase trifluoroacetic acid (TFA) or $NH_3$, respectively. Acid-, base-, and photo-labile linker molecules are known in the art, and are commercially available (see *The Combinatorial Chemistry Catalog*, Nova Biochem, Inc., 1998). One suitable acid labile linker has the formula:

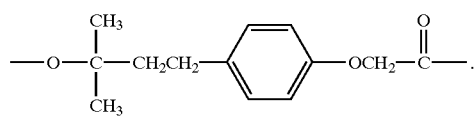

Both photocleavage and vapor-phase cleavage of ligand-arrays allow separated ligands to remain co-localized with their site of attachment and/or synthesis. Ligand separation from the support is essential for the formation of many ligand-receptor pairs. Co-localization is particularly advantageous when an in situ assay is used to determine ligand-receptor binding. In such an assay, determining the location of binding also determines the identity or reagent history of the bound ligand. It is particularly preferable to screen arrays of drug candidates using in situ assays.

A linker may also, or alternatively, comprise a recognition sequence for cleavage by an enzyme, preferably at an intermediate position. Such a sequence enables removal of ligands by contact with enzymes. An enzyme-cleavable group may be chosen so as to be substantially cleavable with a protease, non-specific nuclease, specific nuclease or enzyme secreted by a cell. Preferably, the enzyme-cleavable moiety connects the linker with the ligand so as to enable the removal of ligand upon contact with a living cell. Most preferably, the cell will secrete an enzyme that detaches the ligand from the array which subsequently diffuses into the cell and affects some internal biologic process. For example, arrays of nucleobase polymers attached via protease-sensitive linkages may be used to conduct arrays of anti-sense experiments on cells growing in direct contact with the surface of the array. Ligand separation from the support is essential for transmigration of the ligand through the cell membrane. Cell-induced cleavage of the nucleobase polymer also allows the separated ligands to remain co-localized with their site of attachment and/or synthesis. Co-localization is particularly advantageous when a phenotypic cellular assay is used to determine modulation of gene expression by the nucleobase polymer. In such an assay, determining the location of the phenotypic change determines the sequence of the nucleobase polymer affecting the change, as well as the base sequence of its intracellular target.

A linker may be covalently attached or adsorbed to the surface (via C—C, C—N, C—O, C—S, Si- or other chemical bonds) according to methods well known in the art (see *Methods in Enzymology*, vol. XLIV, edited by Klaus Mosbach, (1976), Academic Press N.Y.). For example, linkers with hydroxy groups may be attached to a surface with a 2% solution of HAPES in 95:5 ethanol:$H_2O$ for 10 minutes, followed by rinsing with ethanol and curing at 120° C. for 15 minutes. Linkers with amino groups are attached similarly except that APES is substituted for HAPES. Organoalkoxysilanes may generally be attached to a surface via siloxane bonds.

Alternatively, linkers may be incorporated into the gelled network of the porous coating by copolymerization, such that the linkers are present throughout the thickness of the porous coating. For example, in one embodiment, an amino-modified coating solution may be made by mixing 50.0 ml of 5 weight percent silica particles dispersed in 95% ethanol/ 5% $H_2O$ (500 Å primary particle size), 0.435 ml of 6 mM $HNO_3$, 0.100 ml of tetraethyoxysilane (180 $\mu$mole/g of silica particles), and 0.035 ml of APES (60 $\mu$mole/g of silica particles). The coating solution may be mixed at room temperature for two days, and yields a porous coating that directly couples to amino-reactive reagents. It is, however, preferred to attach linker molecules after forming the porous coating.

Compounds may be attached to a porous coating within separate full-thickness volumes, with or without linkers, using well known techniques. Attached compounds may have molecular weights less than about $10^1$ gram/mole, $10^2$ gram/mole, $10^3$ gram/mole, $10^4$ gram/mole, $10^5$ gram/mole, $10^6$ gram/mole, or $10^7$ gram/mole. Such compounds may be of any type including, for example, nucleobase polymers (see glossary), pharmacologic agents, drug analogues, both linear and cyclic polymers of nucleic acids, polysaccharides, phospholipids, and peptides having either $\alpha$-, $\beta$-, or $\omega$-amino acids, polyesters, polycarbonates, polyureas, polyamides, polyethyleneimines, polysiloxanes, polyimides, polyacetates or other ligands.

In preferred embodiments, a coated article comprises an array of ligand groups attached to the porous coating within separate full-thickness volumes. Arrays of ligands may be attached to the porous coating using any placement method that is compatible with the synthesis of compounds on a porous three dimensional object including, for example, ink-jet technology (see Brennan, U.S. Pat. No. 5,474,796). Most preferably, however, ligand arrays are formed on the porous support using methods and compositions described more fully in co-pending Application Ser. No. 09/326,479 entitled, "Methods and Compositions For Performing an Array of Chemical Reactions on a Support Surface" and U.S. Pat. No. 6,569,598, entitled "Solvent-Resistant Photosensitive Compositions." Synthesis methods employing photoremovable groups are not generally compatible with the porous coatings described herein, as a result of incomplete photodeprotection, and such techniques should generally be avoided.

Within certain embodiments, compounds may be synthesized on the surface of the porous coating by sequential coupling of chemical precursors using, for example, methods collectively known in the art as "solid-phase synthesis." An important aspect of the present invention is the discovery that the porous coatings provide excellent supports for performing solid-phase chemical synthesis of ligands and detecting bound ligands with labeled macromolecular receptors, using a variety of protocols and reagents. In contrast to supports that require swelling and solvation for efficient mass transfer of reagents, the rigid porous network of the present invention is permanently open and resides on the surface of the substrate. Reactive groups on the surface are therefore substantially accessible by any reagent by directly contacting the support. Accordingly, the flow-through apparatus required to apply reagents to the parallel and highly elongated sub-surface pores of the acid-etched porous silicon and electrochemically manufactured metal oxide membrane of the prior art is not necessary (see Beattie et al., *Clin. Chem.* 41:700, 1995 and Van Damme and Kreuwel, WO99/02266). Ligands may be synthetically established on the surface by any number of solid-phase synthesis methods familiar to those skilled in the art, including but not limited to, solid-phase nucleic acid synthesis (e.g., phosphoramidite or H-phosphonate methods), solid-phase peptide synthesis (e.g., the "Merrifield Method", see Merrifield, *J. Am. Chem. Soc.* 85:2149, 1963 and subsequent improvements thereto), solid-phase peptide nucleic acid synthesis (see Egholm et al., *J. Am. Chem. Soc.* 114:1895, 1992), solid-phase nucleobase polymer synthesis (see Summerton and Weller, U.S. Pat. No. 5,185,444; Shah et al., U.S. Pat. No. 5,698,685; Stirchak and Summerton, *J. Org. Chem.* 52:4202, 1987; Lebreton et al., *Synlett.* 137, 1994; Vasseur et al., *J. Am. Chem. Soc.* 114:4006, 1992; Jones et al., *J. Org. Chem.* 58:2983, 1993; Huie and Trainor, U.S. Pat. No. 5,470,967 and Swaminathan et al., U.S. Pat. No. 5,817,781), and solid-phase small-molecule synthesis (see *The Combinatorial Chemistry Catalog*, Nova Biochem, Inc., 1998).

Briefly, solid-phase synthesis may be achieved by one or more cycles through a series of four steps: (1) application of photoresist; (2) irradiation of photoresist and removal of a portion of the photoresist; (3) contact of exposed molecules with a reagent; and (4) removal (or stripping) of remaining photoresist. Each of these steps is described in greater detail below, and the series may be performed as many times as needed to generate the attached compounds of interest.

In general, chemical reactions performed on a surface may be characterized by the reagents used. For example, a reaction defined by the addition of a reagent $R_1$ is designated by the notation $[R_1]$, where the square brackets indicate the process of contacting the support with a reagent. The order of reagents contacted with a region define its reagent history. Accordingly, after a first cycle, exposed regions of a surface comprise ligands with the following reagent history:

$$S\text{-}L\text{-}[R_1],$$

wherein S indicates the surface and L indicates a linker, while remaining regions of the surface comprise ligands with the following null reagent history:

$$S\text{-}L\text{-}[\varnothing]$$

After a second cycle of photoresist application, irradiation, exposure to developer and contact with a second reagent $R_2$ (which may or may not be the same as $R_1$), different regions of the support may comprise ligands with one or more of the following reagent histories:

$$S\text{-}L\text{-}[R_1]\text{-}[R_2]$$

$$S\text{-}L\text{-}[R_2]$$

$$S\text{-}L\text{-}[R_1]$$

$$S\text{-}L\text{-}[\varnothing]$$

The above process is repeated until a plurality of ligands are attached to the substrate, each in discrete known regions and each with a known reagent history. In preferred embodiments, the reagent history will determine the predominant ligand composition at a predefined region. Thus, by controlling the regions of the support masked by photoresist and the reagent history of each region, the location and composition of each ligand will be known.

a. Application of Photoresist

To begin synthesis of attached compounds, the porous coating (and linkers) are covered by a layer of photoresist. Any suitable photoresist may be used for this purpose, provided that (1) the photoresist provides a barrier layer (2) irradiation of the photoresist results in differential solubility of the photoresist in irradiated regions, relative to non-irradiated regions; (3) such irradiation can be performed with light of a wavelength that does not result in substantial photodegradation of surface-attached molecules, (4) the photochemical reaction undergone by the photoresist is substantially inert with respect to surface-attached molecules in contact with the photoresist; (5) a suitable developer, if needed, is substantially unreactive with the surface and attached molecules and (6) the photoresist is substantially removable by stripping solutions that are substantially inert with respect to the underlying molecules and substrate.

The barrier layer provided by the photoresist should be sufficient to prevent detectable reaction of a reagent with underlying molecules under conditions that permit such a detectable reaction with such molecules that are not covered by the photoresist. The barrier layer should be at least 0.1 microns thick and should form a continuous coating. Preferably, the barrier layer is substantially impermeable to organic solvents to be used in the synthesis reactions. This property may be assessed by generating a layer, contacting one side of the layer with an organic solvent of interest, and determining whether the solvent passes through the layer under conditions that are to be used in the assay. Diffusion of solvent into the layer may be detected by testing for evidence of layer swelling. In general, a barrier layer is substantially impermeable to a solvent if its thickness increases (i.e., swells) by less than 50% at equilibrium, as determined by interferometry or profilometry. Such solvent-impermeability is desirable but is not an absolute requirement.

As described above in the context of photopatterning, irradiation of a photoresist barrier layer with a specific wavelength of light permits the selective, substantial removal of photoresist from irradiated (positive photoresists) or non-irradiated (negative photoresists) regions. In general, for a positive photoresist, a differential solubility of at least 20-fold is sufficient to produce a useful photoresist system. For example, irradiation and exposure to developer resulting in removal of at least 2 microns of a photoresist in irradiated regions, should result in the removal of no more than 0.1 microns in non-irradiated regions, as determined by profilometry.

Within the methods provided herein, such irradiation should not result in detectable alteration of the underlying molecules. Thus, a suitable photoresist should be reactive to light of a wavelength that does not result in detectable degradation of the underlying molecules. For most applications, the light should have a wavelength greater than that which causes direct photodegradation of molecules (i.e., >260 nm, preferably >300 nm). Those of ordinary skill in the art will be readily able to determine specific wavelengths that are suitable for use in the synthesis of a desired compound. Further, the chemistry that takes place within the photoresist layer upon irradiation should be substantially inert with respect to the underlying molecules. Irradiation of the photoresist should not result in reactive compounds that may react with the compounds to be synthesized. Similarly, any developer employed, and stripping agents for removal of photoresist, should not modify the underlying molecules. In other words, developers and stripping solutions should result in substantial removal of the photoresist without degrading the surface or attached molecules. In general, the process agents comprising irradiation, photochemical reactions in the photoresist, developers, and strippers should produce less than 50%, and more preferably less than 10% degradation of compounds each time they are used. Degradation may be measured by assessing reaction yields in the presence and absence of the above process agents (see Glossary phrase "substantial removal").

Suitable photoresists for use in solid phase synthesis may be identified by considering the properties of the photoinactive and photoactive components of the photoresist separately. The photoinactive component of a photoresist determines the majority of the bulk properties of a photoresist including solvent-resistance (i.e., insolubility in a particular solvent), and is typically a polymer. Suitable candidates for the photoinactive component may generally be selected from those polymers whose solvent-resistance includes the reagent solvent to be used in a particular synthetic reaction. A vast array of polymers and their solubility profiles in various solvents have been described in the art (reviewed by Fuchs in: Polymer Handbook, $2^{nd}$ edition, Wiley-Interscience, New York, edited by Brandrup and Immergut (1975), p. 379). Depending on the desired solubility profile of the photoresist, candidates for the photoinactive component may be selected from poly(dienes), poly(acetylenes), poly(alkenes), poly(acrylates), poly(acrylic acids), poly(methacrylics), poly(disubstituted esters), poly(acrylamides), poly(methacrylamides), poly(vinyl ethers), poly(vinyl alcohols), poly(acetals), poly(vinyl ketones), poly(vinyl halides), poly(vinyl nitrites), poly(vinyl esters), poly(styrenes), poly(phenylenes), poly(oxides), poly(carbonates), poly(esters), poly(anhydrides), poly(urethanes), poly(sulfonates), poly(siloxanes), poly(sulfides), poly(sulfones), poly(amides), poly(hydrazides), poly(ureas), poly(carbodiimides), poly(phosphazenes), poly(silanes), poly(silazanes), poly(benzoxazoles), poly(oxadiazoles), poly(oxadiazolidines), poly(dithiazoles), poly(benzothiazoles), poly(pyromellitimides), poly(quinoxalines), poly(benzimidazoles), poly(piperazines), poly(anhydrides), poly(formaldehydes), poly(phosphonates), poly(phosphates) and poly(thiophosphonates). Preferred polymers are those with narrow solubility profiles and include, for example, polyethylene (low density), polypropylene, poly(di-n-butyl itaconate), polyacrylamide, poly(vinyl alcohol), poly(allyl alcohol), poly(chlorotrifluoroethylene), poly(2,5-dimethoxy-1,4-phenyleneethylene), poly(oxy-1,4-phenyleneoxyisophthaloyl), poly(1-butene-co-sulfur dioxide), poly(imino(1-oxotrimethylene)), poly(1,3,4-oxadiazoles), poly(dibenzoxazole), poly(dithiazoles), poly(pyromellitimides), poly(benzimidazoles), poly(dibenzimidazoles), poly(oxypropylidene), polyamic acids and polyimides. Particularly preferable are the aromatic polyamides or "aramids" which have a very narrow solubility spectrum, being soluble mainly in n-alkyl amide solvents, as described by Preston in: *Kirk-Othmer Encyclopedia of Chemical Technology*, vol. 3, $3^{rd}$ edition, edited by Grayson and Eckroth (1978), Wiley-Interscience, New York, p. 213). In some embodiments, the photoinactive component may be a polymeric blend, wherein the blend confers enhanced solvent resistance as in, for example, the blend of certain amorphous polyamides and polyesters reported by Clagett et al. U.S. Pat. No. 5,346,967.

The photoactive component results in a change in the bulk properties of the photoresist subsequent to irradiation such that either irradiated or non-irradiated portions are removed selectively. Typically, the photoactive component changes the solubility of the photoresist in a particular liquid developer. The photoactive component may comprise a single molecule or may comprise two or more molecules in a "photoreactive system." The photoactive component may be an integral part of the photoinactive polymer through covalent attachment, or may exist as a miscible blend with the photoinactive polymer.

Suitable photoactive candidates may be selected from those photoreactive molecules that effect a change in the solubility profile of the photoinactive polymer while not adversely affecting the molecules attached to the array surface. Photoactive components with these properties may be selected by identifying those photoreactive molecules that undergo substantially intramolecular photoreactions, or photoreactions that are highly specific for a class of molecules not attached to the array surface. The photoactive component is further selected based on the wavelength of light necessary to affect a substantial photoreaction. Preferably, the photoactive component reacts to radiation in the ultraviolet (UV) or visible portion of the electromagnetic spectrum. More preferably, the photoactive component will be reactive to radiation in the near UV or visible portion of the spectrum having a reactivity to light with a wavelength greater than about 250 nm, 300 nm, 350 mm or 400 nm. Numerous photoactive components which fulfill these criteria have been described, and will be familiar to those of skill in the art.

A preferred class of photoactive components comprises molecules that inhibit the solubility of the polymeric component in a miscible blend with the polymer (see *Desk Reference of Functional Polymers: Synthesis and Applications*, edited by Reza Arshady, (1997), American Chemical Society, Washington, D.C., Chapters 2.1, 2.2, and 2.3). Such dissolution inhibitors have been used to produce both positive and negative photoresists. Preferable dissolution inhibitors are those photoactive molecules that undergo a substantially intramolecular photoreaction. These include, for example, diazoquinones:

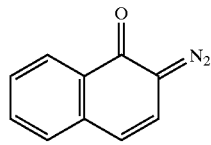

A very large variety of diazoquinone derivatives has been described in the patent literature and will be familiar to those skilled in the art (see DeForest, Photoresist Materials and Processes, McGraw-Hill (1975)). For example, diazoquinones have been successfully used as the miscible photoactive component in polyimide-based photoresists (see Yukawa and Kohtoh, U.S. Pat. No. 5,288,588 and Oba et al., U.S. Pat. No. 5,348,835). Other preferable dissolution inhibitors that undergo intramolecular photoreactions include o-nitrobenzyl cholates (see Reichmanis et al., *J. Vac. Sci. Technol.* 19:1338, 1980):

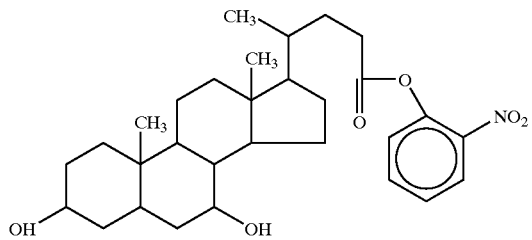

Alternatively, a negative photoresist may be formulated by combining a polymer with a photoactive component that is a cross-linking agent. Preferred cross-linking agents are those that do not react with the molecules attached to the array surface, such as those derived from stilbazolium (SBQ) substituted polymers (see U.S. Pat. Nos. 5,445,916 and 4,891,300):

A unique property of SBQ substituted polymers is that non-covalent dimers of SBQ form in the solid-state. Because SBQ units are non-covalently paired before irradiation, photoreactive species are paired and do not participate with the underlying material on the array surface.

Photoresists may also be formulated by masking a solubilizing functionality on the polymer. For example, the photoresist may be a chemically-amplified photoresist produced by combining a photoacid generator with a polymeric component derivatized at solubilizing functionalities with acid-labile groups such as tert-butoxycarbonyl (t-Boc), benzhydryloxycarbonyl (Bhoc), trimethylsilyl, t-butyl, phenoxyethyl, or tetrahydropyranyl. Preferable photoacid generators are those that do not react with the molecules attached to the array surface. For example, a preferred class of suitable photoacid generators are those which undergo substantially intramolecular reactions such as, for example, o-nitrobenzyl esters of sulfonic acids as follows:

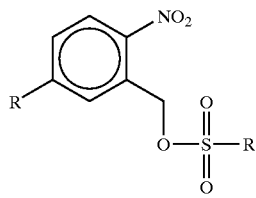

In other embodiments, the photoacid generator initiates acid-catalyzed depolymerization of the polymeric component resulting in the production of volatile components that obviate the need for wet developer processing. A preferred acid-catalyzed depolymerization reaction for polyphthalaldehyde is described by Willson et al., *J. Electrochem. Soc.: Solid-State Science and Technology* 133(1): 181, 1986.

In other embodiments, photoresists that do not require wet development may be used. Such photoresists include dye-in-polymer composites, wherein the dye assists in absorbing radiant laser energy of a particular wavelength resulting in photoablation of the photoresist by concentrated laser irradiation (see Law, *J. Appl. Phys.* 54(9):4799, 1983 and Law and Vincett, *Appl. Phys. Lett.* 39(9):718, 1981). The wavelength is one not typically absorbed by organic molecules, leaving attached organic molecules unaffected be the incident laser irradiation. Preferred dyes include, for example, oil nile blue ($\lambda_{max}$=644 nm):

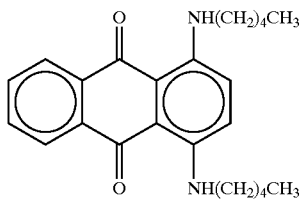

In other embodiments, the photoactive component may itself be used to mask solubilizing functionalities on the polymeric component. Preferred photoactive components for masking solubilizing functionalities include o-nitrobenzyl and N-alkyl-o-nitroanilide groups (see review by Pillai, Synthesis 1980 (1980) p. 1). Several photoresists have been described that incorporate masking groups based on o-nitro chemistries (see Kubota et al., *J. Appl. Polymer Sci.: Polymer Chem. Ed.* 33:1763, 1987). Such compounds are known to undergo predominantly intramolecular photoreactions. Particularly preferable o-nitro-based masking groups are those described by Fodor et al., U.S. Pat. No. 5,424,186.

In still other embodiments the photoactive component is attached to the polymeric component and undergoes a light-induced rearrangement to produce a solubilizing functionality. Preferred rearranging groups include diazoquinones, which have been successfully used as the photoactive adduct in polyimide-based photoresists (see Khanna, U.S. Pat. No. 5,037,720). Other preferred rearranging groups include those comprising phenyl esters, phenyl carbonates, or phenyl ethers. Such groups undergo an intramolecular photo-Fries rearrangement yielding a solubilizing hydroxyl group, as in the reaction shown below:

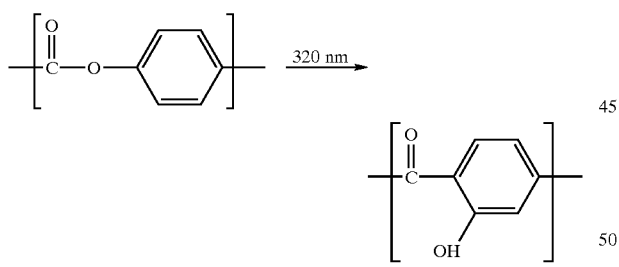

Other photoresists may be formulated by providing photolabile linkages within the polymeric component that result in a reduction in the molecular weight of the polymer and a concomitant increase in solubility. Preferred photolabile linkages include those found in polysilanes and polysulfones (see *Desk Reference of Functional Polymers: Synthesis and Applications*, edited by Reza Arshady, (1997), American Chemical Society, Washington, D.C., p. 297–300). Disilane and sulfone linkage may be incorporated into other photoinactive polymers as well. More preferred photolabile linkages include those based on o-nitrobenzyl and N-alkyl-o-nitroanilide chemistries (see Petropoulos, *J. Appl. Polymer Sci.: Polymer Chem. Ed.* 15:1637, 1977; Iizawa et al., *J. Polymer Sci.: Part A: Polymer Chem.* 29:1875, 1991; and MacDonald and Willson, in: *Polymeric Materials for Electronic Applications*, ACS Symp Ser. 184, American Chemical Society, Washington, D.C., edited by MacDonald et al., (1982), p. 73).

It will be apparent that there are many different photoresist compositions that are suitable for use within the methods provided herein. Based on the teachings of the present specification, those of ordinary skill in the art will be readily able to optimize a photoresist system for a particular application using only routine analyses.

In preferred embodiments, the photoresist is as described in U.S. Pat. No. 6,569,598 entitled "Solvent-Resistant Photosensitive Compositions." Such a photoresist generally comprises a polyamide derivative formed by the condensation of (1) a diamine mixture comprising a N-alkyl-2-nitro diamine and at least one of 1,4-phenylenediamine or 1,3-phenylenediamine and (2) a diacid chloride mixture comprising isophthaloyl chloride. Preferred N-alkyl-2-nitro diamines include $N^1$-methyl-2-nitro-p-phenylenediamine and 3,3'-dinitro-4,4'-di-N-methylaminodiphenyl ether. Preferred mole ratios of the diacid mixture to the diamine mixture range from 0.980 to 1.020.

One such photoresist comprises a polyamide derivative having a repeating unit represented by the following general formula:

(1)

where Z is 20 to 50 mole percent, and more preferably 20 to 35 mole percent, a structure comprising:

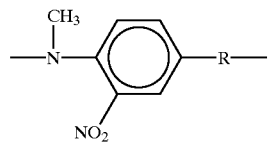

with the balance comprising

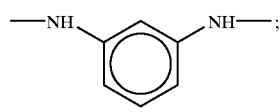

and Y is 10 to 100 mole percent a structure comprising:

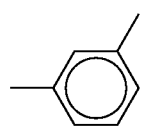

with the balance comprising

and R is a divalent organic group without particular restrictions. In some embodiments R may be selected from the group consisting of:

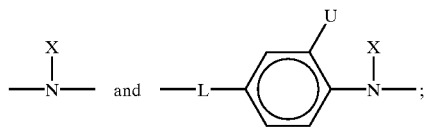

where X is H or CH$_3$; L is direct link, O, CH$_2$, N(CH$_3$), C(CH$_3$)$_2$, C(CF$_3$)$_2$, SO$_2$, CO, CONH, O(C$_6$H$_4$)$_2$, S, C(C$_6$H$_5$)$_2$ or C(CF$_3$)(C$_6$H$_5$); and U is H, NO$_2$ or CH$_3$. In preferred embodiments R is NH.

In a second embodiment, the photoresist comprises a polyamide derivative having a repeating unit represented by the following general formula:

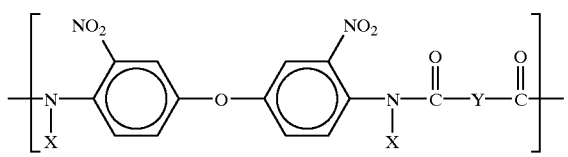
(2)

where X is 10 to 100 mole percent CH$_3$ with the balance H; and Y is 0 to 50 mole percent a structure comprising:

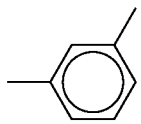

with the balance comprising

Within a third embodiment, the photoresist comprises a polyamide derivative having a repeating unit represented by the following general formula:

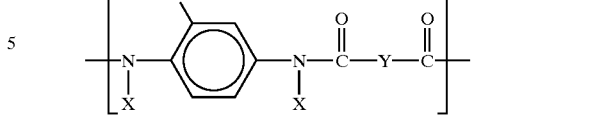
(3)

where X is 10 to 50 mole percent CH$_3$, and more preferably 10 to 20 mole percent CH$_3$, with the balance H; and Y is 20 to 100 mole percent a structure comprising:

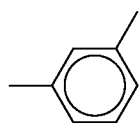

with the balance comprising

Certain preferred polyamide photoresists may be represented by the following formula:

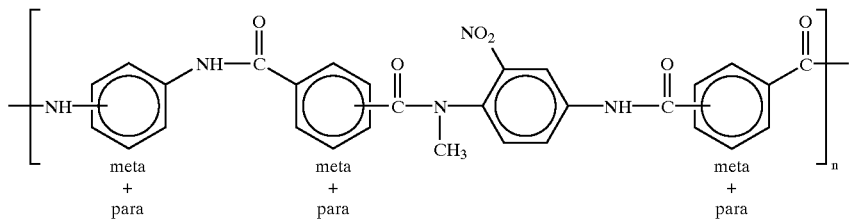

In a preferred embodiment, the polyamide is formed by condensing N$^1$-methyl-2-nitro-p-phenylenediamine, 1,4-phenylenediamine, 1,3-phenylenediamine, isophthaloyl chloride, and terephthaloyl chloride, using mole percentages of 17.67, 0.0, 32.82, 24.75, and 24.75, respectively. After polymerization, polymer ends may be capped by further condensing the polymer with benzoyl chloride. Irradiated regions of the photoresist undergo cleavage at the N-methylated amide bond forming free carboxyl groups and reducing the molecular weight of the polymer. The irradiated regions may be solubilized by a developer comprising a mixture of ethanolamine and cyclohexanone. In preferred embodiments the developer is 10–15% ethanolamine in cyclohexanone. Unirradiated photoresist may be removed by amide-based strippers including, for example, 1-methyl-2-pyrrolidinone and dimethylformamide.

The above polyamide compositions provide dry films that are resistant to numerous solvents. Irradiation of these films with 365 nm light results in intramolecular photo-oxidation as follows:

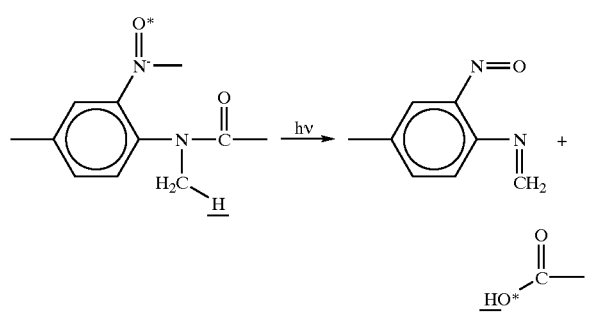

This reaction is known to be substantially intramolecular (for a review, see Pillai, Synthesis 1980 (1980) p. 1). As such, irradiation does not result in side-reactions with surface-attached groups in contact with the film. Irradiated regions may be selectively solubilized by non-aqueous developers. Without wishing to be bound by any particular theory, the photopatterning mechanism is believed to be a consequence of both polymer chain cleavage, and the appearance of acidic carboxyl groups.

A photoresist may be applied using standard techniques, as described above, including application with a pipette on an incline, dip-coating, spin-coating and microdispensing. Optimal spreading of liquid photoresist requires that the surface tension of the substrate be compatible with wetting by the photoresist solvent. For example, solvents with a surface tension below the critical surface tension of a substrate will wet the substrate surface (i.e., show a contact angle of zero). It will be apparent to those of ordinary skill in the art that contact of certain substrates with solutions at a particular pH may be necessary to create the appropriate surface tension by altering the density and/or composition of static charge on the surface. In one embodiment the substrate is briefly contacted with a basic aqueous solution (e.g., AZ® 351 developer) prior to the application of photoresist. Other methods of altering the surface tension to provide wetting by a liquid photoresist will be familiar to those of ordinary skill in the art. All operations in the process of applying, irradiating and developing the photoresist should be carried out in a room lit primarily or entirely by light of a wavelength outside of the light range which will react with the photoresist.

After a photoresist solution is applied, the photoresist layer may be generated by heating. For example, a substrate may be baked at about 85° C. to 90° C. for a few minutes until substantially all the solvent has evaporated. In preferred embodiments, photoresist coating is 0.2 μm to 4.0 μm thick. Following this soft-bake, a substrate may be further baked for several minutes at 110° C. to 135° C. to ensure complete solvent removal. Incomplete solvent removal may lead to a coating that loses integrity upon contact with various solvents.

Following application, the photoresist should be continuous and cover any underlying molecules. More specifically, the underlying molecules should reside under a layer of photoresist from 0.1 to 20 microns thick, and more preferably 1 to 3 microns thick. In embodiments that employ molecules attached to raised elements such as, for example, a plurality of porous coatings, the photoresist should also cover these elements as well. Depending on the thickness of the photoresist the surface of the photoresist will be flat or will follow the surface contour of the substrate and raised and/or depressed regions or elements. In general, the surface contour of the photoresist will be at least 0.1 microns higher than the surface contour of the attached underlying molecules.

b. Irradiation

The photoresist layer is then selectively irradiated (i.e., a portion of the photoresist is irradiated with a wavelength that alters the solubility of the irradiated region). Such selective irradiation may be achieved using one or more masks and photolithographic techniques as described above. In certain embodiments, the irradiation of the photoresist may itself result in substantial removal of the irradiated photoresist. Within other embodiments, the irradiated photoresist layer must be exposed to a developer to facilitate photoresist removal. The developer may be a solution that selectively solubilizes and removes irradiated or non-irradiated regions. In photoresist embodiments employing photoreactions that proceed by a non-crosslinking mechanism, developers may be identified by testing solvents and solvent mixtures that fall outside the solubility spectrum of the polymeric component. Often the photoactive component in such photoresists results in the production of a basic hydroxyl or carboxylic moiety and selective solubilization of irradiated portions can be achieved by the addition of an aqueous or organic base to the solvent or solvent mixture. Preferable organic bases include, for example, triethylamine, ethylamine, ethanolamine, triethanolamine, morpholine, piperidine, and diisopropylethylamine. Using these guidelines, selected solvent and base mixtures can be rapidly tested for developer activity in a panel format using several coated substrates irradiated in parallel through a test mask pattern. For photoresists based on photo-crosslinking, preferable developer solutions are most readily identified by testing solvents that are known to be within the solubility profile of the polymeric component.

Suitable developers comprise non aqueous mixtures of solvents containing ketone, amino, hydroxyl and/or amide moieties, such as N-methylpyrrolidone, dimethylacetamide or dimethylformamide. Representative mixtures which may be used to develop each of the embodiments represented by formulas (1), (2), and (3) are shown in Table I. Alternative developers may be gaseous compositions or irradiation.

TABLE I

| Photopolymer Formula | Developer Solutions (volume %) |
|---|---|
| 1 | a. 15% ethanolamine, 85% cyclohexanone |
|   | b. 15% ethanolamine, 35% acetone |
| 2 | a. 40% NMP, 60% ethanol |
|   | b. 50% ethanolamine, 50% formamide |
|   | c. 11% ethanolamime, 89% methanol |
| 3 | a. 10% triethanolamine, 90% acetone |
|   | b. 25% DMF, 25% ethanolamine, 50% acetone |

DMF is dimethylformamide

In general, a photoresist should be allowed to remain in contact with a developer solution until the photoresist coating has been substantially removed from irradiated regions of a positive photoresist (or non-irradiated regions of a negative photoresist). In preferred embodiments, this requires from 5 to 10 minutes of immersion. Regardless of the nature of the developer, exposure of the photoresist to developer results in a photoresist layer with one or more openings that expose the underlying molecules (or surface) in the irradiated region(s), for a positive photoresist.

After completion of exposure to developer, the photoresist layer may be rinsed with a suitable volatile solvent so as to remove residual developer and/or removed photoresist. One suitable rinse solvent is acetonitrile. A post-rinse heat treatment or bake may be employed to further increase the solvent-resistance of the film. In some embodiments, the film is heated at a temperature from about 90° C. to 135° C. for about one minute.

c. Contact with Reagent (s)

The regions from which photoresist has been removed are then contacted with at least one reagent. Preferably, the entire photoresist layer is contacted with the reagent, which reacts only with first molecules in exposed region(s). Liquid reagents may be applied to the support surface using several techniques including, but not limited to spraying, dipping, microdispensing or combinations thereof. Although reagents are preferably applied to the surface using solution-phase methods, it will be apparent to those skilled in the art that vapor-phase methods are also possible.

Figure 1E:
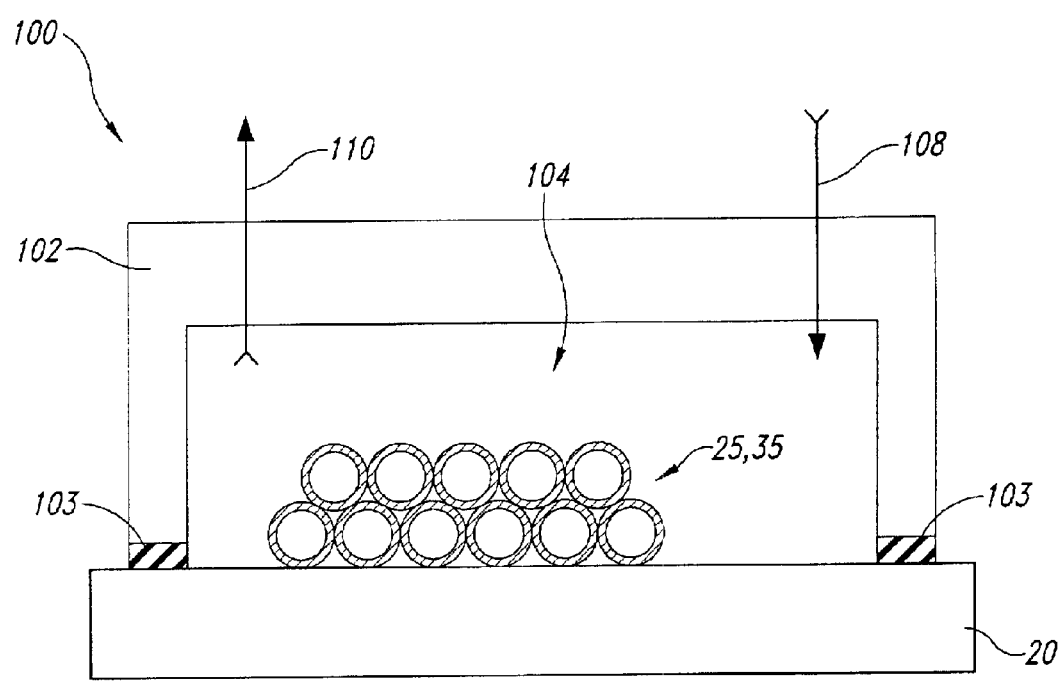
FIG. 1E is a diagram illustrating a cross-section of a reactor system 100 for applying liquid reagents to a surface of a porous coating. Reactor system 100 is formed by mating substrate 20 to a reactor base 102 with an intervening gasket 103. Sandwiched together, the substrate, gasket, and reactor base form a sealed reactor cavity 104 except for an inlet port 108 and an outlet port 110. The reactor cavity is in contact with porous coating 25 or a patterned porous coating 35.

In preferred embodiments, liquid reagents may be delivered using a reactor system depicted in FIG. 1E. The elements of such a reactor system may be held together with a clamp. The reactor cavity may have any suitable volume (e.g., 300 µl, which is sufficient to encompasses a 1.25 cm×1.25 cm region of porous coating). In preferred embodiments, the reactor base and gasket are polytetrafluoroethylene, and the substrate is glass. The reactor system allows chemical reagents to be delivered over the porous coating either manually or automatically by connecting the inlet and outlet ports to either syringes or a reagent delivery machine, respectively.

The types of reagents that may be used to construct a history are without restriction. In preferred embodiments, the reagents are components of solid-phase synthesis methods that yield biopolymers or pharmacologic analogues. Reagents are preferably precursors of organic polymers such as polynucleotides, polypeptides, peptide nucleic acids, morpholino-based nucleobase polymers, peptide-based nucleic acid mimics (PENAMs) and nuclease resistant polynucleosides.

Biopolymer ligands may be synthetically established on the surface by solid-phase nucleic acid synthesis (e.g., phosphoramidite or H-phosphonate methods), solid-phase peptide synthesis (e.g., the "Merrifield Method", see Merrifield, *J. Am. Chem. Soc.* 85:2149, 1963) or solid-phase peptide nucleic acid synthesis (see Egholm et al., *J. Am. Chem. Soc.* 114:1895, 1992). Agents with known or potential pharmacologic activity available by solid-phase synthesis include, for example, analogues of benzodiazepine, sulfonamide, hydantoin, miconazole, dihydropyridone, pyrazolone, pyrimidine, quinazoline, quinazolinone, oligocarbamates, peptoids, peptidyl phosphonates, and carboxyalkyldipeptides (see Gordon et al., *J. Medicinal Chem.* 37:1385, 1994 and *The Combinatorial Chemistry Catalog*, Nova Biochem, Inc., 1998). Other small-molecule syntheses are possible using organic reactions known to occur on the solid-phase. Illustrative examples of such reactions are shown in Table II.

TABLE II

| Transformation | Reaction or Product | Transformation | Reaction or Product |
| --- | --- | --- | --- |
| Aromatic substitution | Heck reaction/olenification<br>Suzuki reaction<br>Nucleophilic and Pd mediated<br>Fischer indole synthesis | Electrocyclic reactions | 2 + 3<br>2 + 2<br>2 + 4<br>Pauson-Khand reaction<br>Ring-closing metathesis |
| Condensations | Aldol reaction<br>Mannich reaction<br>Dihydropyridone<br>Perhydrodiazepinedione<br>Pyrazolone<br>Pyrimidine<br>Quinazoline<br>Quinazolinone | Cleavage | Amination<br>Cyclization<br>2 + cycloaddition<br>Hofmann elimination<br>Ring closing metathesis<br>Transesterification<br>Activation by acylation<br>Organocuprate reaction |
| Radical reaction<br>Michael addition | Radical cyclization | Carbene<br>Halogenation | Arndt Eistert homologation |
| Olefination | Aza Wittig<br>Horner-Emmons/Wittig | Organometallic | Grignard reaction<br>Organolithium |
| Reductions | Imine to amine<br>Azide to amine<br>Nitro to amine<br>Amide to amine | Alkylations | N-alkylation<br>C-alkylation<br>S-alkylation<br>O-alkylation |
| Amide formation | Carbamate<br>Sulfonamide<br>Urea | Oxidations | Alcohol to aldehyde<br>Alkene to epoxide<br>Sulfide to sulfoxide<br>Sulfide to sulfone | from The Combinatorial Chemistry Catalog, Nova Biochem, Inc., 1998.

Reagents may also be components of solid-phase synthesis strategies that use enzymatic methods, such as the polymerase chain reaction (PCR), in vitro RNA synthesis using an RNA polymerase, and protein synthesis using an in vitro protein translation system (e.g., reticulocyte lysate systems). Alternatively, reagents may be components of methods that couple intact ligands to the surface (see *Methods in Enzymology*, vol. XLIV, edited by Klaus Mosbach, (1976), Academic Press N.Y.). Other reagents and solid-phase synthesis methods available for attaching ligands to the substrate will be apparent to those of ordinary skill in the art.

Depending on the reagent history, a predefined region may sustain a sequence of chemical reactions that include bond coupling, bond cleaving, bond rearranging, or any combination thereof. Such bond changes typically occur in both the reagent and the attached molecules, but in some cases may occur only in one or the other. Chemical reactions may make groups on the attached molecule reactive in subsequent chemical reactions, or may deactivate or block groups from subsequent chemical reactions. In many embodiments, the last reagent in the reagent history will remove protective groups from one or more of the attached molecules. In some embodiments, the reagent history may lead to regions with attached polymers such as, for example, peptides, DNA or PNA.

In some embodiments, a plurality of reagents are sequentially contacted with a given patterned photoresist layer. In other embodiments, reagent histories are interspersed with reagents added without photoresist layers. Such reagents contribute to a plurality of ligands having reagent histories that have common sub-histories. For example, it may be desired to synthesize ligands with a reagent history of S-[$R_1$]-[$R_2$]-[$R_3$] at first regions and ligands with a reagent history of S-[$R_4$]-[$R_2$]-[$R_3$] at second regions. The process would begin by-establishing a photoresist layer and irradiating it in a first region. The photoresist is then contacted with developer, contacted with reagent $R_1$, and stripped. A second photoresist layer is established and irradiated in a second region. The photoresist is contacted with developer, contacted with reagent $R_4$, and stripped. First and second regions are then simultaneously contacted with reagent $R_2$ followed by reagent $R_3$ without photoresist layers, leaving the common sub-history [$R_2$]-[$R_3$] at both regions. The number of reagents in a common sub-history could cover a wide variety of values, but in preferred embodiments ranges from 2 to 100, 2 to 20, and most preferably 2 to 3.

In some embodiments, reagents added without photoresist layers may react differently in different regions depending on the effect of reagents added previously using photoresist layers. As an illustration, suppose it is desired to synthesize ligands with a history of S-X-[$R_1$]-[$R_2$] at first regions, and ligands with a history of S-X-[$R_4$]-[$R_2$] at second regions, where X is an attached molecule on the support surface. In the absence of a photoresist layer, the $R_2$ reagent may react differently in first and second regions depending on the product of the reactions initiated by $R_1$ and $R_4$. For example, suppose that $R_4$ removed a protective group from the only reactive group on X, and that X is inert to $R_1$. Suppose further that $R_2$ is capable of coupling to the reactive group. In this case, the $R_2$ reagent will selectively couple to X in the second regions, even in the absence of a patterned barrier layer. Conversely, previous reagents may make a particular region completely unreactive to additional reagents. For example, suppose $R_1$, added a protective group to a single reactive group on X, and $R_4$ added no such protective group. Again, application of $R_2$ will lead to selective coupling in second regions with or without a patterned barrier layer. These examples illustrate that identical sub-histories can lead to very different synthetic results.

d. Removal of Photoresist

The solvent profile of the photoinactive polymer allows suitable strippers to be readily identified by those of skill in the art. In the case of photoresists that proceed by a non-crosslinking mechanism, the final photoresist typically is stripped using solvents that solubilize the polymeric component. Such solvents are typically unreactive and cause no adverse changes in the organic molecules attached to the array surface. In preferred embodiments, a suitable stripping solution is selected from the group consisting of dimethylformamide (DMF), N-methylpyrrolidone (NMP), or dimethylacetamide (DMAC). Photoresists based on the following preferred polymers will typically be stripped by the indicated solvents:

| | |
|---|---|
| polyethylene (low density) | halogenated hydrocarbons |
| polypropylene | chlorinated hydrocarbons |
| poly(di-n-butyl itaconate) | THF |
| polyacrylamide | morpholine, water |
| poly(vinyl alcohol) | water, DMF |
| poly(allyl alcohol) | methanol, THF |
| poly(chlorotrifluoroethylene) | $CCl_4$ |
| poly(oxypropylidene) | DMF |
| poly(2,5-dimethoxy-1,4-phenyleneethylene) | bromoform |

-continued

| | |
|---|---|
| poly(oxy-1,4-phenyleneoxyisophthaloyl) | m-terphenyl |
| poly(1-butene-co-sulfur dioxide) | acetone |
| poly(imino(1-oxotrimethylene)) | chloroacetic acid |
| poly(1,3,4-oxadiazoles) | DMSO |
| poly(dibenzoxazole) | m-cresol |
| poly(dithiazoles) | DMF |
| poly(pyromellitimides) | dimethylacetamide |
| poly(benzimidazoles) | DMSO |
| poly(dibenzimidazoles) | N-methylpyrrolidone |
| polyamic acids | N-methylpyrrolidone |
| polyimides | N-methylpyrrolidone |

For photoresists based on photo-crosslinking, stripping solutions are required that cleave the crosslinked polymeric network, but do not adversely affect any organic molecules attached to the array surface. Such stripping solutions require agents which specifically cleave bonds in the polymeric network. For example, photoresists based on crosslinked polyvinyl alcohol may be selectively stripped using aqueous sodium periodate as long as the organic molecules attached to the array lack linkages comprising two or more —OH or =O groups attached to adjacent carbon atoms. Other selectively cleavable linkages in the polymer will be readily apparent to those of skill in the art.

The stripping process should substantially remove the entire photoresist layer. In other words, as noted above, the photoresist should be sufficiently removed to permit a desired reaction between underlying molecules and a reagent. Such a reaction should proceed at a yield that is at least 50%, and more preferably at least 90% of the yield observed for similar molecules that have not previously been coated with photoresist. Reaction yields may be readily determined with and without photoresist using standard techniques appropriate for the reaction of interest (see Glossary phrase "substantial removal").

The above process (coating with photoresist, selective irradiation of photoresist, substantial removal of photoresist from irradiated regions, reaction of exposed molecules within irradiated regions and removal of the remaining photoresist) may be repeated as many times as desired to achieve synthesis of different molecules in discrete known regions. It will be apparent that, within each subsequent step, irradiation may be targeted to regions that are the same as in previous steps, to regions in separate locations, or to regions that overlap previous regions to varying degrees.

Solid phase synthesis (or other attachment methods) may be used to generate an arrangement of ligands (e.g., an array) on the porous coating in virtually any shape, as described above. In a preferred embodiment, the ligand groups are arranged as an array on the porous coating, with each group comprising substantially pure ligands with a known and unique chemical composition. In some embodiments, each group comprises substantially pure ligands with a known and unique reagent history (see "reagent history" in glossary). According to some embodiments, several ligands are intentionally provided within the same predefined volume so as to provide material for an initial screening for biological activity, after which the material within the predefined volume exhibiting significant binding is further evaluated.

Thus, the methods provided herein may be used to produce an array of nearly any desired organic compounds in discrete known regions. In preferred embodiments, an array comprises greater than 10, 100, 1,000, 10,000, $10^5$ or $10^6$ unique ligands attached to a surface in discrete known regions. Such an array may occupy a total area of less than 1 cm$^2$. Each region preferably occupies an area less than about 10$^6$ μm$^2$, more preferably, less than 10,000 μm$^2$ or 100 μm$^2$, and may, in some embodiments, encompass a single ligand molecule.

The methods described above illustrate the manual construction of representative articles. It will, of course, be appreciated that automated or semi-automated methods can be used. Articles comprising the porous coating bearing attached ligands can be created by the automated application of metal oxide dispersions, and the automated addition and removal of reagents by mounting the porous coating in an automated reactor system. Successive photoresist layers and masks can be applied manually or automatically.

Ligand Arrays

An important aspect of the invention as disclosed herein, is the discovery that it is possible to produce crack-free porous coatings at least 25 microns thick, which are continuous and substantially uniform in thickness. Such features are essential in ligand array applications, which require a large but uniform ligand density on a surface.

Arrays established on a porous coating as provided herein have particular advantages with regard to screening for ligand-receptor binding. For example, a porous array provides easily recognized landmarks to rapidly identify the location of ligands bound by a receptor. In some embodiments, porous array elements serve as landmarks for their own automated removal from the adhesive surface using, for example, robotics and machine vision. Removal allows ligands to be segregated into individual reaction vessels, detached from the porous support, and screened for ligand-receptor binding. In certain embodiments, the surface between porous elements provides a differential surface tension, such that an applied receptor segregates into individual nanodroplets. Each nanodroplet adheres to a separate porous element. The spatial segregation of nanodroplets prevents the mixing of ligands from other porous elements so that in situ ligand-receptor binding can be assayed for each individual ligand.

Other advantages of a patterned porous coatings include readily recognized landmarks to align successive masks during solid phase synthesis. Also, patterned porous coatings accommodate other microfabricated systems on the substrate surface, which in some embodiments may connect with the porous elements as part of, for example, a multifunctional biochip. Microfabricated systems which may connect with such porous coatings include, for example, amplification, separation, detection, reagent delivery and semiconductor systems. Preferably, such systems are relatively small, manufactured as described above using microfabrication methods. Other microfabricated systems that may be connected to a porous coating include electronic circuitry, capillary electrophoresis (see Woolley et al., *Proc. Natl. Acad. Sci. USA* 91:11348, 1994), PCR (see Wilding et al., *Clin. Chem.* 40:1815, 1994), signal detection (see Lamture et al., *Nucl. Acids Res.* 22:2121, 1994) and microfluidic manipulation (see Burns et al., *Proc. Natl. Acad. Sci. USA* 93:5556, 1996). In some embodiments, the high ligand surface density of porous arrays may provide sufficient material to function as reagents in arrays of enzymatic reactions, including arrays of amplification reactions such as, for example, polymerase chain reactions or PCR (see Mullis, U.S. Pat. No. 4,683,202 and Mullis et al., U.S. Pat. No. 4,683,195). Other microfabricated elements which may be connected to individual patterned porous coatings bearing attached ligands and other compounds will be apparent to those skilled in the art.

It will be apparent that the type of ligands that may be attached to a porous coating as provided herein is without restriction. In preferred embodiments, the ligands may include, for example, potential pharmacologic, pesticide, or herbicide candidates, drug analogues, or important biologic polymers including DNA, PNA, PENAM and other nucleobase polymers. It will be understood, however, that such polymer ligands represent only a subset of the ligands possible using the methods provided herein. The number of reagents in a reagent history may vary over a wide range, and preferably vary from 2 to 100.

Attached compounds may be of any size and may, for example, have molecular weights less than about 10$^1$ gram/mole, 10$^2$ gram/mole, 10$^3$ gram/mole, 10$^4$ gram/mole, 10$^5$ gram/mole, 10$^6$ gram/mole or 10$^7$ gram/mole. Each attached compound is preferably substantially pure and of known chemical composition or reagent history. Within certain embodiments, each discrete region contains a compound with a structure that is different from that of the compounds in every other discrete region. Within other embodiments, the same structure may appear in multiple discrete regions. For example, ligands may be present in two or more regions for purposes of redundancy. The percentage of compounds that share a structure may be very low, or may be greater than 10%, 50%, 70% or 90%.

The resulting arrangement of ligand groups, and the shape of the area occupied by each group can be essentially any size and any shape. For example, squares, ellipsoids, rectangles, triangles, circles, or portions thereof, along with irregular geometric shapes, may be utilized. Two-dimensional arrays are generally preferred.

Certain preferred ligands are nucleobase polymers. A nucleobase polymer is a polymer of nucleobases linked to a backbone. The backbone may be naturally occurring or non-naturally-occurring. Nucleobases linked to such a backbone may be naturally-occurring or non-naturally-occurring. Such nucleobase polymers may be capable of hybridizing specifically to particular nucleic acid sequences (e.g., antisense molecules). Besides resistance to degradative enzymes, some arrays of nucleobase polymers offer additional advantages. For example, PNA arrays provide for more rapid hybridization, greater specificity, more convenient hybridization conditions (i.e., hybridization of short probes at higher temperatures) and the ability to hybridize duplex DNA directly via DNA strand displacement and triplex formation.

A further advantage of many nucleobase polymers is the ability to penetrate the membranes of living cells. In embodiments employing nucleobase polymers capable of permeabilizing cell membranes, arrays as described herein can be used to modulate gene expression in an antisense manner. Within such embodiments, each nucleobase polymer of the array is detached from the substrate while in contact with one or more living cells, preferably using an enzyme-labile linker as described herein.

Nucleobases that may be incorporated into a nucleobase polymer include, for example, purine bases and pyrimidine bases, which may be naturally-occurring or analogs of naturally-occurring bases. A large variety of analogs have been described that exhibit properties that may be advantageous in particular array applications. For example, in some cases, it may be desirable to incorporate a nucleobase that binds non-specifically at a particular position. The nucleobase present in inosine is an example of such a non-specific analog. This can be used to incorporate degeneracy into nucleobase polymers at particular positions which might be particularly useful, for example, in targeting a closely related family of target nucleic acids that are homologous except for one or a few positions in their nucleobase sequences. Inosine can pair with all four natural nucleobases, although the strength of binding varies: dC>dA>dG/T. Alternatively, the universal nucleoside 3-nitropyrrole-2' deoxynucleoside may be used to introduce degeneracy. In this strategy, the analog does not hybridize significantly to the other four natural nucleobases and makes up some of the duplex destabilization by acting as an intercalating agent.

Other types of modified nucleobases that may be of particular interest are those which enhance binding affinity. For example, diaminopurine can form three hydrogen bonds with thymine, whereas adenine and thymine form only two. Similarly, pyridopyrimidine nucleobases can be used in place of cytosine to provide stronger pairing with guanine.

Nucleobases can also comprise any of a variety of "target receptor modifying groups". By way of illustration, nucleobases can function as cross-linking moieties. For example, 6-bromo-5,5-dimethoxyhexanohydrazide can be introduced into the $C^4$ position of cytidine to alkylate and thereby crosslink guanosine (see Summerton and Bartlett, *J. Mol. Biol.* 122:145, 1978). $N^4$, $N^4$-Ethano-5-methyl-cytosine can be used to similar effect (see Webb and Matteucci, *J. Am. Chem. Soc.* 108:2764, 1986 and Cowart et al., *Biochemistry* 28:1975, 1989).

A wide range of purine and pyrimidine analogs exhibiting various properties is known in the art (reviewed in Conholly, *Methods Enzymol.* 211:36, 1992; Lin and Brown, *Methods Mol. Biol.* 26:187, 1994 and Meyer, *Methods Mol. Biol.* 26:73, 1994). Such analogs include, for example, bromothymine, azaadenines and azaguanines. An exemplary but not exhaustive list of such analogs includes: 1-methyladenine, 1-methylguanine, 1-methylinosine, 1-methylpseudouracil, 2-methylthio-$N^6$-isopentenyladenine, 2-thiocytosine, 2-methyladenine, 2-methylguanine, 2-thiouracil, 2,2-dimethylguanine, 2,6-diaminopurine-3-methylcytosine, 3-(3-amino-3-N-2-carboxypropyl)-uracil-4-acetylcytosine, 4-thiouracil, 5-fluorouracil, 5-iodouracil, 5-bromouracil, 5-methyluracil, 5-methyl-2-thiouracil, 5-methoxyaminomethyl-2-thiouracil, 5-chlorouracil, 5-carboxymethylaminomethyl-2-thiouracil, 5-methylaminomethyluracil, 5-carboxyhydroxylmethyluracil, 5-carboxymethylaminomethyluracil, 5-methoxyuracil, 5-methylcytosine, 7-methylguanine, 7-deazaguanine, 7-deazaadenine, β-D-mannoseylqueosine, β-D-galactosylqueosine, dihydrouracil, hypoxanthine, inosine, N-uracil-5-oxyacetic acid methylester, $N^6$-methyladenine, $N^6$-isopentenyladenine, pseudouracil, queosine, uracil-5-oxyacetic acid methylester, uracil-5-oxyacetic acid and xanthine.

Representative examples of suitable nucleobase polymers include peptide nucleic acids (see Buchardt et al., PCT WO 92/20702 and Buchardt et al., U.S. Pat. No. 5,719,262), which offer a number of advantages over DNA including stronger binding independent of salt concentration (i.e., a higher $T_m$ than a corresponding DNA probe), greater specificity of interaction, reduced hybridization times and resistance to environmental nucleases. Under low salt conditions, PNA binding is so energetically favorable that it binds duplex DNA directly by displacing one strand of the duplex. Other suitable nucleobase polymers include morpholino-based nucleobase polymers (see Summerton and Weller, U.S. Pat. No. 5,698,685; Summerton et al., U.S. Pat. No. 5,378,841 and Summerton and Weller, U.S. Pat. No. 5,185,444), peptide-based nucleic acid mimics or PENAMs (see Shah et al., U.S. Pat. No. 5,698,685), and polynucleosides with linkages comprising carbamate (see Stirchak and Summerton, *J. Org. Chem.* 52:4202, 1987), amide (see Lebreton et al., *Synlett.* p. 137, February), methylene (methylimino) (see Vasseur et al., *J. Am. Chem. Soc.* 114:4006, 1992), 3'-thioformacetal (see Jones et al., *J. Org. Chem.* 58:2983, 1993), sulfamate (see Huie and Trainor, U.S. Pat. No. 5,470,967) and others (see Swaminathan et al., U.S. Pat. No. 5,817,781 and Freier and Altmann, *Nucl. Acids Res.* 25:4429, 1997 and references cited therein). Particularly preferred nucleobase polymers contain repeating units as indicated below, where B is a naturally-occurring nucleobase or a non-naturally-occurring nucleobase:

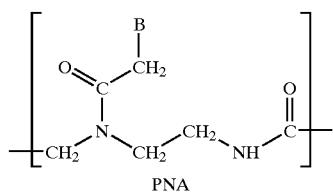
PNA

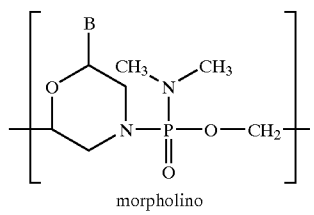
morpholino

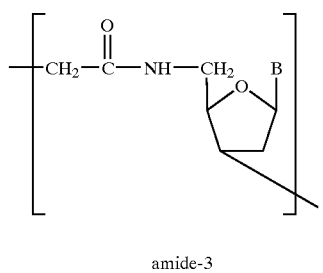
amide-3

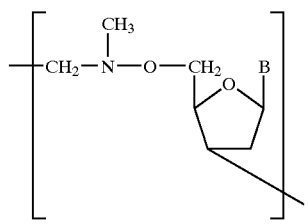
methylene(methylimino)

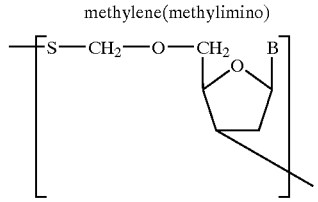
3'-thioformacetal

Other suitable nucleobase polymers will be readily apparent to those of skill in the art.

Additional representative nucleobase polymers include those comprising a morpholino subunit of the form:

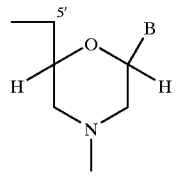

wherein (i) the subunits are linked together by uncharged phosphorus-containing, chiral linkages, one to three atoms long, joining a morpholino nitrogen of one subunit to a 5', exocyclic carbon of an adjacent subunit, and (ii) B is a nucleobase. Other nucleobase polymers may comprise a repeating unit of the form:

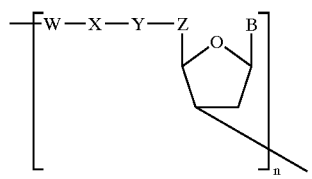

wherein each W is independently selected from the group consisting of —$CH_2$—, —O—, —S—, —CH=, —CO— and —$NR_1$—, wherein $R_1$ is hydrogen or a spacer; each X is independently selected from the group consisting of —$CH_2$—, —O—, —S—, —CH=, =CH—, =N—, —CO—, —$NR_2$—,

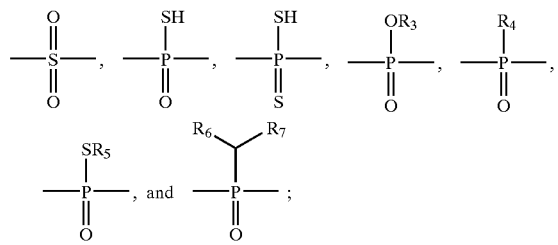

(wherein $R_2$ is hydrogen or a spacer, $R_3$ is alkyl or a spacer, $R_4$ is alkyl, cyanoethyl or a spacer group, $R_5$ is hydrogen or a spacer, $R_6$ is hydrogen or a spacer group, and $r_7$ is hydrogen or a spacer); each Y is independently selected from the group consisting of —$CH_2$—, —O—, —S—, —CH≡, —CH=, =CH—, =N—, —CO— and —$NR_8$—, wherein $R_8$ is hydrogen or a spacer; each Z is independently selected from the group consisting of —$CH_2$—, —O—, —S—, =CH—, —CO— and —$NR_9$—, wherein $R_9$ is hydrogen or a spacer; each B is independently selected from the group consisting of nucleobases; and each n is an independently selected integer ranging from 1 to 100. Other representative ligands include linear and cyclic polymers of nucleic acids, polysaccharides, phospholipids, and peptides having either α-, β-, or ω-amino acids, polyesters, polycarbonates, polyureas, polyamides, polyethyleneimines, polysiloxanes, polyimides and polyacetates.

Within preferred embodiments, an array comprises attached ligands that are resistant to degradative enzymes. In other words, at least 50% of the ligands should remain undegraded over a period of time sufficient to perform one or more useful assays in the presence of any degradative enzyme (i.e., nuclease or protease). Such arrays provide significant advantages, since they may be used in harsh environments, repetitively, with crude cell extracts or in any environment that might expose the ligand-array to the action of degradative enzymes. In applications that require the array be used to screen for the binding of nucleic acids, the resistant ligands are preferably nucleobase polymers with non-naturally occurring backbones.

Within one embodiment of a nucleobase polymer ligand-array, some of the nucleobase polymers may comprise at least one set of 2 to 10 different probes useful for interrogating the identity of a target nucleobase at a particular position in a reference sequence. One probe in a set is completely complementary to a 4 to 40 nucleotide portion that spans the reference sequence and the target nucleobase. The other probes are identical to the first probe, except that each comprises a different nucleobase substitution at the position of the target nucleobase (i.e., replacement of a particular nucleobase with a different nucleobase including nucleobase analogs, without altering the structure of the polymer backbone). Preferably, the nucleobase substitution will be centrally placed relative to the length of a probe, although this is not an absolute requirement. Contact of the array with the reference sequence will determine the identity of the target nucleobase by yielding the greatest amount of hybridization at the probe in a set which is completely complementary to the reference sequence, and lower amounts of hybridization at the probes in the set that are less than completely complementary. For example, if the reference sequence is labeled with a fluorescent label, then one may determine which probe in a set has the greatest amount of hybridization by determining which probe in the set has the strongest fluorescent signal. In particular, where non-set-containing arrays may have led to an ambiguous positive or negative signal for a particular target nucleobase detected in isolation, set-containing arrays facilitate correct recognition of the target nucleobase by providing side-by-side signal comparison for every possible target nucleobase. Preferred reference sequences for such arrays include, but are not limited to human immunodeficiency virus, human p53 gene, human CFTR gene, human factor V gene, human BRCA1 gene, human BRCA2 gene, a human leukocyte antigen and a human single nucleotide polymorphism.

The signal differential between correct and incorrect signals may be further increased through the use of a ligand-array comprising PNA nucleobase polymers. As noted above, PNA provides a greater specificity of interaction, with single nucleobase mismatches in PNA/DNA heteroduplexes being more destabilizing than the corresponding mismatches in DNA/DNA duplexes. For instance, a single mismatch in a PNA/DNA heteroduplex of length 15 lowers the $T_m$ by an average of 15° C., whereas the $T_m$ of the corresponding DNA/DNA duplex is lowered by an average of 11° C.

Although sufficient signal differentiation will usually be possible by employing sets comprising 4 probes, wherein each probe has either adenine (A), guanine (G), cytosine (C), or thymine (T) at the target position, in some embodiments it may be preferable to employ additional probes (i.e., up to a total of 10) comprising nucleobase analogues at the target position. Nucleobase analogues can be used that either stabilize or destabilize the hybridization of certain probes, and as a result, may clarify signals that would otherwise be ambiguous from probes containing only naturally occurring nucleobases. For example, suppose probes containing A and G at the target position gave about equal hybridization. Such a result would suggest two possibilities for the identity of the target nucleobase. The first possibility is that the target nucleobase is T, and the other hybridization signal represents hybridization from a T/G mismatch. The second possibility is that the target nucleobase is C, and the other hybridization signal represents hybridization from a C/A mismatch. The correct possibility may be determined by including an additional probe in the set that contains the analog 2,6-diaminopurine at the target position. If the target nucleobase is T, the probe containing 2,6-diaminopurine will yield increased hybridization relative to the hybridization from probes containing A and G. Alternatively, if the target nucleobase is C, hybridization will be unchanged or decreased relative to the hybridization from probes containing A and G. Other nucleobase analogs for increasing the difference in binding energy between possible target nucleobases suitable for inclusion in a set will be apparent to those skilled in the art.

There is no restriction on the number of such sets that an array may comprise, except as dictated by the total number of probes on an array. Maximally, the total number of sets on an array will be one-half the number of probes, and is preferably less than 100,000 sets. Relative to the reference sequence, set probes may overlap one another by any number of nucleobases, or not at all. The number of target nucleobases that may be interrogated is also without particular restriction, being limited by the total number of target nucleobases in the reference sequence. Such set-containing arrays may be used, for example, to conveniently screen for single nucleotide polymorphisms (i.e., SNPs), variants of transplantation antigens (e.g., HLAs) and single nucleobase mutations such as occurs in genetic diseases (e.g., cystic fibrosis, factor V deficiency), drug resistant pathogens (e.g., HIV and bacteria), and neoplasia (e.g., p53 gene, BRCA1 gene, and BRCA2 genes).

According to a preferred embodiment, n sets of 2 to 4 probes, more preferably sets of 4 probes, each of length 1, will be used to interrogate n target nucleobases, where the reference sequence is n nucleobases in length. Thus, every nucleobase in a reference sequence may be interrogated with sets that collectively span the reference sequence. Set-containing arrays that interrogate the identity of every nucleobase in a sequence may be used, for example, to rapidly sequence a nucleic acid molecule. The nucleic acid molecule will comprise either a known reference sequence or a variant of a known reference sequence, wherein the variant contains one or more nucleotide substitutions at a frequency not greater than 2 per any (1+2) nucleotide stretch. For values of 1 ranging from 4 to 40, the variant will thus contain one or more substitutions at a frequency not greater than 2 per any 6 to 42 nucleotide stretch, respectively. At stretches where the frequency of substitution is greater than this limit, all probes will necessarily span more than one nucleotide substitution. This results in highly variable $T_m$ values across different sets, leading to stringency conditions that are difficult to optimize.

Most preferably, set-containing arrays will contain sets comprised of nucleobase polymers that are resistant to degradative enzymes. Such articles have the significant advantage of being suitable for interrogating target nucleobases and sequencing nucleic acid molecules in a wide variety of harsh environments that contain degradative enzymes. Environments where it is desirable to perform such interrogation and sequencing, but where degradative enzymes are expected include the environments found in bodily samples such as blood, tissues, sputum, urine, and feces from both humans and animals. Other desirable harsh environments include food testing facilities, soil testing facilities, and waste water and sewage treatment plants. Other such desirable harsh environments will be readily apparent to those of skill in the art, as will the value and utility of such resistant articles in such environments.

Within other embodiments, an array may comprise ligands with attached target receptor modifying groups capable of affecting the interaction between the ligand and its target receptor, and/or affecting the target receptor itself. Examples of such modifying groups include labeling groups, intercalating groups, cleaving groups and other groups that reconform or bind to the receptor or modify the receptor. One type of modifying group that can be introduced into ligands is a nucleic acid intercalating group. A number of such intercalating groups are known in the art, many of which are acridine derivatives (see Helene and Thuong, *Genome* 31(1):413, 1989; Asseline and Thuong, *Nucleosides and Nucleotides* 10(1–3):359, 1991; Helene, *Anticancer Drug Des.* 6(6):569, 1991 and Wilson et al., *Biochemistry* 32(40):10614, 1993).

Another type of modifying group is a cross-linking group. Cross linking can be used to stabilize the interaction between a ligand and its target, which may be especially useful in achieving and stabilizing triple helix formation. Various approaches to the stabilization of triple helix formation include photochemical crosslinking (as described, for example, by Le Doan, *Nucleic Acids Res.* 15:7749, 1987 and Praseuth et al., *Proc. Natl. Acad. Sci. USA* 85:1349, 1988) and alkylation of the N7 of specific guanines in the target duplex (as described by Vlassov, *Gene* 72:313, 1988 and Fedorova et al. *FEBS Let.* 228:273, 1988).

Crosslinking can also be used to covalently link a new molecular structure, attached to a ligand, to a particular location within a target receptor. Thus, for example, a label attached to a ligand could be linked to a particular location within a receptor targeted by the ligand. Such labels could be photo-induced cross-linking agents, such as psoralen, coumarin, ellipticine and their derivatives (see Perrouault et al., *Nature* 344:358, 1990; Le Doan et al., *Antisense Res. Dev.* 1(1):43, 1991; Miller, *Methods Enzymol.* 211:54, 1992; Havre et al., *Proc. Natl. Acad. Sci. USA* 90(16):7879, 1993; and Rajagopalan et al., *J. Biol. Chem.* 268(19):14230, 1993).

Other labels that do not involve a cross-linking group may be used. A number of such labeling groups are known in the art (see Haralambidis et al., *Nucleic Acids Res.* 18(3):501, 1990; Strobel et al., *Bioconjug Chem.* 2(2):89, 1991; and Durrant and Chadwick, *Methods Mol. Biol.* 28(141):141, 1994). Such groups may be used, for example, to label particular sequences in a nucleic acid, which is useful in efforts to map and sequence various genomes.

Other modifying groups that can be introduced into a ligand array are nucleic acid alkylating agents. A number of such alkylating groups are known in the art. For example, such groups include N-mustards as reactive alkylating compounds (see Lee et al., *J. Med. Chem.* 37(8):1208, 1994), porphyrins (see Boutorine et al., *Bioconjug. Chem.* 1(5):350, 1990 and Brossalina et al., *Antisense Res. Dev.* 1(3):229, 1991), psoralens as photochemical activatable agents (see Bhan and Miller, *Bioconjug Chem.* 1(1):82, 1990 and Miller, *Methods Enzymol.* 211:54, 1992) and quinones as inducible alkylating agents (see Chatterjee and Rokita, *J. Am. Chem. Soc.* 112:9387, 1990).

Still further modifying groups that can be introduced into a ligand are nucleic acid cleaving groups. There are a number of cleaving groups that can be used to allow a ligand in an array to act as an artificial sequence-specific nuclease, which have been described in the art (see Strobel and Dervan, *Methods Enzymol.* 21:309, 1992; Sigman and Chen, *Annu. Rev. Biochem.* 59:207, 1990; Jayasena and Johnston, *Proc. Natl. Acad. Sci. USA* 89:3526, 1992; Podhajska et al.,

*Methods Enzymol.,* 216:303, 1992; Huber, *Faseb J.* 7(14) :1367, 1993; Kappen and Goldberg, *Science* 261:1319, 1993; Sigman et al., *Nature* 363:474, 1993; and Shimzu et al., *Biochemistry* 33(2):606, 1994). The following representative approaches are intended as an illustrative, not an exhaustive, list of cleaving groups. In one approach, iron (III) EDTA is used as a cleaving group which generates free radicals under appropriate redox conditions as described by Moser and Dervan, *Science* 238:645, 1987. Other redox-activated transition metal cleaving groups include complexes of o-phenanthroline-Cu(I) (introduced by Francois et al., *Proc. Natl. Acad. Sci. USA* 86:9702, 1989) and porphyrins-Fe(II) (see Le Doan, *Nucleic Acids Res.* 15:8643, 1987). These systems may be more useful in vitro, where redox activation is more readily controlled. Another alternative is photochemical cleavage as described by Perrouault et al., *Nature* 344:358, 1990. Still another approach is to incorporate as a cleaving group a relatively non-specific nuclease such as DNaseI or staphylococcal nuclease and effectively convert it into a specific endonuclease by conjugation to ligands in the array (see Corey and Schultz, *Science* 238:1401, 1987 and Pei et al., *Proc. Natl. Acad. Sci. USA* 87(24):9858, 1990). In this embodiment, the nuclease-resistance of the nucleobase polymers in the present invention is a major advantage. Yet another possible approach to cleaving target nucleic acids is to incorporate a ribozyme into the ligand array (see Haseloff and Gerlach, *Nature* 334:585, 1988; and Van and Hecht, *Adv. Inorg. Biochem* 9:1, 1994).

A modifying group can be incorporated anywhere within a ligand. However, there are a number of general considerations that should guide selection of a particular group and location. The most significant consideration is that the group should not be introduced into a position that is likely to prevent sufficient hybridization between the ligands and the target receptor. Thus, while small modifying groups can be accommodated within the region of hybridization, larger groups may be better accommodated outside of the region of hybridization. Even large modifying groups such as nuclease enzymes can be attached to terminal regions of nucleobase polymers. In some cases, the nature of the interaction between the modifying group will dictate favorable positions within the ligand. Moreover, molecular modeling can be used to anticipate favorable positions for the incorporation of such groups.

In certain embodiments, an array may comprise ligands that are drug candidates, preferably greater than 500 different drug candidates. Each drug candidate is preferably attached to the surface in quantities sufficient for screening using functional assays. Certain such reagents give rise to arrays of enaprilat analogues having the formula:

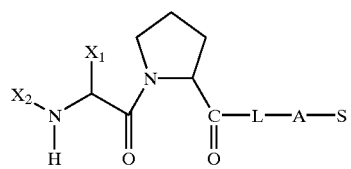

wherein S is the surface, A is aminopropyltriethoxysilane, L is a divalent linker molecule, $X_1$ is a monovalent organic group or hydrogen, and $X_2$ is a monovalent organic group or hydrogen. $X_1$ and $X_2$ may, within certain embodiments, further comprise acid labile protecting groups (i.e., removed by an acid, usually TFA or trifluoroacetic acid), such as tert-butoxycarbonyl (t-Boc), benzhydryloxycarbonyl (Bhoc), trimethylsilyl, t-butyl, phenoxyethyl or tetrahydropyranyl groups.

According to some embodiments, multiple ligands are intentionally provided within the same known discrete region so as to provide material for an initial receptor binding screen, after which the material within the pre-defined region exhibiting significant binding is further evaluated. In alternative embodiments, each known discrete region is recessed beneath the surface in, for example, a well. Each well is preferably of substantially similar dimensions to the region within it. In other embodiments, the surface between array elements provides a differential surface tension, such that an applied liquid segregates into individual droplets over each known discrete region. In some embodiments, the liquid contains an assay mixture capable of detecting binding of receptor in situ. The spatial segregation of droplets prevents the mixing of detached ligands from individual array elements. The differential surface tension may be provided by one or more organosilanes attached in a specific pattern to the surface.

Using patterned photoresist layers to make regions more or less reactive to subsequently added reagents can be used advantageously as a method for adding regional selectivity to reagents that are ordinarily incompatible with the patterned photoresist layer. For example, the synthesis of PNA uses the preferred solvents 1-methyl-2-pyrrolidinone and dimethylformamide in monomer coupling reactions. Although the polyamide photoresist is resistant to numerous solvents, it is particularly sensitive to degradation by amide solvents. This limitation is overcome by removing protective groups from the elongating end of attached PNA molecules in selected regions using a patterned photoresist layer and a compatible deprotection reagent. PNA molecules in those regions then become reactive to monomer coupling, while the remaining protected PNA molecules are unreactive. The photoresist is then stripped, and the coupling solution applied to the porous surface. Monomer couples selectively to those regions where protective groups were removed, even in the absence of a patterned barrier layer.

In some embodiments, array elements may connect with other microfabricated systems on the substrate surface as part of, for example, a multi-functional biochip. Microfabricated systems which may connect with array elements include, for example, amplification, separation, detection, reagent delivery or semiconductor systems. Preferably, such systems will be relatively small, manufactured using microfabrication methods. For example, microfabricated systems which might be connected to individual array elements include electronic circuitry, capillary electrophoresis (see Woolley et al., *Proc. Natl. Acad. Sci. USA* 91:11348, 1994), PCR (see Wilding et al., *Clin. Chem.* 40:1815, 1994), signal detection (see Lamture et al., *Nucl. Acids Res.* 22:2121, 1994), and microfluidic manipulation (see Burns et al., *Proc. Natl. Acad. Sci. USA* 93:5556, 1996). Such systems may operate in direct connection with an array element bearing certain ligands.

Arrays of Nucleobase Polymers Resistant to Degradative Enzymes

As noted above, certain preferred arrays comprise nucleobase polymer ligands that are resistant to degradation by nucleases and proteases. Such arrays may be prepared using the methods provided above; the following illustrations are provided for exemplary purposes only. It will be apparent to those of skill in the art that articles comprising a support bearing arrays of other nucleobase polymers may be readily made using essentially identical chemistry as for the nucleobase polymers described in detail. It will also be apparent that, although the following illustrations describe manual array construction, automated or semi-automated methods could be used. In particular, the application of photoresist a patterned irradiation, and addition and removal of reagents may be readily automated by those of ordinary skill in the art.

Representative PNA Array

A peptide nucleic acid (PNA) array contains ligands that comprise a backbone of repeating units of N-(2-aminoethyl)-glycine linked by amide bonds, with the bases attached to the backbone by methylene carbonyl linkages. If it is desired to synthesize all 16 possible reagent histories for a PNA dimer $N_1N_2$ using four monomers (denoted A, C, G and T) for $N_1$ and $N_2$, a square region of the support surface can be divided conceptually into a 4×4 array of 16 boxes. For illustrative purposes, it is assumed that the monomer units are the only reagents needed to form the desired PNA molecules, although it will be understood that PNA synthesis requires other reagents such as activation, washing, capping, and deblock reagents as provided in the teachings of the prior art (see Egholm et al., *J. Am. Chem. Soc.* 114:1895, 1992; Coull et al. PCT WO 96/40685; Buchardt et al., PCT WO 92/20702 and Buchardt et al., U.S. Pat. No. 5,719,262). The $N_1$ reagents are applied to the four vertical columns of the conceptual array using a positive photoresist. The first photoresist barrier exposes the left-most column of boxes, where A is applied. The second photoresist barrier exposes the next column, where G is applied; followed by a third photoresist barrier, for the C column; and a final photoresist barrier that exposes the right-most column, for T. The first, second, third, and fourth photoresist barriers may be irradiated with a single mask translated to different column locations, or four individual masks represented by the following patterns:

$$m_1 = \begin{matrix} 1 & 0 & 0 & 0 \\ 1 & 0 & 0 & 0 \\ 1 & 0 & 0 & 0 \\ 1 & 0 & 0 & 0 \end{matrix} \quad m_2 = \begin{matrix} 0 & 1 & 0 & 0 \\ 0 & 1 & 0 & 0 \\ 0 & 1 & 0 & 0 \\ 0 & 1 & 0 & 0 \end{matrix} \quad m_3 = \begin{matrix} 0 & 0 & 1 & 0 \\ 0 & 0 & 1 & 0 \\ 0 & 0 & 1 & 0 \\ 0 & 0 & 1 & 0 \end{matrix}$$

$$m_4 = \begin{matrix} 0 & 0 & 0 & 1 \\ 0 & 0 & 0 & 1 \\ 0 & 0 & 0 & 1 \\ 0 & 0 & 0 & 1 \end{matrix}$$

where digits correspond to array elements, and a "1" represents a transparent mask region and a "0" represents an opaque mask region. The process is repeated in the horizontal direction for the $N_2$ reagents. This time, the A, G, C, and T monomers are sequentially applied using photoresist barriers that expose the four horizontal rows of the conceptual array. The fifth, sixth, seventh, and eighth photoresist barriers may be irradiated with a single mask translated to different row locations, or four individual masks represented by the following patterns:

$$m_5 = \begin{matrix} 1 & 1 & 1 & 1 \\ 0 & 0 & 0 & 0 \\ 0 & 0 & 0 & 0 \\ 0 & 0 & 0 & 0 \end{matrix} \quad m_6 = \begin{matrix} 0 & 0 & 0 & 0 \\ 1 & 1 & 1 & 1 \\ 0 & 0 & 0 & 0 \\ 0 & 0 & 0 & 0 \end{matrix} \quad m_7 = \begin{matrix} 0 & 0 & 0 & 0 \\ 0 & 0 & 0 & 0 \\ 1 & 1 & 1 & 1 \\ 0 & 0 & 0 & 0 \end{matrix}$$

$$m_8 = \begin{matrix} 0 & 0 & 0 & 0 \\ 0 & 0 & 0 & 0 \\ 0 & 0 & 0 & 0 \\ 1 & 1 & 1 & 1 \end{matrix}$$

The resulting substrate contains all 16 possible reagent histories placed as represented in Table III:

TABLE III

|  | columns | | | |
|---|---|---|---|---|
| rows | S-[A]-[A] | S-[G]-[A] | S-[C]-[A] | S-[T]-[A] |
|  | S-[A]-[G] | S-[G]-[G] | S-[C]-[G] | S-[T]-[G] |
|  | S-[A]-[C] | S-[G]-[C] | S-[C]-[C] | S-[T]-[C] |
|  | S-[A]-[T] | S-[G]-[T] | S-[C]-[T] | S-[T]-[T] |

In this illustration, the $N_1$ reagents couple to the support "S", and the $N_2$ reagents couple to the already attached $N_1$ reagents. As such, the reagent histories predict polymer formation at each array element, and the sequence composition of each polymer.

The preparation of PNA arrays further provides an example of the use of patterned photoresists for solid phase synthesis reactions that employ reagents which degrade the photoresist material. Although the polyamide photoresists described herein are resistant to numerous solvents, such photoresists can be sensitive to degradation by N-alkyl amide solvents, such as 1-methyl-2-pyrrolidinone and dimethylformamide, which are commonly used in PNA synthesis. This limitation can be overcome through the use of protective groups on the elongating end of the attached PNA molecules. Such protective groups can be removed in selected regions using a patterned photoresist layer and a compatible deprotection reagent. PNA molecules in those regions then become reactive to monomer coupling, while the remaining protected PNA molecules are unreactive. The photoresist is stripped after removal of protective groups, and the coupling solution is applied to the surface. Monomer couples selectively to those regions where protective groups were removed, even in the absence of a patterned barrier layer.

As a further illustration, suppose it is desired to synthesize all 16 possible PNA dimers using Fmoc protective groups (Fmoc: fluorenylmethyloxycarbonyl, a base-labile amino-protecting group removed under nonhydrolytic conditions). As before, the support surface is divided conceptually into a 4×4 array, and the four monomer units are denoted by Fmoc-A-OH, Fmoc-G-OH, Fmoc-C—OH, and Fmoc-T-OH. Again, it is assumed for illustrative purposes that the desired PNA may be formed using only monomer units and a deprotectant as reagents. A representative deprotection reagent compatible with the polyamide photoresist comprises, for example, 20% piperidine in toluene. The support surface bears Fmoc protected linker molecules designated as P-L-Fmoc. The Fmoc groups are selectively removed from the four vertical columns of the conceptual array. The first photoresist barrier exposes the left-most column Contact with deprotection reagent removes Fmoc from the left-most column of linker molecules. The photoresist is stripped, and the A monomer is applied to the entire array surface for 30 to 40 minutes using the representative coupling solution shown in Table IV.

TABLE IV

| Representative Coupling Solution | |
|---|---|
| 80 µl | 215 mM Fmoc-monomer-OH in NMP |
| 80 µl | 181 mM HATU (O-(7-azabenzotriazol-1-yl)-1,1,3,3-tetramethyl-uronium hexafluorophosphate) |
| 80 µl | 300 mM 2,6-lutidine and 200 mM DIPEA (N,N-diisopropylethylamine) in DMF |

The second photoresist barrier exposes the next column, where Fmoc is removed. The photoresist is stripped, and the G monomer applied. This cycle is repeated for the third photoresist barrier resulting in Fmoc removal and coupling of C to the third column. A final photoresist barrier exposes the right-most column, and Fmoc is removed followed by stripping and T coupling. The process is repeated in the horizontal direction with the photoresist barriers allowing exposure of horizontal rows, and coupling of monomers to already attached monomers. The photoresist barriers are irradiated with 8 individual masks as described above by the patterns $m_1$ through $m_8$.

Although this method produces the same ligands as shown in Table III, the reagent histories are very different, as shown in Table V. In contrast to Table III, each reagent history in Table V contains every added monomer reagent, since every surface element was contacted by every monomer reagent. Specific coupling to an element occurred when deprotection preceded the addition of monomer. Accordingly, the monomer that follows the deprotection reagent in the reagent history couples to the attached linker if it is from the first set of 4 monomers, and couples to attached monomer if it is from the second set of 4 monomers.

The 625 analogues of enalaprilat have the following general formula:

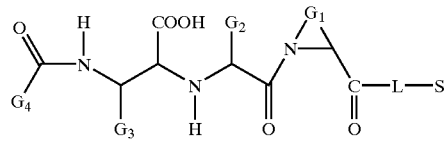

where S is the substrate, L is a linker, and $G_1$, $G_2$, $G_3$, and $G_4$ are monovalent organic groups or hydrogen. The $G_1$ group is in some embodiments attached to either nitrogen or carbon but not to both. Each analogue is synthesized directly on the support by 4 sequential couplings of reagents, with each successive coupling adding $G_1$, $G_2$, $G_3$, and $G_4$. In this example, each $G_n$ group can assume 1 of 5 different compositions designated $G_{na}$, $G_{nb}$, $G_{nc}$, $G_{nd}$, and $G_{ne}$, where n=1 to 5. By using a series of patterned photoresist layers to combinatorially direct each reagent composition to predefined regions of the support, a total of $5^4$ or 625 different analogues are possible using a total of 20 couplings. Each of

TABLE V

| columns | | | |
|---|---|---|---|
| P-L-pip-[A]-[G]-[C]-[T]-pip-[A]-[G]-[C]-[T] | P-L-[A]-pip-[G]-[C]-[T]-pip-[A]-[G]-[C]-[T] | P-L-[A]-[G]-pip-[C]-[T]-pip-[A]-[G]-[C]-[T] | P-L-[A]-[G]-[C]-pip-[T]-pip-[A]-[G]-[C]-[T] |
| P-L-pip-[A]-[G]-[C]-[T]-[A]-pip-[G]-[C]-[T] | P-L-[A]-pip-[G]-[C]-[T]-[A]-pip-[G]-[C]-[T] | P-L-[A]-[G]-pip-[C]-[T]-[A]-pip-[G]-[C]-[T] | P-L-[A]-[G]-[C]-pip-[T]-[A]-pip-[G]-[C]-[T] |
| P-L-pip-[A]-[G]-[C]-[T]-[A]-[G]-pip-[C]-[T] | P-L-[A]-pip-[G]-[C]-[T]-[A]-[G]-pip-[C]-[T] | P-L-[A]-[G]-pip-[C]-[T]-[A]-[G]-pip-[C]-[T] | P-L-[A]-[G]-[C]-pip-[T]-[A]-[G]-pip-[C]-[T] |
| P-L-pip-[A]-[G]-[C]-[T]-[A]-[G]-[C]-pip-[T] | P-L-[A]-pip-[G]-[C]-[T]-[A]-[G]-[C]-pip-[T] | P-L-[A]-[G]-pip-[C]-[T]-[A]-[G]-[C]-pip-[T] | P-L-[A]-[G]-[C]-pip-[T]-[A]-[G]-[C]-pip-[T] |

"pip" indicates piperidine in toluene, use "deprotection reagent".

Representative Array of Enaprilat Analogues

As an illustration of a method for producing a support bearing a drug candidate array, 625 enalaprilat analogues may be synthesized in an array. Enalaprilat is one of a class of antihypertensive drugs that bind angiotensin-converting enzyme (ACE) and inhibit its dipeptidase activity. ACE generates the powerful vasoconstrictor substance angiotensin II by removing the C-terminal dipeptide from the precursor decapeptide angiotensin I. Enalaprilat is a dipeptide analogue with the following formula:

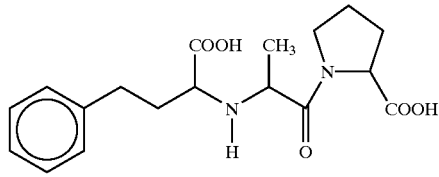

Enalaprilat is a carboxyalkyldipeptide transition-state inhibitor with the $CHCO_2H$ and NH groups mimicking the transition state-like geometry attained at the scissile peptide bond of angiotensin I (see Patchett et al., *Science* 288:280, 1980). Screening of enalaprilat analogues may be used to identify ACE inhibitors with improved potency, bioavailability, half-life, or side-effect profile.

the four coupling reactions used to synthesize a given analogue XIII, are shown below:

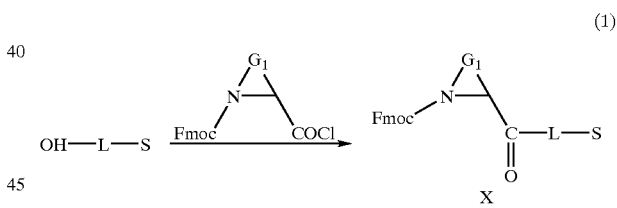
(1)

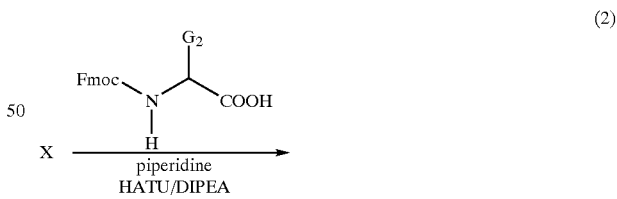
(2)

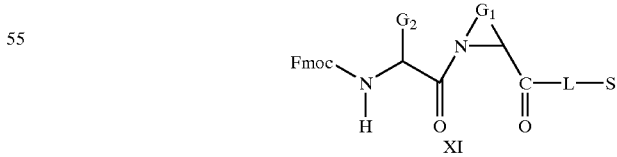

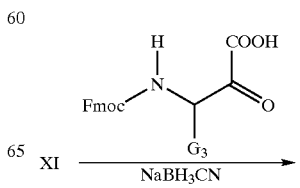
(3)

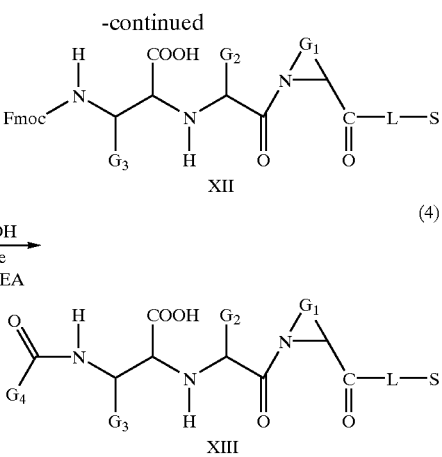

(4)

To place these 625 analogues on the support using solid-phase synthesis and a polyamide photoresist, it is convenient to divide the surface into a 25×25 array of 625 boxes. As shown in Table VI, the array synthesis is completed using 20 reaction cycles comprising 20 patterned photoresist layers and 5 applications of each of the above coupling reactions. For each $G_n$ in the array, five patterned photoresist layers direct the application of compositions designated $G_{na}$, $G_{nb}$, $G_{nc}$, $G_{nd}$, and $G_{ne}$ by either blocking reagents directly, or making regions more reactive to reagents. Each photoresist layer is patterned with an individual mask comprising a pattern of transparent rows or columns corresponding to the rows or columns in the 25×25 array. Each pattern is indicated by a condensed notation in Table VI. This notation represents every mask pattern by a column or row cross-section. For example, the pattern notation for cycle indicates a mask with transparent columns corresponding to every fifth column in the 25×25 array. In cycle 20, the pattern notation is the same, but the mask type indicates that the pattern notation refers to a mask where every fifth row is transparent. In most embodiments, synthesis of the analogue array is followed by the removal of protecting groups from one or more $G_n$ groups.

TABLE VI

| Cycle | Reaction | Composition | Mask Type | Mask Pattern |
|---|---|---|---|---|
| 1 | 1 | $G_{1a}$ | column | 1111100000000000000000000 |
| 2 | 1 | $G_{1b}$ | column | 0000011111000000000000000 |
| 3 | 1 | $G_{1c}$ | column | 0000000000111110000000000 |
| 4 | 1 | $G_{1d}$ | column | 0000000000000001111100000 |
| 5 | 1 | $G_{1e}$ | column | 0000000000000000000011111 |
| 6 | 2 | $G_{2a}$ | row | 1111100000000000000000000 |
| 7 | 2 | $G_{2b}$ | row | 0000011111000000000000000 |
| 8 | 2 | $G_{2c}$ | TOW | 0000000000111110000000000 |
| 9 | 2 | $G_{2d}$ | row | 0000000000000001111100000 |
| 10 | 2 | $G_{2e}$ | row | 0000000000000000000011111 |
| 11 | 3 | $G_{3a}$ | column | 1000010000100001000010000 |
| 12 | 3 | $G_{3b}$ | column | 0100001000010000100001000 |
| 13 | 3 | $G_{3c}$ | column | 0010000100001000010000100 |
| 14 | 3 | $G_{3d}$ | column | 0001000010000100001000010 |
| 15 | 3 | $G_{3e}$ | column | 0000100001000010000100001 |
| 16 | 4 | $G_{4a}$ | row | 1000010000100001000010000 |
| 17 | 4 | $G_{4b}$ | row | 0100001000010000100001000 |
| 18 | 4 | $G_{4c}$ | row | 0001000010000100001000010 |
| 19 | 4 | $G_{4d}$ | row | 0001000010000100001000010 |
| 20 | 4 | $G_{4e}$ | row | 0000100001000010000100001 |

In some embodiments, each $G_n$ group is selected from 1 of 10 different compositions. By forming every $G_n$ combination, $10^4$ or 10,000 analogues are synthesized in a total of 40 cycles. Other agents with known or potential pharmacologic activity available by combinatorial solid-phase synthesis include, for example, analogues of benzodiazepine, sulfonamide, hydantoin, miconazole, dihydropyridone, pyrazolone, pyrimidine, quinazoline, quinazolinone, oligocarbamates, peptoids, and peptidyl phosphonates. Accordingly, it will be appreciated by those of skill in the art that the above method can be used for the parallel production of supports bearing thousands or millions of drug candidates and other compounds using barrier layers and the photolithographic techniques disclosed herein.

Use of Arrays for Ligand-Receptor Binding Assays

Articles comprising one or more porous coatings as described herein may be used to screen for ligand-receptor binding. For example, such arrays can be used to determine peptide and nucleobase sequences that bind to proteins or nucleic acids, identify epitopes recognized by antibodies, evaluate a variety of drugs and metabolites for clinical and diagnostic applications, and screen small-molecule libraries for novel drugs, pesticides, or herbicides, as well as combinations of the above. In some embodiments where the ligand and receptor are both polymers, the sequence of the polymer at the locations where the receptor binding is detected may be used to determine all or part of a sequence which is complementary to the receptor. Of course, it is also possible to screen for ligand-receptor binding using receptor arrays, rather than ligand-arrays, using the methods provided herein.

To use a ligand-array to identify ligands that bind a specific receptor, the array is first contacted with a receptor of interest under conditions and for a time sufficient to permit receptor-ligand interaction. Following such contact, any of a variety of methods may be used to determine whether any ligands attached to the array specifically bind the receptor.

As noted above, there are a variety of molecules that may be used as receptors within such assays, including nucleic acid molecules, polypeptides, peptides, PNA, enzymes, enzyme cofactors, lectins, sugars, polysaccharides, antibodies, cell receptors, phospholipid vesicles, or any one of a variety of other receptors. Alternatively, a receptor may be a biological structure such as a cell, cellular membrane or organelle. A receptor may bind with zero, one or more ligands on the array. In some embodiments, a receptor may be from blood obtained from either healthy or diseased subjects, and screening an array for binding by the receptor may have diagnostic applications.

Figure 3:
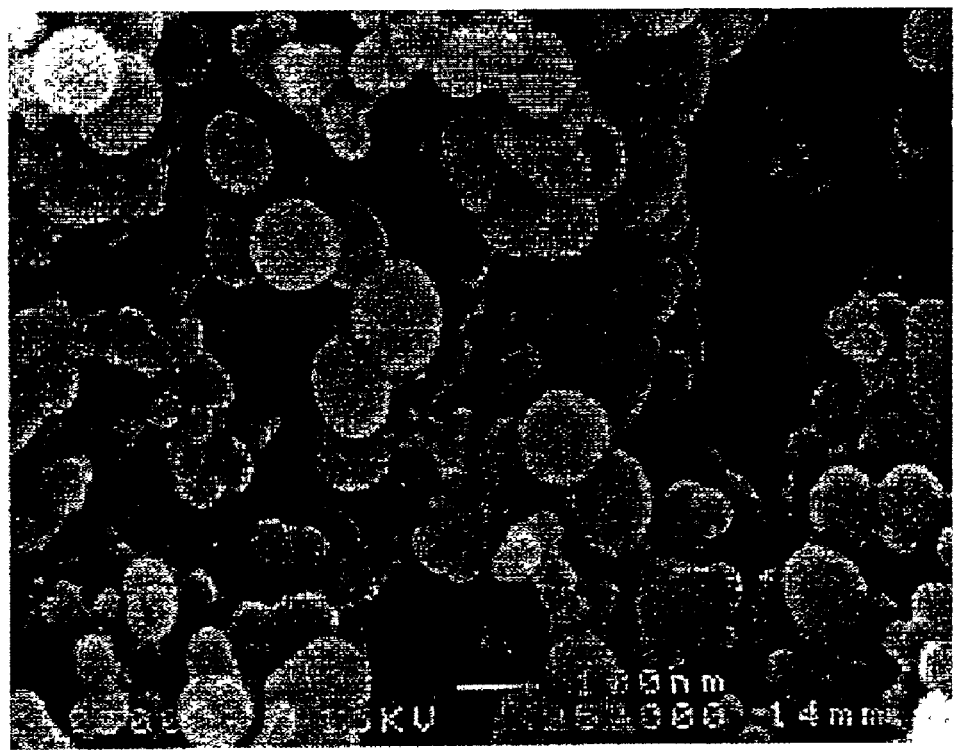
FIG. 3 is a scanning electron microscope print of the porous coating in FIG. 2 at a magnification of 95,000×. Minute granularities on the surface of the metal oxide particles are due to sputtered metal deposited on the specimen as part of the preparation process for viewing with the scanning electron microscope. The scale-bar at the bottom of the print is 100 nm long.

A receptor may be contacted with an array by placing an aliquot of a receptor solution directly on the array. Optionally, a microscope cover-slip is then placed on the receptor solution. In other embodiments, a receptor solution may be applied while the array is mounted to a reactor system as shown in FIG. 3 by circulating the receptor solution through inlet and outlet ports. Alternatively, an entire array may be immersed in a receptor solution. In addition to receptor, receptor solutions may contain one or more buffers, salts, protein, nucleic acid, detergents, cofactors, polyelectrolytes and/or other such materials necessary for a particular receptor to bind ligand. Such binding adjuvants are well known in the art. Representative DNA receptor and antibody receptor solutions which may be utilized to screen the support for ligand-receptor binding are shown in Table VII.

TABLE VII

| DNA Receptor Solution | Antibody Receptor Solution |
|---|---|
| 10 nM to 10 µM labeled DNA | 0.1 to 4.0 µg/ml antibody |
| 66 mM NaH$_2$PO$_4$/Na$_2$HPO$_4$ | 0.2M NaH$_2$PO$_4$/Na$_2$HPO$_4$ |
| 1M NaCl | 150 mM NaCl |
| 6 mM EDTA | 1% bovine serum albumin |
| 0.05% Triton X-100 ™ | 0.5% Tween-20 ™ |

During contact, it may be important to maintain a specific temperature of the array. For example, temperature can influence the stringency of DNA, PNA, and other nucleobase polymer interactions such that specific binding to particular array elements will only be observed in a narrow temperature range. In other cases, a particular temperature may be required for a receptor to either adopt a needed conformation, or avoid thermal denaturation. An optimal temperature for performing an assay may be readily determined by those of ordinary skill in the art.

If the temperature range for specific binding overlaps for all array elements, then a discrete temperature may be identified that is suitable to simultaneously screen for ligand-receptor binding at all array elements. Alternatively, if the temperature range for specific binding does not overlap for some array elements, then screening for ligand-receptor binding may have to be performed at multiple discrete temperatures. In some embodiments, ligand-receptor binding may have to be performed over a temperature gradient that samples all temperatures between two discrete temperatures. Screening for ligand-receptor binding at a plurality of temperatures within a temperature gradient is particularly useful for arrays whose elements vary widely with respect to $T_m$ and stringency.

Methods for maintaining the ligand-derivatized support at a particular temperature include, for example, placing the support in contact with a heating block, thermo-electric (Peltier) device, heated water bath, convection oven, refrigerator, freezer, or temperature controlled reactor system. In some embodiments, the substrate is mounted on a microscope stage that contains an aqueous gel within its interior chilled to a specific temperature. Other methods for controlling the temperature of the ligand-derivatized support during contact with a receptor will be apparent to those skilled in the art.

Methods for detecting binding include the detection of a marker that permits determination of the location of bound receptor on the array. Suitable markers are well known in the art, and include radionuclides and fluorescent molecules. Markers may indicate the presence of ligand-receptor pairs by producing, for example, a differential color, absorption of electromagnetic radiation, optical interference, electric conduction, radioactive decay, fluorescence, chemiluminescence, phosphorescence, or a molecular shape detectable by scanning tunneling microscopy (STM) or atomic force microscopy (AFM), either by themselves or via other covalently and non-covalently linked molecules, labels, nuclear isotopes, antibodies, or enzymes. In some embodiments the ligand-receptor pair may produce a phenotypic change including, for example, cessation of cell growth, initiation of cell growth, apoptosis or cellular differentiation. Other methods of locating and visualizing ligand-receptor pairs will be apparent to those skilled in the art.

A ligand-array may be exposed only to a labeled receptor. Alternatively, an array may be exposed to a first, unlabeled receptor of interest and, thereafter, exposed to a labeled receptor-specific recognition element, which is, for example, an antibody. Such a process provides for additional amplification of signal during detection. In yet another embodiment, a multi-labeling scheme may be employed whereby the ligand-derivatized support is exposed to several different receptors, each coupled to a different label or combination of labels. A set of images, each representing the surface density of a particular label can be generated using spectral deconvolution methods well known in the art. Such multi-labeling strategies have a variety of uses. For example, the microenvironment of the sample may be examined using special labels whose spectral properties are sensitive to some physical property of interest. In this manner, pH, dielectric constant, physical orientation, and translational and/or rotational mobility may be determined.

In a preferred embodiment using a porous array, the location of bound receptor on the array is determined by detecting fluorescence with a conventional charge-coupled device, a conventional film-based camera, or by visual inspection using fluorescence microscopy. One advantage of a porous support is an increased ligand surface density, such that imaging of bound receptors is both rapid and economical using standard equipment.

In other embodiments, an indicator compound is added that indirectly detects ligand-receptor binding. An indicator compound refers to a compound that has a detectable property in the presence of a receptor that is different when the receptor is bound by a ligand. Such detectable properties include color, light absorbance, light transmission, fluorescence, fluorescence resonance energy transfer, fluorescence polarization, phosphorescence, catalytic activity, molecular weight, charge, density, melting point, chromatographic mobility, turbidity, electrophoretic mobility, mass spectrum, ultraviolet spectrum, infrared spectrum, nuclear magnetic resonance spectrum, elemental composition and X-ray diffraction. In one embodiment, the indicator compound furylacryloylphenyalanylglycylglycine (FAPGG) is used to detect binding of angiotensin converting enzyme (ACE) by an array of enalaprilat analogues. Hydrolysis of FAPGG by ACE results in a decrease in absorbance at 328 nm. The decrease in absorbance is attenuated if ACE is bound by an enalaprilat analogue. Other indicator compounds will be readily apparent to those skilled in the art.

The signal-to-noise ratio of the assays provided herein is sufficiently high that the relative binding affinity of receptors to a variety of support-bound ligands can be determined. A receptor may bind to several ligands in an array, but may bind much more strongly to some ligands than others. Strong binding affinity will be evidenced herein by a strong fluorescent signal since many receptor molecules will bind in a region of a strongly bound ligand. Conversely, a weak binding affinity will be evidenced by a weak fluorescent signal due to the relatively small number of receptor molecules which bind in a particular region of the support having a ligand with a weak binding affinity for the receptor. Consequently, it is possible to determine relative binding avidity of a ligand herein by way of the intensity of a fluorescent signal in a region containing that ligand. In preferred embodiments, using a porous support as described above, this can be performed economically and with standard equipment. Semiquantitative data on affinities may be obtained by the inclusion of one or more ligands with known binding constants.

Depending on the application, ligand-receptor binding assays may be performed on attached or detached ligands. In preferred embodiments where ligands are biologic polymers such as DNA or PNA, ligands are screened for receptor binding while attached to the substrate surface. In preferred embodiments where ligands with potential pharmacologic activity are being screened, ligands are screened after they are detached from the substrate surface. Such assays permit the detection of ligand-receptor binding that may be sterically restricted by attachment of the ligand to the support. In such screens, it is preferred that the detached ligands have a local concentration of at least 10 µM, thereby allowing identification of ligands with low to moderate binding affinities. This may be accomplished, for example, using a porous coating as described herein, in which the concentration of ligand in the porous coating typically exceeds 10 µM, and in some embodiments is greater than 2 mM, 10 mM, 50 mM, or 200 mM. In preferred embodiments, ligands are detached without losing their positional information, since array position determines the reagent history and preferably the composition of each detached ligand. Without positional information, screening is less straightforward requiring deconvolution of pooled ligands via iterative syntheses, or analysis of orthogonally synthesized encoded-tags (reviewed by Gordon et al., *J. Med. Chem.* 37:1385, 1994). All or a portion of the ligands may be detached from the surface simultaneously. Preferably, at least 50,% of the ligands are detached in a binding assay performed using detached ligands.

One method for maintaining positional information for ligands bound to a porous array involves separating known porous layers from the surface, and segregating each of them to a known reaction vessel. With each porous layer appropriately segregated, the ligands are detached from each porous layer and screened for ligand-receptor binding individually. Preferably, the separating and segregating processes are performed automatically using, for example, robotics and machine vision. In some embodiments, the separation of the porous layer from the adhesive surface may be in response to the local and selective application of, for example, light, heat, ultrasonic radiation, solvent, magnetism, vacuum, abrasion, adhesion, scraping, high-pressure liquid streams, laser radiation, or cutting. In other embodiments, the separating process may involve a release layer sandwiched between each porous layer and the adhesive surface. The release layer may affect separation of the porous layer from the adhesive surface in response to the local and selective application of any of the above conditions. In one embodiment, porous layers are sliced off the surface after the application of a polymeric binder to prevent fragmentation of the layers.

Another method for maintaining positional information involves connecting ligands to the solid-support via photo-cleavable linkers (e.g., linkers that are cleaved upon exposure to a particular ultraviolet, visible or infrared wavelength), base-labile linkers, acid-labile linkers or linkers that comprise a recognition sequence that is cleaved by an enzyme. Exposing such cleavable linkers to acid or base in the vapor-phase (e.g., trifluoroacetic acid or ammonia vapor), to light, or to cells having a cell surface enzyme that cleaves a linker allows separated ligands to remain co-localized with their site of attachment and/or synthesis on the array (see Quillan et al., *Proc. Natl. Acad. Sci. USA* 92:2894, 1995; and Bray et al., *Tetrahedron Lett.* 32:6163, 1991). Screening for ligand-receptor binding may then be performed by either removing individual detached ligand groups from the support (e.g., manually or by robotics), or more preferably, by performing an in situ assay for ligand-receptor binding (see You et al., *Chemistry & Biology* 4:969, 1997; and Schullek et al., *Analytical Biochemistry* 246:20, 1997).

In situ assays produce a visible activity that co-localizes with ligand-receptor binding, revealing both binding and the bound ligand's reagent history simultaneously. In some embodiments, in situ assays take place in one or more polymeric films overlaid on the support. The polymeric films contain one or more receptors and/or indicator compounds in a polymer matrix comprising, for example, agarose, polyacrylamide, polyvinyl alcohol, polyvinyl alcohol modified with stilbazolium groups, or any other such polymer compatible with detecting binding of particular ligands and receptors. In some embodiments, the films will be photopatternable, and will typically swell when hydrated forming a polymeric gel. After either chemical or photolytic release from the support, ligands will diffuse into the surrounding gel matrix. If a particular group of ligands specifically binds the receptors in the gel, then a zone of activity will be visible around that group. Determining the position of the element will reveal the reagent history, or more preferably, the composition of the ligand in a straightforward fashion. In the case of a porous array, the position is readily determined by the landmark features of the array where individual ligand groups correspond to discrete porous layers.

In other embodiments, the surface between array elements is modified with an organosilane providing a differential surface tension between the surface and the individual array elements (see You et al., *Chemistry & Biology* 4:969, 1997). The surface tension causes an applied receptor solution to segregate into individual droplets, with each droplet adhering to a separate array element. Exposure to either light or chemicals releases the ligands into the droplet, which in preferred embodiments is a nanodroplet (i.e., on the order of $10^{-9}$ liter). The spatial segregation of droplets prevents the mixing of detached ligands from other array elements. As a result, each array element is assayed for ligand-receptor binding in the liquid-phase using an in situ assay mixture. One advantage of screening detached ligands directly in solution is that it avoids potential complications of a polymeric film. As such, it is potentially a more generally applicable method.

In another embodiment, screening for ligand-receptor binding may be performed in vivo using living cells in direct contact with the array surface. According to this embodiment, linkers are provided with photolabile or enzyme-cleavable groups, which enables removal of ligands by contact with elements that are compatible with living cells. The enzyme-cleavable group is preferably chosen so as to be substantially cleavable with enzymes secreted by living cells. Most preferably, the cell will secrete an enzyme that detaches the ligand from the array, permitting the ligand to subsequently diffuse into the cell and affect an internal biologic process (i.e., ligand-receptor binding occurs in vivo). For example, arrays of nucleobase polymers attached via protease-sensitive linkages may be used to conduct antisense experiments on cells growing in direct contact with the surface of the array. Ligand separation from the support is essential for transmigration of the ligand through the cell membrane. Cell-induced cleavage of the ligand also allows the separated ligands to remain co-localized with their site of attachment, and the cells in contact with that site. Co-localization is particularly advantageous when a phenotypic cellular assay is used to determine modulation of gene expression by a nucleobase polymer. In such an assay, determining the location of the phenotypic change determines the sequence of the nucleobase polymer affecting the change, as well as the base sequence of its putative intracellular target. By using articles comprising many thousands of unique nucleobase polymers, such an approach is extremely powerful in that a single experiment can potentially determine the effect of every single gene in an entire genome on a particular phenotype.

As noted above, certain ligands synthesized by the methods described herein may comprise a target receptor modifying group that detectably alters a bound receptor. Ligands that comprise such a modifying group may be used within methods for modifying a target receptor. Such methods comprise contacting an array comprising ligands that contain such a group with a target receptor, which may be isolated or present within a mixture. It will be apparent that such contact should be performed under conditions and for a time sufficient to permit the desired modification.

Alternatively, ligands may be used as reagents in chemical or enzymatic reactions, rather than only being the subject of analysis as described above. In some embodiments, the increased ligand surface densities of porous arrays will provide sufficient material to perform arrays of meaningful enzymatic reactions. For example, single nucleotide differences may be detected by polymerase extension of oligonucleotides arrayed on the porous support (see Nikiforov et al., *Nucleic Acids Res.* 22:4167, 1994; Shumaker et al., *Human Mutation* 7:346, 1996; Pastinen et al., *Genome Research* 7:606, 1997 and Lockley et al., *Nucleic Acids Res.* 25:1313, 1997). Alternatively, arrays of primer pairs may be used to conduct arrays of amplification reactions using, for example, PCR. In some embodiments, such enzymatic reactions might occur in situ in one or more polymeric films overlaid on the porous coating. Alternatively, enzymatic reactions may be performed separately by removing array elements to individual reaction vessels.

Still further applications of the invention include information storage, production of molecular-electronic devices, production of a stationary phase in microfabricated separation devices, photography, and immobilization of labeled and unlabeled cells, proteins, antibodies, lectins, nucleic acids, nucleic acid probes, polysaccharides and the like in a pattern on a surface.

In yet another embodiment, arrays provided herein may be used in preparative applications wherein ligand arrays attached to a substrate are used to isolate a complementary target receptor from a mixture of receptors using methods analogous to those above for screening for receptor binding. Within such methods, a composition comprising a target receptor is contacted with a ligand-array as provided herein, provided that at least one nucleobase attached to the array binds to the target receptor. Unbound components of the composition are then removed from the array. The target receptor may then be separated from the array by altering conditions such that ligand-receptor binding is diminished.

In other embodiments, ligands or bound receptors may be selectively isolated from the array using a photoresist layer as described in U.S. Pat. No. 6,159,681 entitled "Light-Mediated Method and Apparatus For the Regional Analysis of Biologic Material". Briefly, by establishing a photoresist layer over ligands of the array and/or bound receptors, it is possible to precisely irradiate regions of the photoresist to expose specific ligands and/or receptors. Exposed ligands or receptors may then be selectively isolated by detaching them according to methods described above. Once isolated, the detached material may be further analyzed using any of a variety of analytic methods.

There are a variety of assays, including diagnostic assays, that involve the hybridization of an antisense molecule to a target nucleic acid molecule, either isolated or present within a mixture of compounds. Arrays as provided herein may be used within such hybridization steps. Such arrays should contain attached antisense molecules (i.e., nucleobase polymers that specifically and detectably bind to nucleic acid molecules of complementary sequence under moderately stringent conditions). Ligands may, but need not, be detached from the surface either before or after hybridization. In general, such hybridization reactions should be performed under conditions that favor specific hybridization. Suitable conditions may be selected by those of ordinary skill in the art.

The following Examples are offered by way of illustration and not by way of limitation. Within these Examples, all operations were conducted at about ambient temperatures and pressures unless indicated to the contrary.

EXAMPLES

Example 1

Attachment of an Adhesive Layer

This Example describes the attachment of an adhesive layer to a glass substrate, prior to application of a porous coating.

An adhesive layer was prepared on a commercial glass microscope slide (Curtin-Matheson Scientific, Inc., Houston, Tex.). The adhesive layer was prepared from a clear sol obtained by hydrolyzing and aging tetraethoxysilane (Aldrich Chemical Company, Inc., Milwaukee, Wis.). To prepare the sol, a concentrated sol was first prepared by hydrolyzing 21.7 ml of tetraethoxysilane in 6.3 ml $H_2O$ and 0.7 ml 1N nitric acid at room temperature for approximately 1 hour, followed by aging at 4° C. for several days. The concentrated sol was diluted 50-fold with ethanol, and applied to one surface of the slide at an incline using a pipette. The solvent was allowed to evaporate at room temperature leaving an adhesive layer less than 1 µm thick, and a free adhesive surface. The layer was cured by placing the slide on a heating block at 110° C. to 120° C. for 15 minutes.

Examples 2–8

Preparation of Representative Porous Coatings

These Examples describe the preparation of representative porous coatings.

The porous coating was obtained from a liquid coating solution. The coating solutions were prepared as follows: Five grams of fumed silica ($SiO_2$) with a primary particle size of 500 Å (Degussa, Inc., Ridgefield Park, NJ) were dispersed in 100 ml of 95% ethanol (5% water). To this dispersion was added tetraethoxysilane (TEOS) monomer or polymer in an amount indicated in Table VIII. TEOS polymer was obtained as described in Example 1. Sufficient nitric acid was added to provide an acidity of from 2.0 to 4.2 pH units. Coating solutions that incorporated linker molecules further included 3-aminopropyltriethoxysilane (i.e., "APES", from Aldrich Chemical Company, Inc., Milwaukee, Wis.) or bis(2-hydroxyethyl)-3-aminopropyltriethoxysilane (i.e., "HAPES", from Gelest, Inc., Tullytown, Pa.) in amounts as indicated in Table VIII. The coating solutions thus formed were stirred in a plastic container at room temperature for greater than 24 hours. Subsequent to aging, the coating solutions were applied to an adhesive surface of glass slides prepared as described in Example 1. The coating solutions were applied at an incline using a Pasteur pipette producing substantially uniform liquid layers. The liquid layers were allowed to evaporate at room temperature leaving a series of continuous porous coatings from 1 µm to 4 µm thick. The layers were then cured by heating to 120° C. for 15 minutes. The series of porous coatings were evaluated with respect to film quality as summarized in Table VIII.

TABLE VII

| Example Number | TEOS, μmole/g silica | TEOS polymerized | Linker, μmole/g silica | pH | Age of Mix | Majority Solvent | Film Quality |
|---|---|---|---|---|---|---|---|
| 2 | 372 | yes | — | 3.6 | >24 hrs | 3-pentanone | uniform |
| 3 | 1860 | yes | — | 2.8 | >24 hrs | 3-pentanone | uniform[1] |
| 4 | 1860 | no | — | 2.8 | >24 hrs | ethanol | uniform[2] |
| 5 | 240 | no | — | 4.2 | >24 hrs | ethanol | uniform |
| 6 | 80 | no | HAPES, 160 | 4.0 | >24 hrs | ethanol | uniform |
| 7 | 180 | yes | APES, 60 | 2.0 | >24 hrs | ethanol | uniform |
| 8 | 180 | no | APES, 60 | 4.2 | 66 hrs | ethanol | uniform |

[1,2] Greater than 25 μm thick.

Table VIII illustrates that uniform porous coatings were obtained from coating solutions prepared by contacting silica particles with either hydrolyzed metal alkoxide (Examples 4 and 5), or with metal alkoxide polymers formed separately (Examples 2 and 3). Uniform porous coatings greater than 25 μm thick were formed from coating solutions containing different solvents as Examples 3 and 4 demonstrate with 3-pentanone and ethanol, respectively. Table VIII also illustrates that it is possible to obtain uniform porous coatings with attached linker molecules by incorporating linker molecules directly in the coating solution as in Examples 6, 7, and 8. Such coating solutions are sensitive to how the TEOS and linker copolymers are formed. As illustrated in Examples 7 and 8, the coating solution obtained by adding APES to TEOS polymers has a lower pH optimum for uniform film formation than the coating solution obtained by adding APES to TEOS monomers.

Examples 9–18

Comparative Coatings

These Examples illustrate the preparation of coatings in a manner similar to those in Examples 2–8, with modifications as summarized in Table IX. The coating solutions were applied to the adhesive surface of glass slides prepared as in Example 1, producing substantially uniform liquid layers. The liquid layers were allowed to evaporate at room temperature followed by curing at 120° C. for 15 minutes. The series of coatings were evaluated with respect to film quality as reported in Table IX.

separated at a macroscopic and microscopic level, demonstrating that a polymeric component, such as TEOS, is necessary to form uniform porous coatings with fumed silica particles. Examples 12, 13 and 18 demonstrate that insufficient aging of this coating solution leads to flocculated and separated porous coatings (compare with Examples 2, 3, 4, and 8). Insufficient aging presumably prevents extended polymer formation (Examples 12 and 18) and/or the attachment of extended polymers to silica particles (Example 13). Example 14 illustrates that even with sufficient aging, increasing the pH above about 7.0 pH units results in solution instability due to particle aggregation (compare with Example 5). Organoalkoxysilanes containing an amino moiety such as APES do not function as substitutes for TEOS, as shown in Example 15. It is recognized that APES forms less extended polymers than TEOS, possibly explaining its ineffectiveness. As illustrated, coating solutions made by the random copolymerization of TEOS and a linker molecule are sensitive to the order of polymerization (compare Examples 8 and 17), the relative stoichiometry of TEOS and linker molecule (compare Examples 6 and 16), and the pH of the mixture (compare Examples 7 and 17).

Example 19

Preparation of a Photopatterned and Fortified Porous Coating

This Example illustrates the patterning of a porous coating, and the application of a fortifying layer to a patterned porous coating.

A coating solution was prepared according to the procedure described in Example 5 above. The coating solution

TABLE IX

| Example Number | TEOS, μmole/g silica | TEOS polymerized | Linker, μmole/g silica | pH | Age of Mix | Majority Solvent | Film Quality |
|---|---|---|---|---|---|---|---|
| 9 | — | — | — | — | NA | ethanol | separated |
| 10 | — | — | — | — | NA | water | cracked |
| 11 | — | — | — | — | NA | 3-pentanone | separated |
| 12 | 1860 | no | — | 2.8 | <1 hr | 3-pentanone | flocculated |
| 13 | 744 | yes | — | 4.2 | <1 hr | ethanol | separated |
| 14 | 240 | no | — | >10 | >24 hrs | ethanol | clumped |
| 15 | — | — | APES, 60 | 4.1 | >24 hrs | ethanol | flocculated |
| 16 | 180 | no | HAPES, 60 | 4.0 | >24 hrs | ethanol | clumped |
| 17 | 180 | yes | APES, 60 | 4.1 | >24 hrs | ethanol | clumped |
| 18 | 180 | no | APES, 60 | 4.2 | 18 hrs | ethanol | separated |

[1] NA - not applicable.

All the Examples in Table IX yield coatings of inferior film quality compared to the Examples in Table VIII. Examples 9–11 produced coatings that were cracked or was applied to the adhesive surface of a glass slide prepared as in Example 1, producing a substantially uniform liquid layer. The liquid layer was allowed to evaporate at room temperature leaving a uniform porous coating. Curing was postponed until after photopatterning.

While working in a laminar flow hood illuminated by cool-white fluorescent lights shielded with Gold Shields™ (Imtec Products Inc., Sunnyvale, Calif.), AZ® 1512 positive photoresist (Hoechst Celanese™, Somerville, NJ) with a solids content of 26 weight percent was diluted three-fold with propylene glycol methyl ether acetate (PGMEA) and applied to the porous coating using a Pasteur pipette. The excess was allowed to drain onto a paper towel by positioning the slide vertically. The slide was then placed on a flat surface for approximately 10 minutes at room temperature to substantially evaporate the solvent, followed by soft-baking on a metal heating block at a temperature of from 90° C. to 100° C. for 10 to 15 seconds. The evaporated layer of photoresist substantially covered the porous coating.

The photoresist surface was brought into contact with a mask bearing a 16×16 array of 600 $\mu$m×600 $\mu$m opaque squares on a transparent background (Precision Image Corporation, Redmond, Wash.). The opaque squares were separated from one another by 200 $\mu$m. The mask was exposed to 365 nm light at an energy density of 8 mW/cm$^2$ for 90 seconds using a UV transilluminator (UVP Inc., Upland, Calif.).

With the photoresist appropriately irradiated, the entire substrate was immersed in AZ® 351 developer diluted six-fold with distilled water (Hoechst Celanese™, Somerville, N.J.). The photoresist in irradiated regions and the porous coating within it were both completely removed from the substrate surface after about 60 to 120 seconds in developer. The temporal progress of dissolution was visually monitored by the formation of red dye from irradiated regions during the development process. After development, the entire substrate was rinsed with distilled water, and allowed to air-dry. Unirradiated photoresist was stripped by immersion in acetone followed by an acetone rinse and evaporation. Stripping of unirradiated photoresist left a patterned porous coating comprising a 16×16 array of porous squares.

Figure 2:
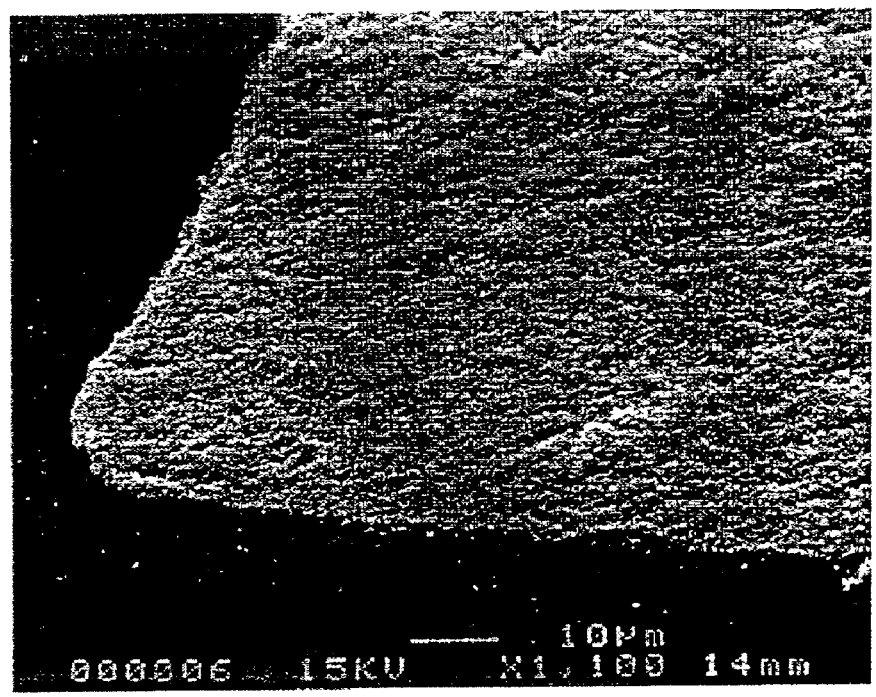
FIG. 2 is a scanning electron microscope print at a magnification of 1,100× that shows a portion of a patterned porous coating according to the present invention. The scale-bar at the bottom of the print is 10 µm long.

FIG. 2 is a scanning electron microscope print of the patterned porous coating at a magnification of 1,100×, showing a corner of one porous square. As shown, the porous square has a continuous porous coating (i.e., the coating covers the surface of the substrate with virtually no discontinuities or gaps), which is uniformly 2 $\mu$m thick. FIG. 3 is a scanning electron microscope print of the porous coating in FIG. 2 at a magnification of 95,000×. At very high magnification, the porous coating is shown to be comprised of a rigid and continuous network of silica particles with an extensive surface area wherein the average pore size approximates the primary particle size.

A fortifying solution was applied as a separate coating after photopatterning to further anchor the elements of the porous coating without substantially filling the pore volume. The fortifying solution was a 150-fold ethanol dilution of the concentrated sol prepared in Example 1. The fortifying solution was applied to the patterned porous coating at an incline using a pipette. The solvent was allowed to evaporate at room temperature followed by curing at 110° C. to 120° C. for 15 minutes.

This Example demonstrates that the porous coatings of the present invention can be (1) tailored to have a particular average pore size by choosing an appropriate primary particle size, (2) photopatterned with high sensitivity (AZ® 1512 positive photoresist has a photospeed of 58 mJ/cm$^2$) and (3) photopatterned using microfabrication techniques.

Example 20

Attachment of Linker Molecules

This Example illustrates the attachment of linkers to a patterned porous coating prepared as described in Example 19.

The coating was immersed in AZ® 351 developer diluted six-fold with distilled water for 15 seconds, and rinsed with distilled water. Linker molecules were coupled to the coating surface by immersing the coating in a 2% solution of an organoalkoxysilane in ethanol-H$_2$O (95:5) for 10 minutes, followed by rinsing with ethanol and curing at 120° C. for 15 minutes. The coating was again immersed in AZ® 351 developer for 15 seconds, rinsed with distilled water, and dried. The basic aqueous developer deprotinates surface silanol and amino groups, facilitating subsequent process steps. Patterned porous coatings with attached amino-linker molecules (i.e., amino reactive group) and hydroxyl-linker molecules (i.e., hydroxyl reactive group) were obtained by using APES and HAPES, respectively, as the organoalkoxysilane.

Example 21

Ligand Surface Density: Comparative Example

This Example illustrates, for comparative purposes, ligand surface density on a substrate having a porous coating, as compared to the density on a substrate lacking a porous coating.

A substrate lacking a porous coating was coupled with amino-linker molecules using the method described in Example 20. Using an appropriately patterned photoresist layer applied to the surface, the amino-linker molecules were reacted with fluorescein isothiocyanate (FITC) in a specific pattern comprising a 16×16 array of 600 $\mu$m×600 $\mu$m squares. This FITC-labeled slide served to demonstrate the ligand surface density provided by the prior art (for representative reference, see Fodor et al., *Science* 251:767, 1991).

While working under light greater than 500 nm, PVA-SBQ photoresist was applied to the linker-modified slide surface as a thin liquid layer. The liquid layer was baked on a metal heating block at a temperature of from 90° C. to 100° C. for 15 seconds leaving a 1–2 $\mu$m thick photoresist film. PVA-SBQ photoresist is a previously described negative photoresist derived from stilbazolium (SBQ) substituted polyvinyl alcohol (PVA) (see Ichimura et al., U.S. Pat. No. 4,891,300). Irradiated regions of the photoresist undergo a light-induced cross-linking of SBQ groups rendering those regions insoluble in an aqueous developer. PVA-SBQ photoresist was chosen as the photopatternable barrier layer because the light-induced cross-linking of SBQ groups is chemically inert with regard to the underlying amino-linker molecules. The PVA-SBQ composition used to coat the linker-modified slide comprised 0.8% PVA-SBQ and 0.025% Triton X-100 in 70% ethanol and 30% water.

The surface of the photoresist film was brought into contact with a mask bearing a 16×16 array of 600 $\mu$m×600 $\mu$m opaque squares on a transparent background. The opaque squares are separated from one another by 200 $\mu$m. The mask was exposed to 365 nm light at an energy of 8 mW/cm$^2$ for 7 seconds using a UV transilluminator (UVP Inc., Upland, Calif.).

With the photoresist appropriately irradiated, the entire substrate was immersed in distilled water which dissolved unirradiated regions of the PVA-SBQ photoresist leaving a cross-linked photoresist layer with a 16×16 array of square openings to the underlying substrate surface and the attached amino-linker molecules. The remaining surface was blocked by a barrier layer comprising the cross-linked photoresist layer.

The FITC coupling reaction was performed by immersing the slide in 0.1 mM FITC in acetonitrile for 5 minutes at room temperature followed by acetonitrile and acetone washes. Because of the patterned barrier layer on the surface of the slide, FITC only coupled to the surface in a pattern corresponding to the 16×16 array of square openings. After FITC coupling, the cross-linked photoresist layer was stripped by immersing the slide in a 0.75% aqueous solution of sodium periodate ($NaIO_4$) for 30 seconds (i.e. solubilizes the film by cleaving 1,2-diol units in the PVA). The slide was then washed with water and dried.

The fluorescence image of the FITC-labeled slide was captured at three different magnifications using a 35 mm camera attached to a Standard Epifluorescence Microscope (Carl Zeiss, Thornwood, N.Y.). Using an exposure time of 15 seconds, the fluorescence image of the square array was faint at objective magnifications of 10× and 20×, and barely visible at an objective magnification of 2× (see FIGS. 4A, 4C and 4E).

A patterned porous coating was prepared as described ill Example 19, and coupled with amino-linker molecules using the method described in Example 20. The amino-linker molecules of the porous coating were reacted with fluorescein isothiocyanate (FITC) which forms a covalent linkage with the amino group of the linker molecules. This FITC-labeled porous coating was utilized to demonstrate the increase in ligand surface density provided by the present invention.

The FITC coupling reaction was performed by immersing the linker-modified porous coating in 0.1 mM FITC in acetonitrile for 5 minutes at room temperature followed by acetonitrile and acetone washes. The fluorescence image of the FITC-labeled porous coating was captured at three different magnifications using a 35 mm camera attached to a Standard Epifluorescence Microscope. Using an exposure time of 15 seconds, the fluorescence image of the patterned porous coating is readily visible using objective magnifications of 2×, 10×, and 20× (see FIGS. 4B, 4D and 4F).

This example demonstrates that (1) compared with the image intensity of the prior art, the present invention provides a marked increase in ligand surface density, (2) imaging of ligands on the patterned porous coating is rapid and economical using standard equipment, (3) the patterned porous coating is compatible with methods of solid-phase synthesis, and (4) the porous coating does not swell or distort during solid-phase synthesis.

Example 22

Specific Binding of a DNA-ligand by a DNA-receptor

DNA-ligands were synthesized on the surface of a patterned porous coating using solid-phase synthesis in order to demonstrate that a DNA-receptor specifically binds to a complementary surface-bound DNA-ligand. A patterned porous coating was prepared as described in Example 19, and coupled with hydroxyl-linker molecules using the method described in Example 20.

A reactor system was formed by mating the slide to a polytetrafluoroethylene (i.e., PTFE, marketed as TEFLON®) reactor base with an intervening PTFE gasket. Sandwiched together, the slide, gasket, and base formed a sealed reactor cavity except for inlet and outlet ports in the reactor base as shown in FIG. 1E. The reactor cavity had a volume of 300 μl and the patterned porous coating was fully contained with the cavity. The reactor system allowed chemical reagents to be delivered over the patterned porous coating either manually or automatically by connecting the inlet and outlet ports to either syringes or a reagent delivery machine, respectively. In this example, the inlet and outlet ports were connected to a PCR-Mate® automated DNA synthesizer (Applied Biosystems, Inc., Foster City, Calif.).

Using the DNA synthesizer to automatically deliver reagents, the DNA-ligand with the sequence 5'-GCCTACGC-3' was synthesized via eight phosphoramidite couplings on the exposed hydroxyl groups beginning with the 3' end. Following synthesis, the reactor system was separated from the DNA synthesizer, and the phosphate and exocyclic amine protecting groups removed by manually applying 0.05 M potassium carbonate in methanol to the reactor cavity for 2 hours at room temperature. The strongly basic conditions (i.e., concentrated ammonium hydroxide) ordinarily used to deprotect DNA after solid-phase synthesis were avoided because of the possibility of cleaving the siloxane bonds connecting the linker molecules to the substrate surface. Instead, deprotection was accomplished using the mildly basic conditions described above by using phenoxyacetyl (Pac) protected dA, 4-isopropyl-phenoxyacetyl (iPr-Pac) protected dG, and acetyl protected dC (Glen Research, Inc., Sterling, Va.).

Following deprotection, the slide was separated from the reactor base and visualized using fluorescence microscopy without the application of a labeled receptor. The image was captured using a 35 mm camera attached to a Standard Epifluorescence Microscope (Carl Zeiss, Thornwood, N.Y.). As shown in FIG. 5, the fluorescence image and corresponding surface plot of the porous coating reveal no detectable background fluorescence.

Figure 5A:
FIGS. 5A–5F are prints (FIGS. 5A, 5C and 5E) and surface plots (FIGS. 5B, 5D and 5F) from an epifluorescence microscope that demonstrate specific binding of ligand by a fluorescently labeled receptor on a representative patterned porous coating, wherein both the ligand and receptor are DNA. The ligand was synthesized on the patterned porous coating by solid-phase synthetic methods. The receptor used was: no receptor (FIGS. 5A and 5B), FTA (FIGS. 5C and 5D) or FAA (FIGS. 5E and 5F).
Figure 5B:
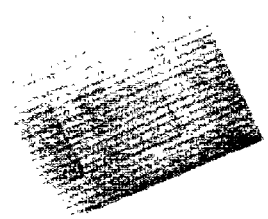
Figure 5C:
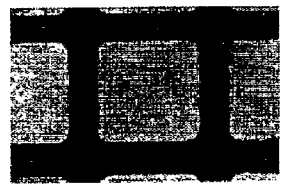
Figure 5D:
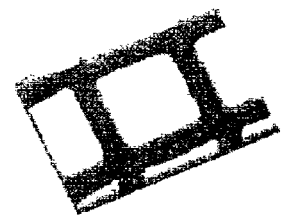

To demonstrate the availability of surface-bound DNA for hybridization with a complementary DNA-receptor, 20 μl of 10 μM 5'-GCGTAGGC-fluorescein "FTA" in FIGS. 5C and 5D) suspended in 6×SSPE was applied to the porous surface and incubated for an hour at a temperature of 4° C. The 6×SSPE solution is a high-salt buffer with a pH of 7.4 comprising 1M NaCl, 66 mM $NaH_2PO_4/Na_2HPO_4$, 6 mM EDTA, and 0.05° Triton X-100-™ The slide was subsequently washed in 6×SSPE at a temperature of 15° C., and mounted on a modified microscope stage attached to a Standard Epifluorescence Microscope The stage contained an aqueous gel within its interior that was chilled to approximately 4° C. prior to image acquisition. The fluorescence image of FTA hybridized to the porous coating was captured using a 35 mm camera attached to the microscope. Using an exposure time of 15 seconds, the fluorescence image of the hybridized DNA-receptor was readily visible using an objective magnification of 10× (see FIGS. 5C and 5D and corresponding surface plot). The bound DNA-receptor was dissociated from the ligand-DNA by immersing the slide in 45° C. water, and the hybridization repeated. This cycle of thermal dissociation and hybridization was repeated at least 20 times with no loss in the fluorescence intensity from bound FTA, demonstrating the stability of the DNA-ligand attachment.

Figure 5E:
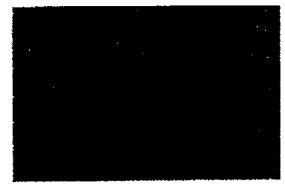
Figure 5F:
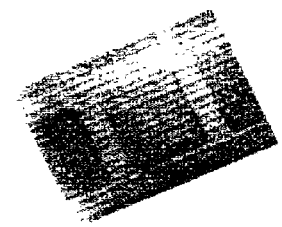

To demonstrate the sequence specificity of DNA hybridization, FTA was thermally dissociated from the porous surface and 20 μl of 10 μM 5'-GCGAAGGC-fluorescein "FAA" in FIGS. 5E and 5F; FAA differs from FTA at the underlined base) suspended in 6×SSPE was applied to the porous surface and incubated for an hour at a temperature of 4° C. Following hybridization, the slide was washed in 6×SSPE at a temperature of 15° C. and mounted on the modified stage as described above. The fluorescence image of the FAA hybridization was captured with the 10× objective of a Standard Epifluorescence Microscope with attached 35 mm camera. The fluorescence image and corresponding surface plot of the FAA hybridization reaction are shown in FIGS. 5E and 5F (exposure time of 15 seconds). Although FTA and FAA differ by only a single base, hybridization is highly specific with the images of FAA hybridization equivalent to the images with no receptor.

This example demonstrates that (1) the porous coating provides a successful substrate for performing solid-phase synthesis, (2) the porous coating has low autofluorescence, (3) the porous coating provides an increased DNA-ligand surface density, (4) surface-bound DNA-ligands are available for DNA-receptor binding, (5) imaging of labeled receptors on the patterned porous coating is rapid and economical using standard equipment, and (6) the porous coating provides a substrate capable of detecting the specific binding characteristic of macromolecular receptors.

Example 23

Specific Binding of a PNA-array by a DNA-receptor

This Example illustrates the specific binding of a DNA-receptor to a complementary member of a PNA-array comprising 16 different PNA sequences on the surface of a patterned porous coating.

A PNA array comprising 16 different PNA sequences was synthesized on the surface of a patterned porous coating as described above. The PNA array was synthesized using solid-phase synthesis and methods more fully described in co-pending Application Ser. No. 09/326,479 entitled, "Methods and Compositions for Performing an Array of Chemical Reactions on a Support Surface" and U.S. Pat. No. 6,569,598 entitled "Solvent-Resistant Photosensitive Compositions," incorporated herein by reference. All PNA reagents were from PerSeptive Biosystems, Inc. (Framingham, MA). PNA sequences with protecting groups on the exocyclic amines are indicated by the base designations A, G, C, and T to distinguish them from deprotected sequences which use A, G, C, and T as base designations.

A patterned porous coating comprising a 4×4 array of 600 μm×600 μm porous squares was prepared as described in Example 19, and coupled with amino-linker molecules using the method described in Example 20. The PNA-array was then synthesized on the surface of the patterned porous coating with each array element occupying one 600 μm×600 μm porous square. Each element of the array comprised one of the 16 possible combinations of the sequence, linker-spacer-CGN$_1$N$_2$TCCG-NH$_2$, where N$_1$ and N$_2$ may independently be A, G, C, or T. The position of each element in the array, as referenced by the N$_1$N$_2$ sequence, is shown in the array schematics of FIGS. 6A and 6B. The shaded grid in each schematic indicates the array element that is complementary to the receptor sequence above each schematic. The portions of the DNA-receptors complementary to the corresponding N$_1$N$_2$ sequence are underlined.

The PNA-array was synthesized by first attaching the sequence, linker-spacer-CG-NH-Fmoc to all porous squares by manually applying reagents using the reactor system described in Example 22. (Fmoc: fluorenylmethyloxycarbonyl, a base-labile amino-protecting group removed under nonhydrolytic conditions). The spacer is Fmoc-AEEA-OH, a molecule with the following formula:

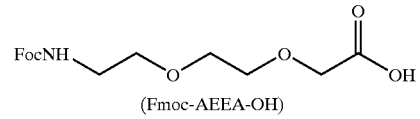

(Fmoc-AEEA-OH)

The spacer was coupled to the free amino group of the linker molecules by two 120 μl applications of a solution comprising 72 mM Fmoc-AEEA-OH, 60 mM HATU, 100 mM 2,6-lutidine, and 66 mM DIPEA in 33% NMP and 66% DMF. The linker molecules were incubated with the spacer solution for 30 to 40 minutes, followed by a DMF rinse. Unreacted linker molecules were then capped from further reaction by applying a solution comprising 10% acetic anhydride and 10% 2,6-lutidine in tetrahydrofuran for 5 minutes. The reactor cavity was flushed with DMF, and the Fmoc protecting groups removed with 1 ml of 20% piperidine in DMF flowed continuously through the reactor cavity over 10 minutes to drive the reaction to completion. The C monomer was then coupled to the free amino group of the spacer using the coupling conditions described above. Capping and Fmoc removal led to the sequence, linker-spacer-C—NH$_2$. This sequence was coupled with the G monomer and capped, but not deprotected. This provided the sequence, linker-spacer-CG-NH-Fmoc.

The N$_1$N$_2$ sequence was next added using a series of photopatterned barrier layers consisting of the positive photoresist described in U.S. Pat. No. 6,569,598 entitled "Solvent Resistant Photosensitive Compositions." Two main properties of the positive photoresist make it particularly useful as a barrier layer during solid-phase synthesis. First, it is resistant to many organic solvents that are used in organic reactions. Second, irradiated regions of the photoresist undergo a photochemical reaction that is inert with respect to chemical species attached to the underlying surface. Using a series of 8 patterned photoresist layers applied to the surface, two layers of PNA monomers were selectively applied to the patterned porous coating creating one of the 16 possible combinations of the sequence, linker-spacer-CGN$_1$N$_2$—NH-Fmoc at each porous square.

In detail, a photoresist layer was established on the porous support bearing the sequence, linker-spacer-CG-NH-Fmoc at all porous squares. The surface of the photoresist film was brought into contact with an opaque mask bearing a transparent rectangle comprising the rectangular region occupied by the first column of four porous squares. The mask was exposed to 365 nm light at an energy density of 8 mW/cm$^2$ for 10 minutes using a UV transilluminator. With the photoresist appropriately irradiated, the entire substrate was immersed in developer which dissolved the irradiated region leaving a photoresist layer with a rectangular opening to the first column of porous squares. The slide was attached to the reactor base, and the region encompassing all porous squares was exposed to 20% piperidine in toluene as described above. Because of the patterned barrier layer on the surface of the slide however, piperidine removed Fmoc only from the first column of porous squares. The slide was detached from the reactor base, and the photoresist layer stripped with an organic solvent.

The slide was reattached, and the entire array of porous squares contacted with A monomer using the conditions described above. The A monomer only coupled to the first column of porous squares where Fmoc was selectively removed. Following capping, another photoresist layer was established, and irradiated in a region comprising the second column of porous squares. The second column of porous squares was selectively deprotected and coupled with G monomer as described above. This process was repeated for the third and fourth columns using C and T monomers, respectively.

After the application of these 4 patterned barrier layers, the $N_1$ layer was completed creating one of the four sequences, linker-spacer-CGN$_1$—NH-Fmoc, at each column. The $N_2$ layer was completed similarly, except that the transparent rectangle of each of the 4 masks comprised the region occupied by a row of four porous squares. With the $N_2$ layer completed, all Fmoc groups were removed and the remaining sequence synthesized by successively coupling T, C, C, and G monomers to all porous squares. The exocyclic amine groups in this example utilized Bhoc (benzhydryloxycarbonyl) protection, which allows short deprotection times. Accordingly, the exocyclic amine protecting groups were removed by a 10 minute incubation with 25% m-cresol in TFA. Deprotection gives the 16 element PNA-array, with each porous square comprising a single element of the sequence, linker-spacer-CGN$_1$N$_2$TCCG-NH$_2$. As an example of PNA-array elements expressed in terms of reagent history, the "CT" and "CA" elements in the schematic may be written as follows:

CT: S-[APES]-[Fmoc-AEEA-OH]-[cap]-[pip]-[C]-[cap]-[pip]-[G]-[cap]-[A]-[G]-[pip]-[C]-[T]-[pip]-[T]-[C]-[G]-[A]-[pip]-[T]-[pip]-[C]-[pip]-[C]-[pip]-[G]-[TFA]

CA: S-[APES]-[Fmoc-AEEA-OH]-[cap]-[pip]-[C]-[cap]-[pip]-[G]-[cap]-[A]-[G]-[pip]-[C]-[T]-[T]-[C]-[G]-[pip]-[A]-[pip]-[T]-[pip]-[C]-[pip]-[C]-[pip]-[G]-[TFA]

where "cap" is the capping reagent, "pip" is the Fmoc removal reagent, and T, C, G, and A are Fmoc and Bhoc protected monomer coupling reagents.

To demonstrate the specificity of DNA hybridization to the PNA-array, 10 μM FAA in 6×SSPE was applied to the porous surface and incubated for 10 minutes at room temperature, followed by a brief room temperature wash in 6×SSPE. The fluorescence image of the porous coating was captured at room temperature using a 35 mm camera attached to a Standard Epifluorescence Microscope. The fluorescence image of FAA bound at the predicted array element is readily detected and visualized using an objective magnification of 10× and an exposure time of 15 seconds (see FIG. 6 and corresponding surface plot). Although six of the array elements differ from the "CT" element by only a single base, FAA hybridizes specifically to its complementary PNA sequence with little or no signal from other array elements.

Bound FAA was dissociated from the PNA-array by immersing the slide in 90° C. water, and the hybridization repeated with FTA using conditions as described above for FAA. The fluorescence image of the FTA hybridization was captured with the 10× objective of a Standard Epifluorescence Microscope with attached 35 mm camera. The fluorescence image and corresponding surface plot are shown in FIG. 6 (exposure time of 15 seconds). As with FAA, FTA hybridizes specifically to its complementary PNA sequence with little or no signal from other array elements.

This Example demonstrates that (1) the porous coating provides a successful substrate for performing solid-phase synthesis of ligand arrays, (2) the porous coating provides an increased PNA-ligand surface density, (3) surface-bound PNA-ligands are available for DNA-receptor binding, (4) imaging of labeled receptors on the patterned porous array is rapid and economical using standard equipment, and (5) the porous coating provides a substrate capable of detecting the specific binding characteristic of macromolecular receptors. This Example further demonstrates the advantages of PNA arrays over DNA arrays including more rapid hybridization (10 minutes versus 60 minutes for DNA), greater specificity, and more convenient hybridization conditions (i.e., hybridization of short probes at room temperature).

The Example also illustrates the advantage of synthesizing a PNA array directly on the support used for screening, as opposed to applying an array of presynthesized PNA molecules to a support. While PNA molecules are readily synthesized on a solid-phase, many sequences aggregate after being cleaved from the support. By synthesizing the PNA array directly on the porous support, aggregation and issues of solubility are avoided. As a result, the disclosed PNA arrays do not have the sequence or length restrictions typically encountered with solution-phase hybridization of PNA with DNA.

Example 24

An Array of Weakly Inhibitory Drug Analogues: Synthesis and Screening

This Example illustrates the preparation of an array comprising nine analogues of enalaprilat, in order to demonstrate the efficacy of the method for synthesizing and screening arrays bearing low-molecular-weight compounds characteristic of drugs, herbicides, and pesticides. Enalaprilat is one of a class of antihypertensives that bind angiotensin-converting enzyme (ACE) and inhibit its dipeptidase activity. ACE generates the powerful vasoconstrictor substance angiotensin II by removing the C-terminal dipeptide from the precursor decapeptide angiotensin I. Enalaprilat is a dipeptide analogue with the following formula:

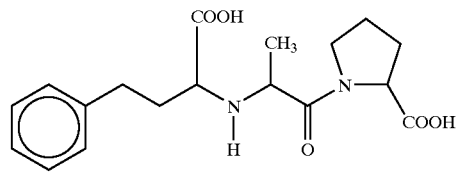

It is thought that enalaprilat is a transition-state inhibitor with the CHCO$_2$H and NH groups mimicking the transition state-like geometry attained at the scissile peptide bond of angiotensin I (see Patchett et al., *Science* 288:280, 1980). The enalaprilat array was synthesized using solid-phase synthesis and a series of patterned barrier layers. The reagents were from PerSeptive Biosystems, Inc. (Framingham, MA) except for the α-keto acids which were from Aldrich Chemical Company, Inc., (Milwaukee, Wis.). All amino acids were L-amino acids.

A patterned porous coating comprising a 3×3 array of 1600 μm×1600 μm porous squares was prepared as described in Example 19, and coupled with amino-linker molecules using the method described in Example 20. The enalaprilat array was then synthesized on the surface of the patterned porous coating with each array element occupying one 1600 μm×1600 μm porous square. Each element of the array comprised one of the nine combinations of compounds with the following formula:

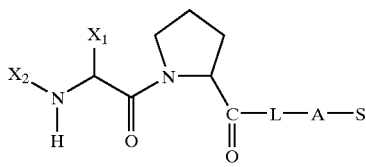

where $X_1$ may be $X_{1a}$, $X_{1b}$, or $X_{1c}$, and $X_2$ may be $X_{2a}$, $X_{2b}$, or $X_{2c}$ (see Table X).

TABLE X

| $X_1$ Groups | $X_2$ Groups |
| --- | --- |
| $X_{1a}$ = —$CH_3$ | $X_{2a}$ = (COOH-CH2-phenyl) |
| $X_{1b}$ = (C(=O)-CH2-NH-(trityl)) | $X_{2b}$ = (COOH-CH2-phenyl-NO2) |
| $X_{1c}$ = —O-(tert-butyl) | $X_{2c}$ = (COOH-CH2CH2-COOH) |

Within each element, S is the porous surface, A is aminopropyltriethoxysilane, and L is an acid-labile linker with the following formula:

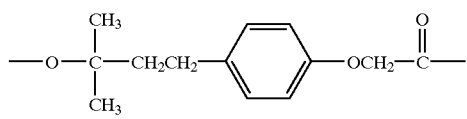

where the tertiary oxygen forms an ester with an enalaprilat analogue, and the carbonyl forms an amide with aminopropyltriethoxysilane. A C-terminal dipeptide may be lost during Fmoc-based solid-phase synthesis through diketopiperazine (DKP) formation (see Gisin and Merrifield, J. Amer. Chem. Soc. 94:3102, 1972). The intramolecular aminolysis leading to DKP is particularly accelerated when the C-terminal residue is proline as occurs in the synthesis of enalaprilat analogues. Intramolecular aminolysis and DKP formation were sterically suppressed by connecting proline to the support via an ester of a tertiary alcohol as shown above. The tertiary alcohol was 4-(1',1'-dimethyl-1'-hydroxypropyl)phenoxyacetyl (DHPP; a kind gift from Jan Kochansky, USDA (Beltsville, MD)) as described by Akaji et al., J. Chem. Soc., Chem. Commun. 584, 1990 and Kochansky and Wagner, Tetrahedron Lett. 33:8007, 1992).

The analogue array was synthesized by first attaching the sequence, S-A-L-Pro-Fmoc to all porous squares by manually applying reagents using the reactor system described in Example 5. DHPP was coupled to the free amino group of A by applying a solution comprising 104 mM DHPP, 93 mM HOAt (1-hydroxy-7-azabenzotriazole), and 105 mM DIPCDI (N,N-diisopropylcarbodiimide) in DMF. Coupling was performed by applying three 100 μl aliquots of the above solution to the reactor cavity over the course of 180 minutes. The reactor cavity was then flushed with DMF, and the tertiary alcohol group of DHPP esterified with 100 mM FMOC-Pro-Cl in pyridine-dichloroethane (1:4) for 20 hours. FMOC-Pro-Cl is the acid chloride of FMOC-Pro prepared from thionyl chloride according to previously published methods (see Carpino et al., J. Org. Chem. 51:3732, 1986). The low reactivity of the tertiary alcohol group requires an acid chloride for efficient coupling of Fmoc-Pro to DHPP.

The $X_1$ and $X_2$ groups were next added using a series of photopatterned barrier layers consisting of the positive photoresist described in U.S. Pat. No. 6,569,598 entitled "Solvent-Resistant Photosensitive Compositions." The positive photoresist is particularly useful as a barrier layer during solid-phase synthesis because it is resistant to many organic solvents, and irradiated regions of the photoresist undergo a photochemical reaction that is inert with respect to chemical species attached to the underlying surface. Using a series of 6 patterned photoresist layers applied to the surface, two layers of chemical reagents were selectively applied to the patterned porous coating creating one of the above enalaprilat analogues at each porous square. Using a series of 6 patterned photoresist layers applied to the surface, two layers of chemical reagents were selectively applied to the patterned porous coating creating one of the above enalaprilat analogues at each porous square.

In detail, a photoresist layer was established on the porous support bearing the sequence, S-A-L-Pro-Fmoc at all porous squares. The surface of the photoresist film was brought into contact with an opaque mask bearing a transparent rectangle comprising the rectangular region occupied by the first column of three porous squares. The mask was exposed to 365 nm light at an energy density of 8 mW/cm² for 10 minutes using a UV transilluminator. With the photoresist appropriately irradiated, the entire substrate was immersed in developer which dissolved the irradiated region leaving a photoresist layer with a rectangular opening to the first column of porous squares. The slide was attached to the reactor base, and the region encompassing all porous squares was exposed to 20% piperidine in toluene as described above. Because of the patterned barrier layer on the surface of the slide however, piperidine removed Fmoc only from the first column of porous squares. The slide was detached from the reactor base, and the photoresist layer stripped with an organic solvent.

The slide was reattached, and the entire array of porous squares contacted with a solution comprising 233 mM Fmoc-Alanine-OH, 233 mM HATU, and 458 mM DIPEA in DMF. The solution was incubated with the porous surface for 60 minutes, followed by two DMF flushes of the reactor cavity. The Fmoc-Alanine-OH monomer only coupled to the first column of porous squares where Fmoc was selectively removed. Following coupling, another photoresist layer was established, and irradiated in a region comprising the second column of porous squares. The second column of porous squares was selectively deprotected and coupled with Fmoc-Asparagine(trityl)-OH as described above (i.e., trityl protected monomer). This process was repeated for the third column using Fmoc-Serine(tert-butyl)-OH (i.e., tert-butyl protected monomer).

After the application of these patterned barrier layers, the $X_1$ layer was completed creating one of three compounds at each column with the following formula:

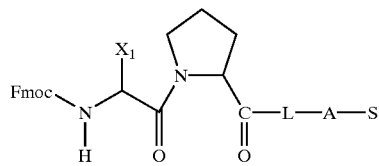

The $X_2$ layer was attached using similar barrier layers, except that the transparent rectangle of each of the next 3 masks comprised the region occupied by a row of three porous squares rather than a column. The $X_2$ layer was formed by reductive alkylation of the deprotected amino group with an α-keto acid selected from the group consisting of phenylpyruvic acid, 2-nitrophenylpyruvic acid, and 2-ketoglutaric acid. Each $X_2$ coupling comprised contacting the entire array of porous squares with a solution of 250 mM α-keto acid and 400 mM $NaBH_3CN$ in acetic acid-DMF (1:99) for 24 hours.

With the $X_2$ layer completed, a polymeric binder was added to the porous array by applying and evaporating a thin liquid layer of 1% polyvinyl alcohol in ethanol-$H_2O$ (1:3). Each of the porous squares was then removed from the substrate using a razor blade and placed in separate tubes. The polymeric binder prevented fragmentation of the porous network during removal. To each tube was added 200 μl of $H_2O$ followed by centrifugation. The supernatant contained solubilized polymeric binder and was discarded. To each pellet of porous material was added 20 μl of TFA-$H_2O$ (95:5) to cleave the analogues from the support, and remove tert-butyl and trityl protecting groups. After 2 hours of incubation, the TFA-$H_2O$ was removed under vacuum leaving a residue in each tube that contained one of nine enalaprilat analogues with the following general formula:

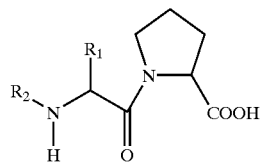

where $R_1$ and $R_2$ are the groups defined in Table XI. Each analogue was then dissolved in 50 μl of 50 mM Tris buffer (pH 8.3) containing 300 mM NaCl. As an example of an analogue expressed in terms of reagent history, the "$R_{1a}$+$R_{2a}$" analogue from the array may be written as follows:

$R_{1a}$+$R_{2a}$: S-[APES]-[DHPP]-[FMOC-Pro-Cl]-[pip]-[Fmoc-Alanine-OH]-[Fmoc-Asparagine(trityl)OH]-[Fmoc-Serine(tert-butyl)-OH]-[pip]-[phenylpyruvic acid+$NaBH_3CN$]-[2-nitrophenylpyruvic acid+$NaBH_3CN$]-[2-ketoglutaric acid+$NaBH_3CN$]-[PVA]-[$H_2O$]-[TFA-$H_2O$]

TABLE XI

| $R_1$ Groups | $R_2$ Groups |
|---|---|
| $R_{1a}$ = —$CH_3$ | $R_{2a}$ = (COOH-substituted benzyl) |

TABLE XI-continued

| $R_1$ Groups | $R_2$ Groups |
|---|---|
| $R_{1b}$ = (acetyl-$NH_2$) | $R_{2b}$ = (COOH-substituted 2-nitrobenzyl) |
| $R_{1c}$ = —OH | $R_{2c}$ = (dicarboxylic acid) |

Each enalaprilat analogue was screened for ACE inhibitory activity in a functional assay using the substrate furylacryloylphenyalanylglycylglycine (i.e., FAPGG, Sigma Chemical Co., St. Louis, Mo.). Hydrolysis of FAPGG by ACE results in a decrease in absorbance at 328 nm which can be used to calculate initial enzyme velocities in the presence and absence of enalaprilat analogues. Each assay mixture contained 10 nM ACE, 50 μM FAPGG, 50 mM Tris (pH 8.3), 300 mM NaCl, and 20–40 μl of each of the above analogue solutions in a total reaction volume of 50 μl. The above mixture without analogue served as the negative control for inhibitory activity. A positive control was made by adding 250 nM of the potent inhibitor, lisinopril ($IC_{50}$= 1.2 nM). Each reaction was initiated by adding 5 μl of 500 μM FAPGG to 45 μl of the remaining assay components in a 100 μl cuvette. The temporal progress of each reaction was monitored by measuring the absorbance at 328 nm every 15 seconds. The negative control had an average initial velocity of 1220 $min^{-1}$, which compares favorably with the $K_m$ and $k_{cat}$ values reported previously for FAPGG (see Holmquist et al., Analytical Biochem 95:540, 1979). The positive control had zero initial velocity.

The percent ACE inhibition of each analogue according to its position in the array is shown in the surface plot of FIG. 7B. The percent ACE inhibition is expressed as the percent decrease in initial velocity relative to the initial velocity of the negative control. The composition of each enalaprilat analogue in the surface plot may be determined using the array schematic of FIG. 7A. Compositions are referenced by $R_1$ and $R_2$ groups as defined in Table XI. The shaded grid indicates the array element with the highest percent ACE inhibition. The $R_{1a}$+$R_{2a}$ compound has only moderate binding affinity ($IC_{50}$=39 nM) compared to enalaprilat ($IC_{50}$=4.5 nM) as reported by Patchett et al., Science 288:280, 1980). Despite its moderate binding affinity, the porous coating of the present invention provided sufficient ligand surface density to detect inhibition of ACE by this compound.

The ligand surface density was calculated for the $R_{1a}$+$R_{2a}$ compound using the known $IC_{50}$ and the percent inhibition shown in FIG. 7B. Based on 35 percent inhibition from a 1 μm thick porous coat, the $R_{1a}$+$R_{2a}$ compound had a calculated surface density of $1.0 \times 10^{-17}$ mole/$μm^2$. This is a minimum value since the calculation does not account for losses due to inefficient coupling, deprotection, or cleavage. Even with this caveat, the value is in agreement with the expected range of $0.2 \times 10^{-17}$ mole/$μm^2$ to $4.6 \times 10^{-17}$ mole/$uM^2$ predicted from reported HAPES and APES surface densities (see Chee et al., Science 274:610, 1996 and Fodor et al., U.S. Patent No. 5,510,210). This is equivalent to a ligand concentration in the porous coating of from 0.002 M to 0.040 M. Compare this with the ligand concentration in a polymeric support (e.g., Tenta gel™, RAPP Polymere, GmbH) of from 0.01 M to 0.13 M.

The assay of ACE inhibition by the other analogues both corroborated known structure-function relationships and identified new relationships. For example, it is known that hydrophobic and basic substituents incorporated at $R_1$ and $R_2$ result in highly inhibitory compounds (see Patchett et al., Science 288:280, 1980). As shown in FIGS. 7A and 7B, a nonhydrophic group at $R_1$ (i.e., $R_{1b}$ or $R_{1c}$) can have a deleterious effect on inhibitory activity even in the presence of a hydrophobic group at $R_2$ (i.e., $R_{2a}$). A negatively charged group at $R_2$ (i.e., $R_{2c}$) abolishes inhibitory activity by providing an energetically unfavorable interaction with a putative carboxyl group on the enzyme (compare $R_{1a}+R_{2a}$ and $R_{1a}+R_{2c}$) Such a carboxyl group would be expected in the enzyme pocket that interacts favorably with inhibitors bearing basic substituents in the $R_2$ position. Comparing the inhibitory activity of compounds $R_{1a}+R_{2a}$ and $R_{1a}+R_{2b}$ indicates that the 2-nitro group is a moderately unfavorable modification revealing a more subtle structure-function relationship of the active site not previously appreciated. The intermediate effect of the 2-nitro group probably reflects a steric restriction on 2-phenyl substitutions. Despite the low binding affinities of these analogues, the porous coating of the present invention provided sufficient amounts of each compound to identify the above structure-function relationships.

This example demonstrates that (1) the porous coating provides a successful substrate for creating arrays of small-molecule drug candidates using solid-phase synthesis, (2) the ligand surface density is sufficient to perform functional assays using ligands from individual array elements, (3) the ligand surface density is sufficient to perform functional assays using ligands with low to moderate binding affinities, and (5) the porous array of small molecules provides a successful system for identifying relationships between drug structure and drug binding.

From the foregoing, it will be appreciated that, although specific embodiments of the invention have been described herein for the purpose of illustration, various modifications may be made without deviating from the spirit and scope of the invention. Accordingly, the present invention is not limited except by the appended claims.

What is claimed is:

1. A coated article comprising a substrate having a continuous porous coating of substantially uniform thickness, wherein the coating comprises a gelled network of particles, wherein the porous coating has two or more different compounds attached thereto, and wherein the compounds are attached at known discrete full thickness volumes, each occupying an area on the substrate of less than 1,000.000 $\mu m^2$.

2. A coated article according to claim 1, wherein each particle comprises one or more materials independently selected from the group consisting of carbon, activated carbon, fluorinated carbon, styrenedivinylbenzene copolymers, polystyrene, zeolites, oxides of antimony and oxides of metals present within Group III and Group IV of the Periodic Table.

3. A coated article according to claim 2, wherein each particle comprises one or more materials independently selected from the group consisting of alumina, silica, silicalite, fumed silica, oxides of tin and titania.

4. A coated article according to claim 1, wherein the particles are substantially spherical particles of silica.

5. A coated article according to claim 1, wherein the particles have a primary particle size of less than 1000 Å.

6. A coated article according to claim 1, wherein the particles have a primary particle size of less than 500 Å.

7. A coated article according to claim 1, wherein the particles have a primary particle size of less than 100 Å.

8. A coated article according to claim 1, wherein the particles have a primary particle size of less than 5 Å.

9. A coated article according to claim 1, wherein the porous coating has a thickness ranging from 0.05 to 25 microns.

10. A coated article according to claim 1, wherein the porous coating has a surface area that is greater than 50 meters$^2$/g.

11. A coated article according to claim 1, wherein the porous coating has a surface area of at least 100 square microns per cubic micron of porous coating.

12. A coated article according to claim 1, wherein the gelled network of particles further comprises a polymer of a hydrolyzed metal alkoxide.

13. A coated article according to claim 12, wherein the hydrolyzed metal alkoxide has the formula:

$$M(OR)_x$$

wherein M is selected from the group consisting of Si, Ti, Al, B, Zr, Er, Cr, Ga, Ge, Hf, Fe, Ca, Cr, La, Mg, Nb, K, Pr, Sm, Na, Ta, Te, Tl, Sn, W, V, Y, and Zn; R is hydrogen, an alkyl group or an aryl group, and x is 3 or 4.

14. A coated article according to claim 13, wherein the hydrolyzed metal alkoxide is hydrolyzed tetraethyoxysilane.

15. A coated article according to claim 1, wherein the substrate is glass.

16. A coated article according to claim 1, wherein the substrate comprises an adhesive layer in contact with the porous coating.

17. A coated article according to claim 16, wherein the adhesive layer comprises one or more polymers of a hydrolyzed organo-metal alkoxide of the formula:

$$R_n'M(OR)_x$$

wherein M is selected from the group consisting of Si, Ti, Al, B, Zr, Er, Cr, Ga, Ge, Hf, Fe, Ca, Cr, La, Mg, Nb, K, Pr, Sm, Na, Ta, Te, Tl, Sn, W, V, Y, and Zn; R' is a monovalent organic group containing between 1 and 12 carbon atoms; R is hydrogen, an alkyl group or an aryl group and n and x are integers independently selected from the group consisting of 0, 1, 2, 3 and 4.

18. A coated article according to claim 17, wherein the adhesive layer comprises a polymer of hydrolyzed tetraethoxysilane.

19. A coated article according to claim 1, wherein the compounds are covalently attached to the porous coating.

20. A coated article according to claim 1, wherein the compounds are adsorbed to the porous coating.

21. A coated article according to claim 1, wherein at least one compound is attached to the porous coating by a linker.

22. A coated article according to claim 21, wherein the linker comprises a photocleavable moiety or an enzyme cleavable moiety.

23. A coated article according to claim 21, wherein the linker comprises an acid labile moiety or a base labile moiety.

24. A coated article according to claim 23, wherein the linker comprises the formula:

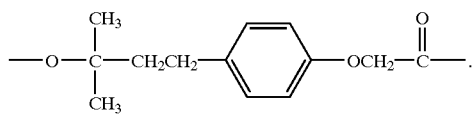

25. A coated article according to claim 21, wherein the linker is an organoalkoxysilane molecule attached to the porous coating via a siloxane bond.

26. A coated article according to claim 25, wherein the linker is 3-amino-propyltriethoxysilane or bis(2-hydroxyethyl)-3-aminopropyltriethoxysilane.

27. A coated article according to claim 21, wherein the linker comprises the formula:

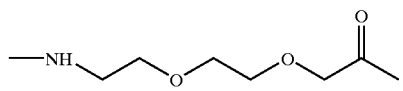

28. A coated article according to claim 1, wherein at least 90% of the compounds have the same structure.

29. A coated article according to claim 1, wherein at least 10% of the compounds have the same structure.

30. A coated article according to claim 1, wherein at least $10^3$ different compounds are attached to the porous coating at known discrete full thickness volumes.

31. A coated article according to claim 1, wherein at least $10^5$ different compounds are attached to the porous coating at known discrete full thickness volumes.

32. A coated article according to claim 1, wherein at least $10^6$ different compounds are attached to the porous coating at known discrete full thickness volumes.

33. A coated article according to claim 1, wherein the compounds are independently selected from the group consisting of nucleobase polymers and peptides.

34. A coated article according to claim 1, comprising an enalaprilat analogue of the formula:

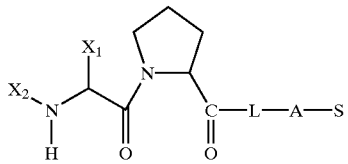

wherein S is the porous coating, A is aminopropyltriethoxysilane, L is a divalent linker, $X_1$ is a monovalent organic group or hydrogen, and $X_2$ is a monovalent organic group or hydrogen.

35. A coated article according to claim 34, wherein $X_1$ is a monovalent organic group comprising one or more acid labile protecting groups.

36. A coated article according to claim 34, wherein $X_2$ is a monovalent organic group comprising one or more acid labile protecting groups.

37. A coated article according to claim 1, wherein the compounds are attached at known discrete full thickness volumes, each occupying an area on the substrate of less than 1,000 $\mu m^2$.

38. A coated article according to claim 1, wherein the compounds are attached at known discrete full thickness volumes, each occupying an area on the substrate of less than 10 $\mu m^2$.

39. A coated article according to claim 1, wherein the average pore size of the porous coating substantially approximates the primary particle size.

40. A coated article according to claim 1, wherein the average pore size ranges from 1 to 1000 nm.

41. A method for making a coated article with two or more compounds attached thereto, comprising the steps of:
(a) applying to a substrate a substantially uniform layer of a solution comprising metal oxide particles dispersed in a volatile liquid;
(b) evaporating the volatile liquid from the layer, forming a gelled network of metal oxide particles on the substrate, wherein the gelled network forms a porous coating ranging from 0.05 to 25 microns thick; and
(c) attaching two or more compounds to discrete known regions of the porous coating, wherein the compounds are attached at known discrete full thickness volumes, each occupying an area on the substrate of less than 1,000,000 $\mu m^2$, and therefrom generating a coated article comprising a substrate having a porous coating with two or more compounds attached thereto.

42. A method according to claim 41, wherein prior to the step of attaching two or more compounds, the porous coating is cured at a temperature and for a time sufficient to increase the porous coating strength.

43. A method according to claim 41, wherein each metal oxide particle comprises one or more materials independently selected from the group consisting of oxides of antimony and oxides of metals present within Group III or Group IV of the Periodic Table.

44. A method according to claim 43, wherein each metal oxide particle comprises one or more materials independently selected from the group consisting of tin oxide, titania, antimony oxide, silica, alumina, silicalite and fumed silica.

45. A method according to claim 41, wherein the solution comprises 0.2 to 25 weight percent of metal oxide particles with a primary particle size of less than 1000 Å.

46. A method according to claim 41, wherein the solution further comprises extended polymers of a substantially hydrolyzed metal alkoxide linked to the metal oxide particles, wherein the weight ratio of metal oxide particles to the substantially hydrolyzed metal alkoxide ranges from 1 to 1000.

47. A method according to claim 46, wherein the solution comprises 20 $\mu$mole to 2000 $\mu$mole of metal alkoxide per gram of metal oxide particles.

48. A method according to claim 46, wherein the solution comprises from 60 $\mu$mole to 240 $\mu$mole of metal alkoxide per gram of metal oxide particles.

49. A method according to claim 46, wherein the substantially hydrolyzed metal alkoxide is substantially hydrolyzed tetraethoxysilane.

50. A method according to claim 46, wherein the solution has a pH ranging from 4 to 5.

51. A method according to claim 46, wherein the volatile liquid is 70 to 90 volume percent ethanol, with the balance water.

52. A method according to claim 46, wherein the solution is aged for greater than one day at 4° C. prior to application to the substrate.

53. A method according to claim 41, wherein the layer is cured at at least 120° C. for 15 minutes.

54. A method according to claim 41, wherein at least one compound is attached to the substrate by a linker.

55. A method according to claim 54, wherein the linker is an organoalkoxysilane molecule attached to the porous coating via a siloxane bond.

56. A method according to claim 55, wherein the linker is 3-amino-propyltriethoxysilane or bis(2-hydroxyethyl)-3-aminopropyltriethoxysilane.

57. A method according to claim 54, wherein the linker comprises a photocleavable moiety, an enzyme cleavable moiety, an acid labile moiety or a base labile moiety.

58. A method according to claim 53, wherein the linker comprises the formula:

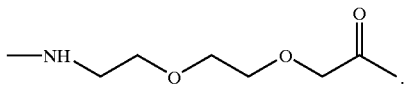

59. A method according to claim 42, wherein following evaporation of the volatile liquid and before the step of curing, the method comprises the steps of: (i) applying a fortifying solution comprising an aged sol of hydrolyzed tetraethoxysilane in a volatile solvent to the layer; and (ii) evaporating the volatile solvent to yield a fortifying layer wherein the weight ratio of metal oxide particles to the hydrolyzed tetraethoxysilane ranges from 1 to 1000.

60. A method according to claim 59, wherein the fortifying solution is an aged sol comprising 0.5 volume percent tetraethoxysilane, 0.15 volume percent water and 0.1 mM nitric acid, with the balance ethanol.

61. A method according to claim 41, wherein the substrate comprises an adhesive layer.

62. A method according to claim 61, wherein the adhesive layer comprises a polymer of hydrolyzed tetraethoxysilane.

63. A method according to claim 62, wherein the adhesive layer is generated by:
(i) applying onto the substrate a substantially uniform layer of an adhesive solution comprising an aged sol of hydrolyzed tetraethoxysilane in a volatile solvent; and
(ii) evaporating the volatile solvent from the layer and curing the layer to deposit a 0.002 to 2 micron thick adhesive layer of polymer of hydrolyzed tetraethoxysilane.

64. A method according to claim 63, wherein the adhesive solution is an aged sol comprising 1.5 volume percent tetraethoxysilane, 0.45 volume percent water, and 0.3 mM nitric acid with the balance ethanol.

65. A method according to claim 63, wherein the volatile solvent is evaporated at room temperature.

66. A method according to claim 63, wherein the adhesive layer is cured at at least 120° C. for at least 15 minutes.

67. A method according to claim 41, wherein at least $10^4$ different compounds are attached to the porous coating at known discrete full thickness volumes of the porous coating.

68. A method according to claim 41, wherein each of the known discrete full thickness volumes occupies an area on the substrate of less than about 10,000 $\mu m^2$.

69. A method according to claim 41, wherein the compounds are attached to discrete known regions by a process comprising the steps of:
(i) attaching first molecules to the porous coating;
(ii) covering the first molecules with a layer of photoresist;
(iii) irradiating the photoresist such that photoresist is removed from first molecules in a first region, but not from first molecules in a second region;
(iv) contacting first molecules from which photoresist has been removed with a first reagent, forming second molecules attached the porous coating; and
(v) removing remaining photoresist.

70. A method according to claim 69, wherein the photoresist is a positive photoresist comprising a polyamide.

71. A coated article comprising a substrate having at least two discrete known regions with continuous porous coatings, wherein each coating has a substantially uniform thickness and comprises a gelled network of particles, and wherein each porous coating has at least one compound attached thereto, and wherein a different compound is attached to each of the porous coatings.

72. A coated article according to claim 71, wherein each particle comprises one or more materials independently selected from the group consisting of carbon, activated carbon, fluorinated carbon, styrenedivinylbenzene copolymers, polystyrene, zeolites, oxides of antimony and oxides of metals present within Group III and Group IV of the Periodic Table.

73. A coated article according to claim 72, wherein each particle comprises one or more materials independently selected from the group consisting of alumina, silica, silicalite, fumed silica, oxides of tin and titania.

74. A coated article according to claim 72, wherein the particles are substantially spherical silica particles.

75. A coated article according to claim 71, wherein the particles have a primary particle size of less than 1000 Å.

76. A coated article according to claim 71, wherein the continuous gelled network of particles further comprises a polymer of a substantially hydrolyzed metal alkoxide.

77. A coated article according to claim 76, wherein the substantially hydrolyzed metal alkoxide is substantially hydrolyzed tetraethyoxysilane.

78. A coated article according to claim 71, wherein the substrate comprises an adhesive layer.

79. A coated article according to claim 78, wherein the adhesive layer comprises polymers of hydrolyzed tetraethoxysilane.

80. A coated article according to claim 71, wherein the substrate has more than $10^4$ separate porous coatings with attached compounds.

81. A coated article according to claim 71, wherein at least one compound is attached to the porous coatings via a linker.

82. A coated article according to claim 81, wherein the linker is an organoalkoxysilane molecule attached to the porous coatings via siloxane bonds.

83. A coated article according to claim 81, wherein the linker comprises a photocleavable moiety or an enzyme cleavable moiety.

84. A coated article according to claim 81, wherein the linker comprises an acid labile moiety or a base labile moiety.

85. A coated article according to claim 71, wherein the attached compounds are selected from the group consisting of nucleobase polymers, peptides and enalaprilat analogues.

86. A coated article according to claim 71, wherein each of the porous coatings further comprises a fortifying layer of a polymer of hydrolyzed tetraethoxysilane.

87. A coated article according to claim 71, wherein the average pore size of each of the separate porous coatings substantially approximates the particle size.

88. A method of making a coated article comprising a substrate and at least two separate porous coatings, comprising the steps of:
(a) applying to a substrate a substantially uniform layer of a solution comprising metal oxide particles dispersed in a volatile liquid;
(b) evaporating the volatile liquid from the layer, forming a gelled network of metal oxide particles on the substrate, wherein the gelled network forms a porous coating ranging from 0.05 to 25 microns thick;

(c) covering the porous coating with a layer of photoresist comprising a base soluble component;

(d) irradiating the photoresist, such that a first region of photoresist is rendered substantially removable with an aqueous alkaline developer, and such that a second region is not so removable;

(e) contacting at least the first region with an aqueous alkaline developer to remove at least the first region of photoresist and porous coating underlying the first region, without substantially removing the second region of photoresist or porous coating underlying the second region;

(f) removing remaining photoresist with an organic solvent, resulting in separate porous coatings on discrete regions of the substrate; and (g) attaching one or more compounds to each of the separate porous coatings, and therefrom generating a substrate having at least two separate porous coatings, wherein each coating has a substantially uniform thickness and comprises a continuous gelled network of metal oxide particles and polymers of a hydrolyzed metal alkoxide, and wherein a different compound is attached to each of the porous coatings.

89. A method according to claim 88, wherein each metal oxide particle comprises one or more materials independently selected from the group consisting of oxides of antimony and oxides of metals present within Group III or Group IV of the Periodic Table.

90. A method according to claim 89, wherein each metal oxide particle comprises one or more materials independently selected from the group consisting of tin oxide, titania, antimony oxide, silica, alumina, silicalite and fumed silica.

91. A method according to claim 88, wherein the metal oxide particles are substantially spherical particles of silica.

92. A method according to claim 88, wherein at least one compound is attached via a linker.

93. A method according to claim 88, wherein the solution comprises 0.2 to 25 weight percent of metal oxide particles with a primary particle size of less than 500 Å.

94. A method according to claim 88, wherein the solution comprises 20 μmole to 2000 μmole of metal alkoxide per gram of metal oxide particles.

95. A method according to claim 88, wherein the solution comprises 60 μmole to 240 μmole of metal alkoxide per gram of metal oxide particles.

96. A method according to claim 88, wherein the substantially hydrolyzed metal alkoxide is substantially hydrolyzed tetraethoxysilane.

97. A method according to claim 88, wherein the solution has a pH ranging from 4 to 5.

98. A method according to claim 88, wherein the volatile liquid is 70 to 90 volume percent ethanol, with the balance water.

99. A method according to claim 88, wherein the solution is aged for greater than one day at 4° C.

100. A method according to claim 88, wherein the volatile liquid is evaporated at room temperature.

101. A method according to claim 88, wherein the photoresist comprises a diazoquinone.

102. A method according to claim 88, wherein the radiation is selected from the group consisting of coherent, incoherent, x-ray, deep ultraviolet, mid ultraviolet, near ultraviolet, visible and infrared light.

103. A method according to claim 88, wherein the step of irradiating comprises:

(i) placing a mask between a light source and the layer of photoresist, wherein the mask comprises first regions that transmit at least one selected wavelength of light and second regions that do not substantially transmit the selected wavelength of light.

(ii) irradiating the mask with a light source emitting the selected wavelength, such that light is transmitted to at least a first region of the layer of photoresist and is not substantially transmitted to at least the second region of the layer of photoresist.

104. A method according to claim 88, wherein the base soluble component is a phenolic polymer having the formula:

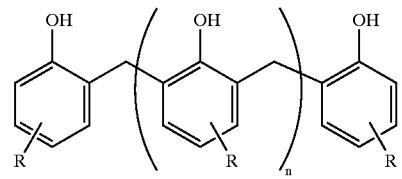

wherein R is hydrogen or an alkyl group, and n is an average ranging from 0 to 13.

105. A method according to claim 88, wherein the aqueous alkaline developer comprises a base selected from the group consisting of potassium hydroxide, sodium hydroxide and tetramethyl ammonium hydroxide.

106. A method according to claim 88, wherein the organic solvent is acetone.

107. A method according to claim 88, wherein each separate porous coating is less then 25 microns thick.

108. A method according to claim 88, wherein at least one compound is attached via a linker.

109. A method according to claim 88, wherein prior to the step of attaching one or more compounds, the separate porous coatings are cured at a temperature and for time sufficient to increase the porous coating strength.

110. A method according to claim 88, wherein following removal of remaining photoresist and before the step attaching one or more compounds, the method comprises the steps of: (i) applying a fortifying solution comprising an aged sol of hydrolyzed tetraethoxysilane in a volatile solvent to the layer of aged solution; and (ii) evaporating the volatile solvent to yield a fortifying layer wherein the weight ratio of metal oxide particles to the hydrolyzed tetraethoxysilane ranges from 1 to 1000.

111. A method according to claim 110, wherein the fortifying solution is an aged sol comprising 0.5 volume percent tetraethoxysilane, 0.15 volume percent water, and 0.1 mM nitric acid with the balance ethanol.

112. A method according to claim 88, wherein the substrate comprises an adhesive layer of a polymer of hydrolyzed tetraethoxysilane.

113. A method according to claim 112, wherein the adhesive layer is generated by:

(i) applying onto the substrate a substantially uniform layer of an adhesive solution comprising an aged sol of hydrolyzed tetraethoxysilane in a volatile solvent; and (ii) evaporating the volatile solvent from the layer and curing the layer to deposit a 0.002 to 2 micron thick adhesive layer of polymer of hydrolyzed tetraethoxysilane.

114. A method according to claim 113, wherein the adhesive solution is an aged sol comprising 1.5 volume percent tetraethoxysilane, 0.45 volume percent water and 0.3 mM nitric acid, with the balance ethanol.

115. A method according to claim 113, wherein the volatile solvent is evaporated at room temperature.

116. A method according to claim 113, wherein the adhesive layer is cured at at least 120° C. for at least 15 minutes.

117. A method according to claim 88, wherein the substrate has more than $10^4$ separate porous coatings in known regions, each of the porous coatings with different attached compounds.

118. A method according to claim 88, wherein each of the separate porous coatings occupies an area on the substrate of less than about 10,000 $\mu m^2$.

119. A method according to claim 88, wherein the photoresist is a positive photoresist.

120. A method according to claim 88, wherein the photoresist is a negative photoresist.

121. A method according to claim 88, wherein the compounds are attached to discrete known regions by a process comprising the steps of:
(i) attaching first molecules to the separate porous coatings;
(ii) covering the first molecules by a layer of second photoresist;
(iii) irradiating at least a portion of the second photoresist, such that second photoresist is removed from the first molecules in the first region;
(iv) contacting first molecules from which photoresist has been removed with a first reagent, forming second molecules attached to the separate porous coatings; and
(v) removing remaining second photoresist.

122. A method according to claim 121, wherein the second photoresist comprises a polyamide.

123. A method according to claim 121, wherein the second photoresist is a positive photoresist.

124. A method according to claim 121, wherein the second photoresist is a negative photoresist.

125. A method of identifying at least one compound that specifically binds a receptor, the method comprising the sequential steps of
(a) providing a coated article according to claim 1 or claim 72;
(b) contacting said coated article with a receptor; and
(c) determining whether one or more of the compounds attached to the porous coating specifically bind to the receptor.

126. A method according to claim 125, wherein each compound attached to the porous coating is independently selected from the group consisting of nucleobase polymers and peptides.

127. A method according to claim 126, wherein the compounds are antisense nucleic acid molecules.

128. A method according to claim 125, wherein the receptor is a nucleobase polymer, enzyme, cell receptor or antibody.

129. A method according to claim 125, wherein the receptor further comprises a detectable marker and wherein step (b) comprises detecting a location of the marker on the porous coating.

130. A method according to claim 129, wherein the marker is a radioactive marker or a fluorescent marker.

131. A method for identifying at least one compound that specifically binds a receptor, the method comprising the steps of:
(a) providing a coated article according to claim 1 or claim 71;
(b) simultaneously or in either order:
(i) detaching one or more compounds from said coated article; and
(ii) contacting the detached compound(s) with a receptor, and (c) determining whether the compound(s) specifically bind to the receptor.

132. A method according to claim 131, wherein the compounds are attached to the substrate via a linker.

133. A method according to claim 132, wherein the linker comprises a photocleavable moiety, and wherein the compound(s) are detached from the substrate by irradiation with light.

134. A method according to claim 133, wherein the light is selected from the group consisting of ultraviolet, visible and infrared light.

135. A method according to claim 132, wherein the linker comprises a recognition site that is cleaved by an enzyme, and wherein the compound(s) are detached from the substrate by contact with an enzyme.

136. A method according to claim 132, wherein the linker comprises an acid labile moiety or a base labile moiety, and wherein the compound(s) are detached from the substrate by contact with an acidic or basic chemical.

137. A method according to claim 136, wherein the chemical is selected from the group consisting of liquid trifluoroacetic acid, gaseous trifluoro acetic acid, liquid ammonia and gaseous ammonia.

138. A method according to claim 131, wherein the receptor is an enzyme.

139. A method according to claim 138, wherein the enzyme is angiotensin converting enzyme.

140. A method according to claim 131, wherein step (c) further comprises:
(i) contacting the receptor with an indicator compound having a detectable property in the presence of receptor bound to a compound; and
(ii) determining the presence or absence of the detectable property.

141. A method according to claim 140, wherein the detectable property is selected from the group consisting of color, light absorbance, light transmission, fluorescence, fluorescence resonance energy transfer, fluorescence polarization, phosphorescence, catalytic activity, molecular weight, charge, density, melting point, chromatographic mobility, turbidity, electrophoretic mobility, mass spectrum, ultraviolet spectrum, infrared spectrum, nuclear magnetic resonance spectrum, elemental composition, and x-ray diffraction.

142. A method according to claim 141, wherein the indicator compound is furylacryloylphenyalanylglycylglycine and wherein the receptor is angiotensin converting enzyme.

143. A method according to claim 131, wherein the coated article comprises enalaprilat analogues of the formula:

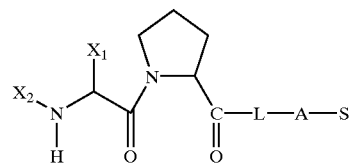

wherein S is the porous coating, A is aminopropyltriethoxysilane, L is a divalent linker molecule, $X_1$ is a monovalent organic group or hydrogen, and $X_2$ is a monovalent organic group or hydrogen.

144. A method for isolating a target receptor, comprising the steps of:
(a) providing a coated article according to claim 1 or claim 71;

(b) contacting said coated article with a composition comprising a target receptor, wherein at least one attached compound binds to the target receptor;

(c) removing unbound components of the composition from the array; and (d) separating the target receptor from the coated article, and therefrom isolating the target receptor.

145. A coated article according to claim 1 or claim 71, wherein at least 5% of the attached compounds comprise a target receptor modifying group that labels, reconforms, cleaves, covalently binds or intercalates into a bound target receptor.

146. A method for modifying a receptor, comprising the steps of:

(a) providing a coated article according to claim 145; and (b) contacting said coated article with a composition comprising a target receptor.

147. A method for hybridizing an antisense molecule to a target nucleic acid molecule, comprising the steps of:

(a) providing a coated article according to claim 1 or claim 71;

(b) contacting said coated article with a composition comprising a target nucleic acid molecule, wherein the attached compounds are antisense molecules; and (c) detaching one or more compounds from the array, and thereby hybridizing an antisense molecule to the target nucleic acid molecule.

148. A method for hybridizing an antisense molecule to a target nucleic acid molecule, comprising the steps of:

(a) providing a coated article according to claim 1 or claim 71;

(b) detaching one or more compounds from said coated article, wherein the attached compounds are antisense molecules; and (c) contacting the compound(s) with a composition comprising a target nucleic acid molecule, and thereby hybridizing an antisense molecule to the target nucleic acid molecule.

149. A coated article according to claim 1 or claim 71, wherein the attached compounds are nucleobase polymers, wherein the nucleobase polymers comprise at least one set of 2 to 10 different probes of identical length, wherein:

(a) one probe is completely complementary to a 4 to 40 nucleotide portion of a reference sequence first set that is exactly complementary to a reference sequence and comprises nucleobase polymers that completely span the reference sequence and, relative to the reference sequence, overlap one another; and (b) the remaining probe(s) of the set are each identical to the completely complementary probe except that each contains one nucleobase substitution relative to the completely complementary probe, wherein each substitution is at the same position relative to the reference sequence.

150. A coated article comprising a substrate having a plurality of continuous porous coatings thereon of substantially uniform thickness, wherein each of the porous coatings comprises a continuous gelled network of metal oxide particles and polymers of hydrolyzed metal alkoxide, and wherein each of the porous coatings has a surface area measuring greater than 50 meters$^2$/g.

151. A coated article according to claim 150, wherein the metal alkoxide is tetraethoxysilane.

152. A coated article comprising a substrate having at least five separate distinct porous coatings per square centimeter, wherein each coating is continuous and has a substantially uniform thickness and comprises a continuous gelled network of particles, and wherein each of the separate porous coatings occupies an area on the substrate of less than about 1,000,000 $\mu$m$^2$.

153. A coated article according to claim 152, wherein the substrate has at least 100 separate distinct porous coatings per square centimeter.

154. A coated article comprising a substrate having at least two discrete known regions with continuous porous coatings, wherein each coating has a substantially uniform thickness and comprises a gelled network of particles, and wherein each porous coating has at least one compound attached thereto, and wherein each of the separate porous coating occupies an area on the substrate of less than about 10,000 $\mu$m$^2$.

155. A coated article comprising a substrate having at least two discrete known regions with continuous porous coatings, wherein each coating has a substantially uniform thickness and comprises a gelled network of particles, and wherein each porous coating has at least one compound attached thereto, and wherein the porous coatings have a surface area measuring greater than 50 meters $^2$/g.

* * * * *

UNITED STATES PATENT AND TRADEMARK OFFICE
CERTIFICATE OF CORRECTION

PATENT NO.     : 6,951,682 B1
DATED          : October 4, 2005
INVENTOR(S)    : John A. Zebala It is certified that error appears in the above-identified patent and that said Letters Patent is hereby corrected as shown below:

Column 89,
Line 49, the period "." within the numeral "1,000.000" should read as a comma -- , --.

Signed and Sealed this

Twenty-ninth Day of November, 2005

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 6,951,682 B1 | Page 1 of 1 |
| APPLICATION NO. | : 09/332815 | |
| DATED | : October 4, 2005 | |
| INVENTOR(S) | : John A. Zebala | |

It is certified that error appears in the above-identified patent and that said Letters Patent is hereby corrected as shown below:

Column 1, Line 9 please insert a Government Rights Statement as shown below:

--This invention was made with government support under Grant Number DAMD17-96-1-6120 awarded by the U.S. Army Medical Research and Material Command. The government has certain rights to this invention.--

Signed and Sealed this
Eighth Day of January, 2013

David J. Kappos
*Director of the United States Patent and Trademark Office*

(12) EX PARTE REEXAMINATION CERTIFICATE (7586th)
United States Patent
Zebala

(10) Number: US 6,951,682 C1
(45) Certificate Issued: Jun. 29, 2010

(54) POROUS COATINGS BEARING LIGAND ARRAYS AND USE THEREOF

(75) Inventor: John A. Zebala, Redmond, WA (US)

(73) Assignee: Syntrix Biosystems, Inc., Auburn, WA (US)

Reexamination Request:
No. 90/011,998, Jun. 11, 2008

Reexamination Certificate for:
Patent No.: 6,951,682
Issued: Oct. 4, 2005
Appl. No.: 09/332,815
Filed: Sep. 17, 1999

Certificate of Correction issued Nov. 29, 2005.

Related U.S. Application Data

(60) Provisional application No. 60/110,529, filed on Dec. 1, 1998.

(51) Int. Cl.
| | |
|---|---|
| C03C 17/00 | (2006.01) |
| C07B 61/00 | (2006.01) |
| C12Q 1/68 | (2006.01) |
| C12Q 1/37 | (2006.01) |
| G01N 33/552 | (2006.01) |
| G01N 33/551 | (2006.01) |
| B01J 19/00 | (2006.01) |
| C07H 21/00 | (2006.01) |
| C07K 5/02 | (2006.01) |
| C07K 5/00 | (2006.01) |

(52) U.S. Cl. ............... 428/312.2; 428/312.8; 428/315.7; 428/317.1; 435/4; 435/7.1; 435/7.7; 435/7.71; 435/7.72; 435/7.8; 435/7.9; 436/518; 436/519; 436/523

(58) Field of Classification Search .......................... None
See application file for complete search history.

(56) References Cited

U.S. PATENT DOCUMENTS

| | | |
|---|---|---|
| 2,601,123 A | 6/1952 | Moulton |
| 3,910,851 A | 10/1975 | Messing |
| 4,816,333 A | 3/1989 | Lange et al. |
| 5,120,600 A | 6/1992 | Pirrung et al. |
| 5,224,972 A | 7/1993 | Frye et al. |
| 5,268,198 A | 12/1993 | Yamasaki et al. |
| 5,519,088 A | 5/1996 | Itoh et al. |
| 5,589,396 A | 12/1996 | Frye et al. |
| 5,624,875 A | 4/1997 | Nakanishi et al. |
| 5,624,998 A | 4/1997 | Itoh et al. |
| 5,686,602 A | 11/1997 | Farooq et al. |
| 5,879,881 A | 3/1999 | Rubenstein |
| 5,900,481 A | 5/1999 | Lough et al. |
| 6,023,540 A | 2/2000 | Walt et al. |
| 6,951,682 B1 | 10/2005 | Zebala |

FOREIGN PATENT DOCUMENTS

| | | |
|---|---|---|
| JP | 59001777 | 1/1984 |
| JP | 5254819 | 10/1993 |
| WO | WO90/05910 | 5/1990 |
| WO | WO94/14088 | 6/1994 |
| WO | WO 97/16569 | 5/1997 |
| WO | WO 97/39151 | 10/1997 |
| WO | WO 97/40385 | 10/1997 |
| WO | WO 99/02266 | 1/1999 |
| WO | WO 00/33078 | 6/2000 |

OTHER PUBLICATIONS

Beattie et al. "Advances in Genosensor Research" Clin. Chem. 41(5):700–706, 1995.

Cathro et al. "Silica Low–Reflection Coatings for Collector Covers By a Dip–Coating Process" Solar Energy 32 (5):573–579, 1984.

(Continued)

*Primary Examiner*—Stephen J Stein

(57) ABSTRACT

Articles comprising substantially uniform porous coatings, which may be photopatterned, are provided. The use of such porous coatings increases the surface density of attached compounds within, for example, ligand arrays prepared by methods such as regionally selective solid-phase chemical synthesis. Arrays prepared using the porous coatings may be used within a variety of diagnostic and drug discovery assays.

| Objective Magnification | No Coating (prior art) | Objective Magnification | Patterned Porous Coating (present invention) |
|---|---|---|---|
| 2x |  | 2x | 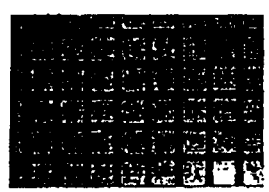 |

OTHER PUBLICATIONS

Chu et al. "Glycidoxypropyltrimethoxysilane Modified Colloifal Silica Coatings" Mat. Res. Soc. Symp. Proc. 435:221–225, 1996.

Daniels et al. "Use of an Organosilane Coupling Agent in Colloidal Silica Coatings" Mat. Res. Soc. Symp. Proc. 435:215–220, 1996.

Frye et al. "Sol–Gel Coatings on Acoustic Wave Devices: Thin Film Characterization and Chemical Sensor Development" Mat. Res. Soc. Symp. Proc. 180:583–593, 1990.

Guschin et al. "Manual Manufacturing of Oligonucleotide, DNA and Protein Microchips" Anal. Biochem. 250 (2):203–211, 1997.

Pu et al. "Photobinding of Colloidal Particles by Means of Surface Modification. IV. Negative and Positive Working Imaging by Control of Substrate Surface Energy" J. Imaging Sci. 33(5):177–183, 1989.

Yershov et al. "DNA Analysis and Diagnostics on Oligonucleotide Microchips" Proc. Natl. Acad. Sci. USA 93:4913–4918, 1996.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-7, 9, 10, 15, 16, 19-23, 28-33, 37-40, 154 and 155 is confirmed.

Claims 71 and 125 are determined to be patentable as amended.

Claims 72-75, 78, 80, 81, 83-85, 87 and 126-130, dependent on an amended claim, are determined to be patentable.

Claims 8, 11-14, 17, 18, 24-27, 34-36, 41-70, 76, 77, 79, 82, 86, 88-124 and 131-153 were not reexamined.

71. A coated article comprising a substrate having at least two discrete known regions with continuous porous coatings, wherein each *porous* coating has a substantially uniform thickness and comprises a gelled network of particles, and wherein each porous coating has at least one compound attached thereto, and wherein a different compound is attached to each of the porous coatings.

125. A method of identifying at least one compound that specifically binds a receptor, the method comprising the sequential steps of (a) providing a coated article according to claim 1 or claim [72] *71*; (b) contacting said coated article with a receptor; and (c) determining whether one or more of the compounds attached to the porous coating specifically bind to the receptor.

\* \* \* \* \*

US006951682C2

(12) EX PARTE REEXAMINATION CERTIFICATE (10527th)

United States Patent
Zebala

(10) Number: US 6,951,682 C2
(45) Certificate Issued: Mar. 10, 2015

(54) POROUS COATINGS BEARING LIGAND ARRAYS AND USE THEREOF

(75) Inventor: John A. Zebala, Redmond, WA (US)

(73) Assignee: The United States of America as represented by the Secretary of the Army, Washington, DC (US)

Reexamination Request:
No. 90/013,232, May 7, 2014

Reexamination Certificate for:
Patent No.: 6,951,682
Issued: Oct. 4, 2005
Appl. No.: 09/332,815
Filed: Sep. 17, 1999

Reexamination Certificate C1 6,951,682 issued Jun. 29, 2010

Certificate of Correction issued Nov. 29, 2005
Certificate of Correction issued Jan. 8, 2013

(51) Int. Cl.
*B01J 19/00* (2006.01)
*C07B 61/00* (2006.01)
(Continued)

(52) U.S. Cl.
CPC .......... *B01J 19/0046* (2013.01); *C03C 17/007* (2013.01); *C07H 21/00* (2013.01); *C12Q 1/6841* (2013.01); *C12Q 1/37* (2013.01); *B01J 2219/00432* (2013.01); *B82Y 30/00* (2013.01); *C07K 5/0222* (2013.01); *C03C 17/009* (2013.01); *C12Q 1/6809* (2013.01); *G01N 33/552* (2013.01); *B01J 2219/005* (2013.01); *B01J 2219/00497* (2013.01); *B01J 2219/00527* (2013.01); *B01J 2219/00529* (2013.01); *B01J 2219/00585* (2013.01); *B01J 2219/0059* (2013.01); *B01J 2219/00596* (2013.01); *B01J 2219/00605* (2013.01); *B01J 2219/00612* (2013.01); *B01J 2219/00617* (2013.01); *B01J 2219/00621* (2013.01); *B01J 2219/00626* (2013.01); *B01J 2219/00637* (2013.01); *B01J 2219/00644* (2013.01); *B01J 2219/00648* (2013.01); *B01J 2219/00659* (2013.01); *B01J 2219/00675* (2013.01); *B01J 2219/00702* (2013.01); *B01J 2219/00711* (2013.01); *B01J 2219/0072* (2013.01); *B01J 2219/00722* (2013.01); *B01J 2219/00725* (2013.01); *B01J 2219/00729* (2013.01); *C03C 2217/425* (2013.01); *C03C 2217/475* (2013.01); *C07B 2200/11* (2013.01); *C12Q 1/6837* (2013.01); *C40B 40/06* (2013.01); *C40B 40/10* (2013.01); *C40B 50/14* (2013.01); *C40B 60/14* (2013.01); *G01N 2333/96486* (2013.01)
USPC .................. 428/312.2; 428/312.8; 428/315.7; 428/317.1; 435/4; 435/7.1; 435/7.7; 435/7.71; 435/7.72; 435/7.8; 435/7.9; 436/518; 436/519; 436/523

(58) Field of Classification Search
None
See application file for complete search history.

(56) References Cited

To view the complete listing of prior art documents cited during the proceeding for Reexamination Control Number 90/013,232, please refer to the USPTO's public Patent Application Information Retrieval (PAIR) system under the Display References tab.

*Primary Examiner* — Elizabeth McKane

(57) ABSTRACT

Articles comprising substantially uniform porous coatings, which may be photopatterned, are provided. The use of such porous coatings increases the surface density of attached compounds within, for example, ligand arrays prepared by methods such as regionally selective solid-phase chemical synthesis. Arrays prepared using the porous coatings may be used within a variety of diagnostic and drug discovery assays.

Attention is directed to the decision of *Syntrix Biosystems, Inc. v. Illumina Inc.*, U.S. District-Washington Western (Tacoma) 3:10cv5870 relating to this patent. This reexamination may not have resolved all questions raised by this decision. See 37 CFR 1.552(c) for *ex parte* reexamination and 37 CFR 1.906(c) for *inter partes* reexamination.

Objective Magnification | No Coating (prior art)

2x

Objective Magnification | Patterned Porous Coating (present invention)

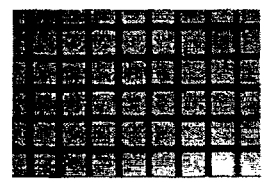

2x

(51) Int. Cl.
*C03C 17/00* (2006.01)
*C07H 21/00* (2006.01)
*C07K 5/02* (2006.01)
*C07K 5/00* (2006.01)
*C12Q 1/68* (2006.01)
*C12Q 1/37* (2006.01)
*G01N 33/551* (2006.01)
*G01N 33/552* (2006.01)
*B82Y 30/00* (2011.01)
*C40B 40/06* (2006.01)
*C40B 40/10* (2006.01)
*C40B 50/14* (2006.01)
*C40B 60/14* (2006.01)

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1 and 125 is confirmed.

Claims 2-124 and 126-155 were not reexamined.

* * * * *